US009730997B2

(12) United States Patent
Perri et al.

(10) Patent No.: US 9,730,997 B2
(45) Date of Patent: Aug. 15, 2017

(54) ALPHAVIRUS VECTORS FOR RESPIRATORY PATHOGEN VACCINES

(71) Applicant: NOVARTIS VACCINES AND DIAGNOSTICS, INC., East Hanover, NJ (US)

(72) Inventors: Silvia Perri, Castro Valley, CA (US); John Polo, Danville, CA (US); Yasushi Uematsu, Siena (IT); Catherine Greer, Oakland, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 41 days.

(21) Appl. No.: 14/463,831

(22) Filed: Aug. 20, 2014

(65) Prior Publication Data
US 2015/0024002 A1    Jan. 22, 2015

Related U.S. Application Data

(60) Continuation of application No. 12/791,140, filed on Jun. 1, 2010, now abandoned, which is a division of application No. 11/597,347, filed as application No. PCT/US2005/018225 on May 20, 2005, now abandoned.

(60) Provisional application No. 60/573,433, filed on May 21, 2004, provisional application No. 60/643,737, filed on Jan. 12, 2005.

(51) Int. Cl.
| A61K 39/145 | (2006.01) |
| C12N 15/86 | (2006.01) |
| A61K 39/12 | (2006.01) |
| A61K 39/155 | (2006.01) |
| A61K 39/00 | (2006.01) |

(52) U.S. Cl.
CPC ............ *A61K 39/12* (2013.01); *A61K 39/145* (2013.01); *A61K 39/155* (2013.01); *C12N 15/86* (2013.01); *A61K 2039/5252* (2013.01); *A61K 2039/5256* (2013.01); *A61K 2039/53* (2013.01); *A61K 2039/543* (2013.01); *A61K 2039/545* (2013.01); *A61K 2039/55544* (2013.01); *A61K 2039/55566* (2013.01); *A61K 2039/70* (2013.01); *C12N 2760/16122* (2013.01); *C12N 2760/16134* (2013.01); *C12N 2760/18322* (2013.01); *C12N 2760/18334* (2013.01); *C12N 2760/18522* (2013.01); *C12N 2760/18534* (2013.01); *C12N 2760/18622* (2013.01); *C12N 2760/18634* (2013.01); *C12N 2770/20022* (2013.01); *C12N 2770/20034* (2013.01); *C12N 2770/36143* (2013.01); *C12N 2830/20* (2013.01); *C12N 2830/60* (2013.01); *C12N 2840/20* (2013.01); *C12N 2840/203* (2013.01)

(58) Field of Classification Search
CPC .............. G01N 2333/181; A61K 39/12; A61K 2039/53; C12N 15/86; C12N 2770/36143; C12N 15/70; C07K 14/08
See application file for complete search history.

(56) References Cited

U.S. PATENT DOCUMENTS

| 6,008,035 A | 12/1999 | Johnston et al. |
| 6,156,558 A | 12/2000 | Johnston et al. |
| 7,419,674 B2 | 9/2008 | Chulay et al. |
| 7,442,381 B2 * | 10/2008 | Smith .................. C07K 14/005 |
| | | 424/218.1 |
| 7,541,038 B2 | 6/2009 | Kovacs et al. |
| 2003/0021766 A1 | 1/2003 | Vajdy et al. |
| 2004/0208848 A1 | 10/2004 | Smith et al. |
| 2006/0257852 A1 | 11/2006 | Rappuoli et al. |
| 2012/0114693 A1 | 5/2012 | Vajdy et al. |

FOREIGN PATENT DOCUMENTS

| WO | 01/81609 A2 | 11/2001 |
| WO | 02/053757 A1 | 7/2002 |
| WO | 02/080982 | 10/2002 |
| WO | 02/099035 A2 | 12/2002 |
| WO | 2004/000872 | 12/2003 |
| WO | 2005/016961 A1 | 2/2005 |

OTHER PUBLICATIONS

Smerdou et al. in Cell Engineering edited by M. Al-Rubeai et al. 2000, Kluwer Academic P.*
Davis et al. J. Virol. 1996, No. 6, pp. 3781-3787.*
Pushko et al. Virology 1997, vol. 239, pp. 389-401.*
Berglund et al. Vaccine, 1999, vol. 17,pp. 497-507.*
European Search Report dated Feb. 12, 2015, which issued during prosecution of European Application No. 14189933.6.
Peter Berglund, et al. "Enhancing immune responses using suicidal DNA vaccines" Nature Biotechnology 16 (6):562-565, Jun. 1998.
M. K. Hart, et al. "VEE virus replicons expressing influenza HA protect alphavirus-immune mice from intranasal challenge" Immunolgy Letters 69(1): Jun. 1999.
Pushko et al., "Replicon-Helper Systems from Attenuated Venezuelan Equine Encephalitis Virus . . . " 1997 12-22, pp. 389-401, Virology vol. 239, No. 2, Academic Press, Orlando USA.
Balasuriya et al., "Alphavirus replicon particles expressing the two major envelope proteins of equine arteritis irus induce high level protection against challenge with virulent virus in vaccinated horses," Vaccine. Feb. 22, 2002;20 (11-12): 1609-17.
Chen et al., "Vaccination and Recombinant Alphavirus or Immune-Stimulating Complex Antigen Against Respiratory Syncytial Virus," Journal of Immunology 169:3208-3216, 2002.

(Continued)

*Primary Examiner* — Bao Li
(74) *Attorney, Agent, or Firm* — McDermott Will & Emery LLP

(57) ABSTRACT

Described herein are compositions and methods for stimulating an immune response to one or more proteins derived from one or more respiratory pathogens. In particular, the invention relates to alphavirus replicons, alphavirus vector constructs, alphavirus replicon particles expressing one or more antigens derived from one or more respiratory pathogens as well as to method of making and using these immunogenic compositions.

16 Claims, 26 Drawing Sheets

(56) References Cited

OTHER PUBLICATIONS

Pushko et al., Individual and Bivalent Vaccines Based on Alphavirus Replicons Protect Guinea Pigs against infection with Lassa and Ebola Viruses, Journal of Virology 75:11677-11685, 2001.
Tang et al., "Effects of Human Metapneumovirus and Respiratory Syncytial Virus Antigen Insertion in Two 3' Proximal Genome Positions of Bovine/Human Parainfluenza Virus Type 3 on Virus Replication and Immunogenicity," Journal of Virology 77:10819-10828, 2003.
Schmidt et al., "Mucosal Immunization of Rhesus Monkeys against Respiratory Syncytial Virus Subgroups A and B and Human Parainfluenza Virus Type 3 by Using a Live cDNA-Derived Vaccine Based on a Host Range-Attenuated Bovine Parainfluenza Virus Type 3 Vector Backbone," Journal of Virology 76:1089-1099, 2002.
Greer et al., "A chimeric alphavirus RNA replicon gene-based vaccine for human parainfluenza virus type 3 induces protective immunity against intranasal virus challenge," Vaccine 25, 481-489, (2007).
Greer, et al., "Long-term Protection in Hamsters against Human Parainfluenza Virus Type 3 Following Mucosal or Combinations of Mucosal and Systemic Immunizations with Chimeric Alphavirus-based Replicon Particles," Scandinavian Journal of Immunology, vol. 66, 645-653, 2007.
Magini et al., "Self-Amplifying mRNA Vaccines Expressing Multiple Conserved Influenza Antigens Confer Protection against Homologous and Heterosubtypic Viral Challenge," PLOS One 11(8): e0161193.doi:10.1371/journal.phone.0161193 (2016).
Uematsu, et al., "Lack of Interference with Immunogenicity of a Chimeric Alphavirus Replicon Particle-Based Influenze Vaccine by Preexisting Antivector Immunity," Clinical and Vaccine Immunology, 19(7): 991-998 Jul. 2012.

\* cited by examiner

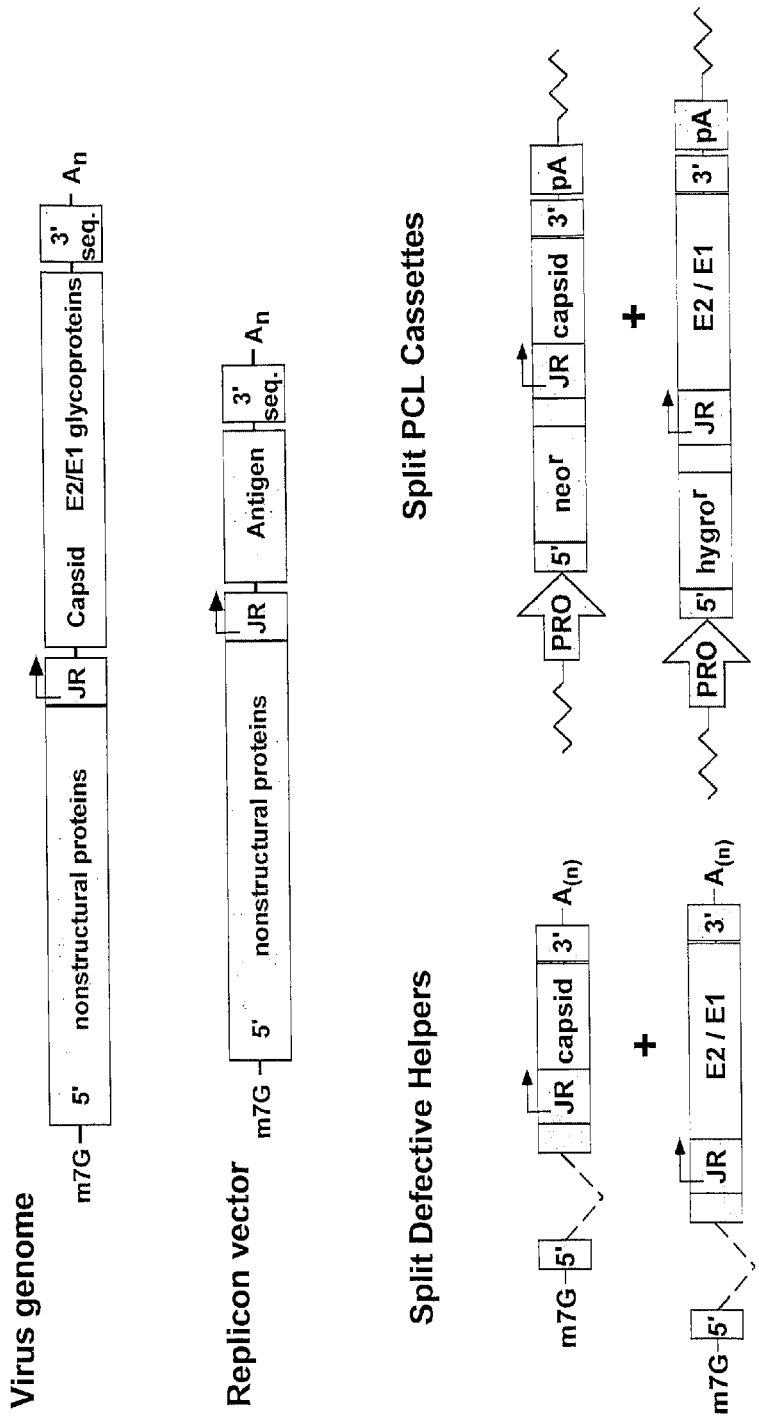
FIG. 1 Representative example configuration of alphavirus replicon and packaging components for production of replicon particles Fig. 2 Representative alphavirus replicon vectors encoding one or more influenza virus antigen(s)

Fig. 3 Representative alphavirus replicon vectors encoding one or more parainfluenza virus antigen(s)

Fig. 4 Representative alphavirus replicon vectors encoding one or more respiratory syncytial virus antigen(s)

Fig. 5 Representative alphavirus replicon vectors encoding antigen(s) from more than one respiratory virus pathogens

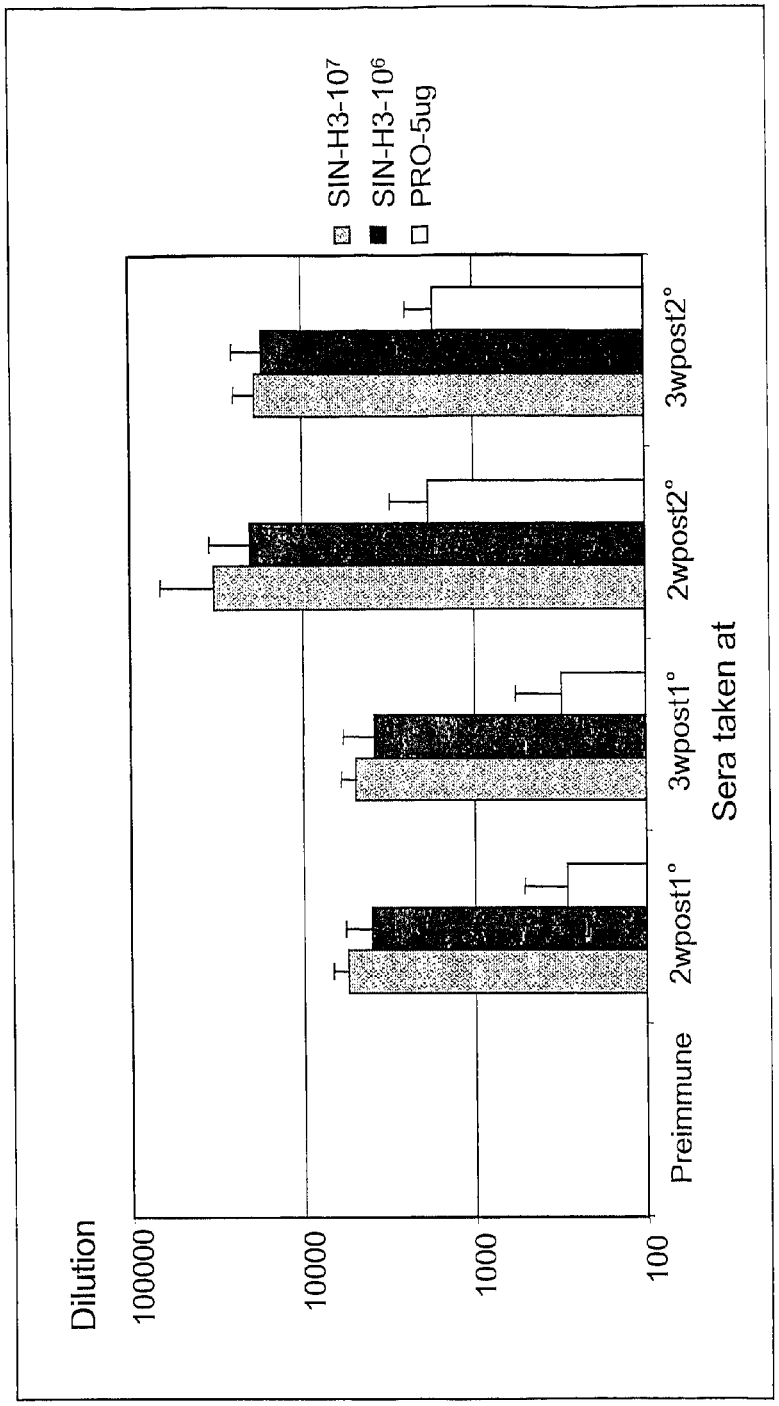
FIG. 6 Induction of higher FLU HA antibody responses immunizing with SIN-HA replicon particles as compared to HA subunit vaccine

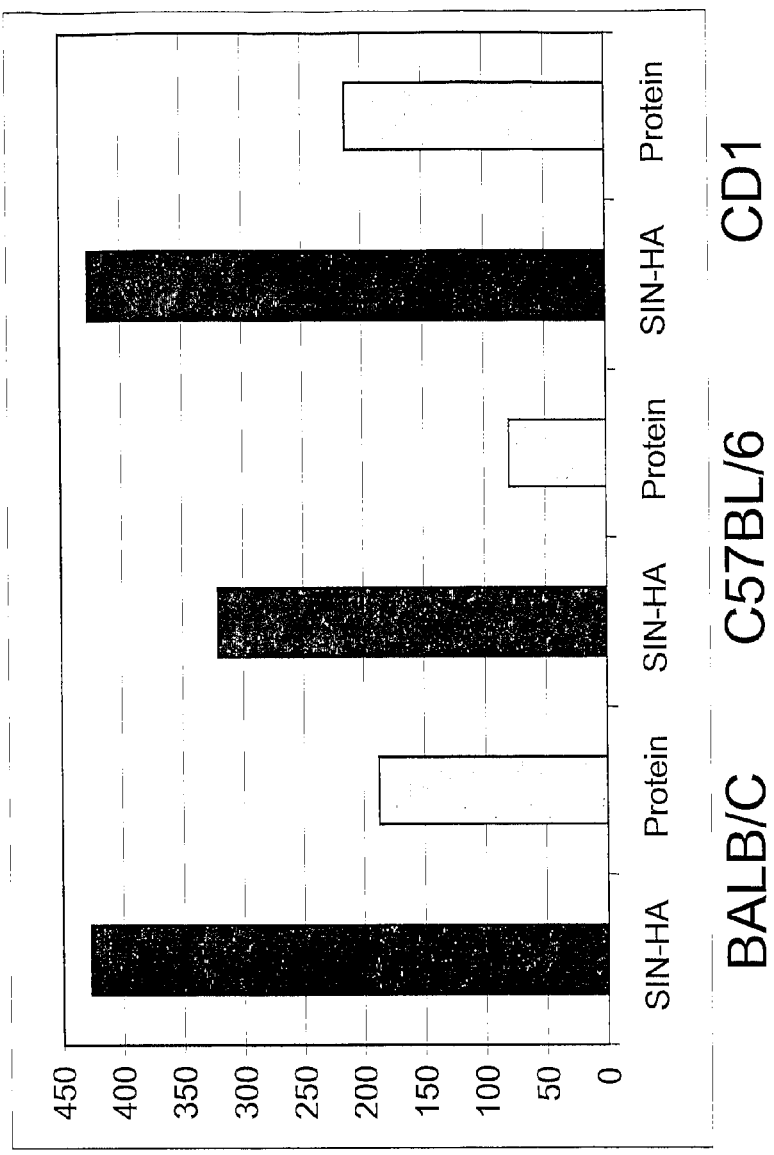
FIG. 7 Induction of higher level HI titers in mice following immunization with SIN-HA replicon particles as compared to HA subunit vaccine Fig. 8 Dose comparison in BALB/c mice of VEE/SIN chimera and SIN replicon particles expressing FLU HA protein Fig. 9 Protection of mice from FLU challenge following immunization with VEE/SIN replicon particles expressing either FLU NA or HA Figure 10. Induction of FLU HA-specific neutralizing antibodies in rhesus macaques immunized with VEE/SIN-FLU-HA particles

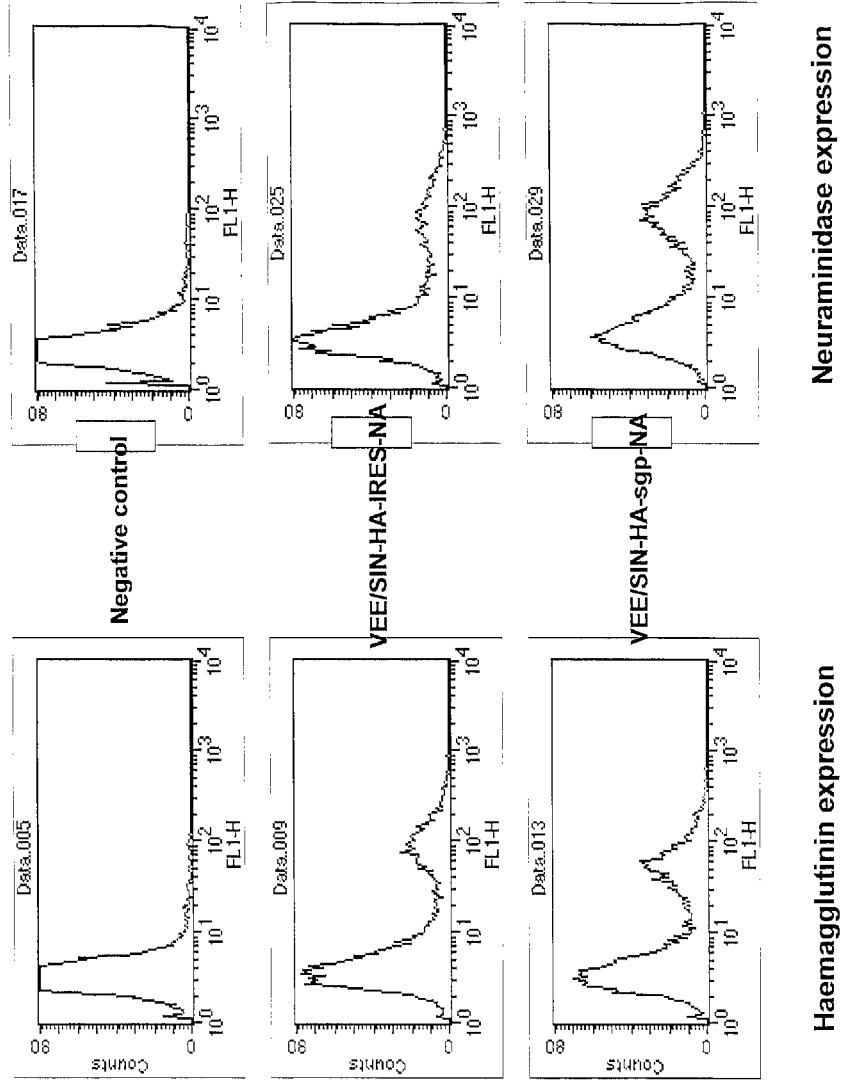
Figure 11. Expression of FLU HA and NA from bicistronic alphavirus replicon particles, using d Fig. 12 Induction of PIV specific antibody responses following immunization with alphavirus replicon particles expressing PIV HN

*IgG isotype titers shown as G1 (IgG1) or G2a (IgG2a) for each immunogen and route Figure 13. PIV specific serum antibody responses following immunization with various dosages of alphavirus replicon particles expressing PIV3 HN

* IgG1 and IgG2a isotype titer shown for each dosage of vaccine

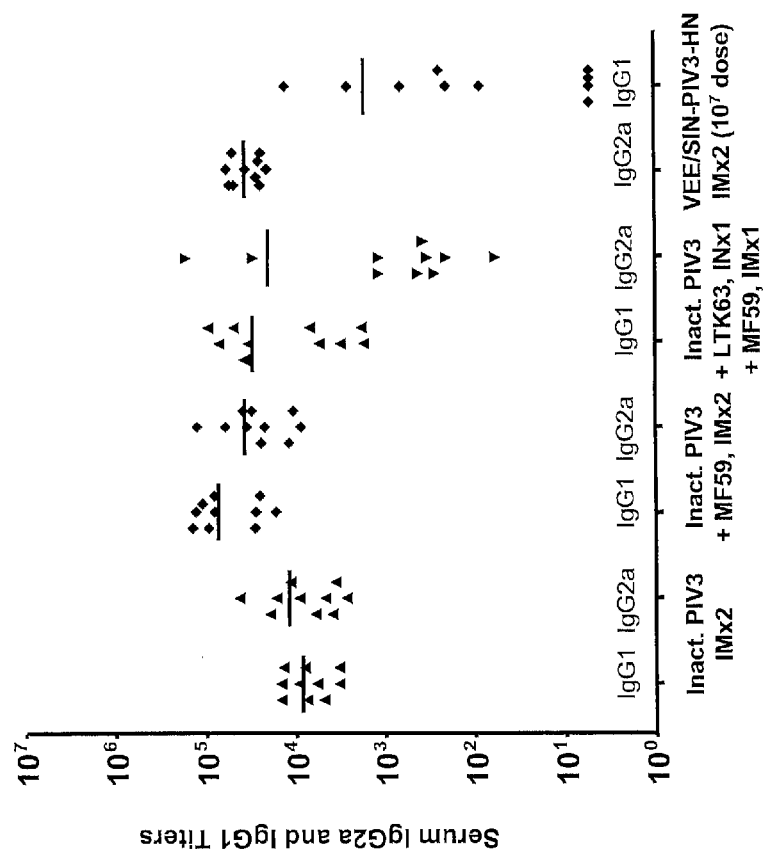
Figure 14. PIV specific serum antibody responses from inactivated PIV vaccines +/- adjuvants, administered by IM or IN routes
* IgG1 and IgG2a isotype titer shown for each vaccine modality

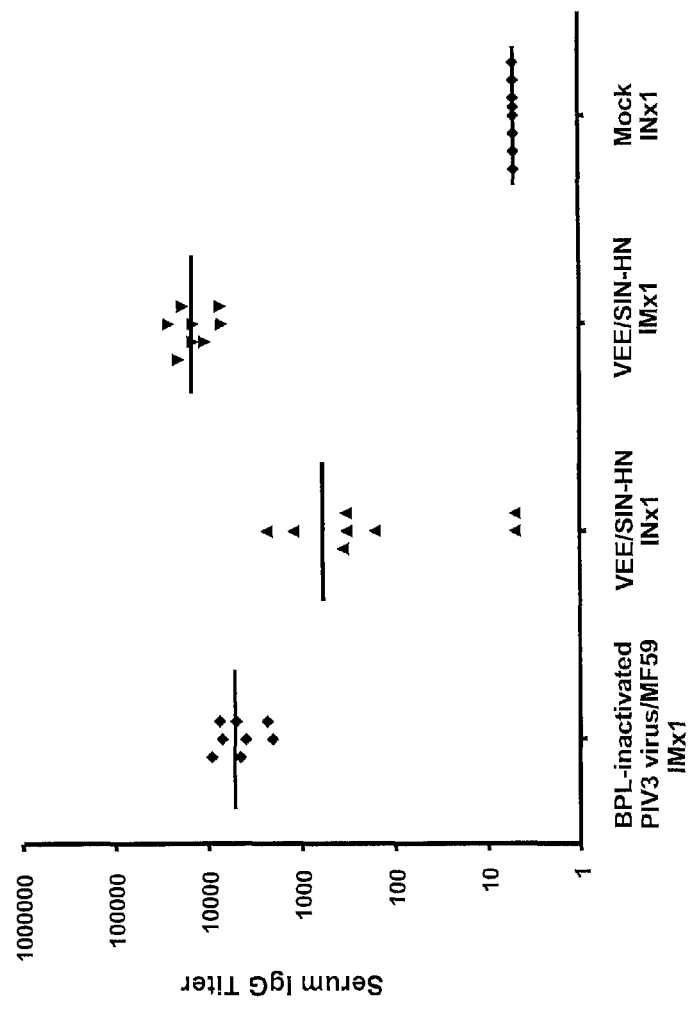
Figure 15. PIV specific serum IgG in hamsters 2 weeks post 1st immunization with VEE/SIN-PIV3

Figure 16. PIV3 specific serum IgG in hamsters 2 weeks post 2nd immunization with VEE/SIN-PIV3-HN particles or inactivated PIV3/MF59

Figure 17. VEE/SIN-HN replicon particle and MF59-adjuvanted inactivated PIV3 vaccines completely protect hamsters from intranasal PIV3 challenge

| Immunization | Route | Nasal Turbinates | | Lungs | |
|---|---|---|---|---|---|
| | | Mean Titer + SEM ($\log_{10}$ TCID$_{50}$/gm) | Reduction in Titer ($\log_{10}$) | Mean Titer + SEM ($\log_{10}$ TCID$_{50}$/gm) | Reduction in Titer ($\log_{10}$) |
| Mock | IN/IM | 5.3 + 0.2 | N/A | 4.5 + 0.4 | N/A |
| BPL-PIV3 + MF59 | IM/IM | <1.5 + 0.0 | >3.8 | <1.5 + 0.0 | >3.0 |
| VEE/SIN-HN | IM/IM | <1.5 + 0.0 | >3.8 | <1.5 + 0.0 | >3.0 |
| VEE/SIN-HN | IN/IM | <1.5 + 0.0 | >3.8 | <1.5 + 0.0 | >3.0 |

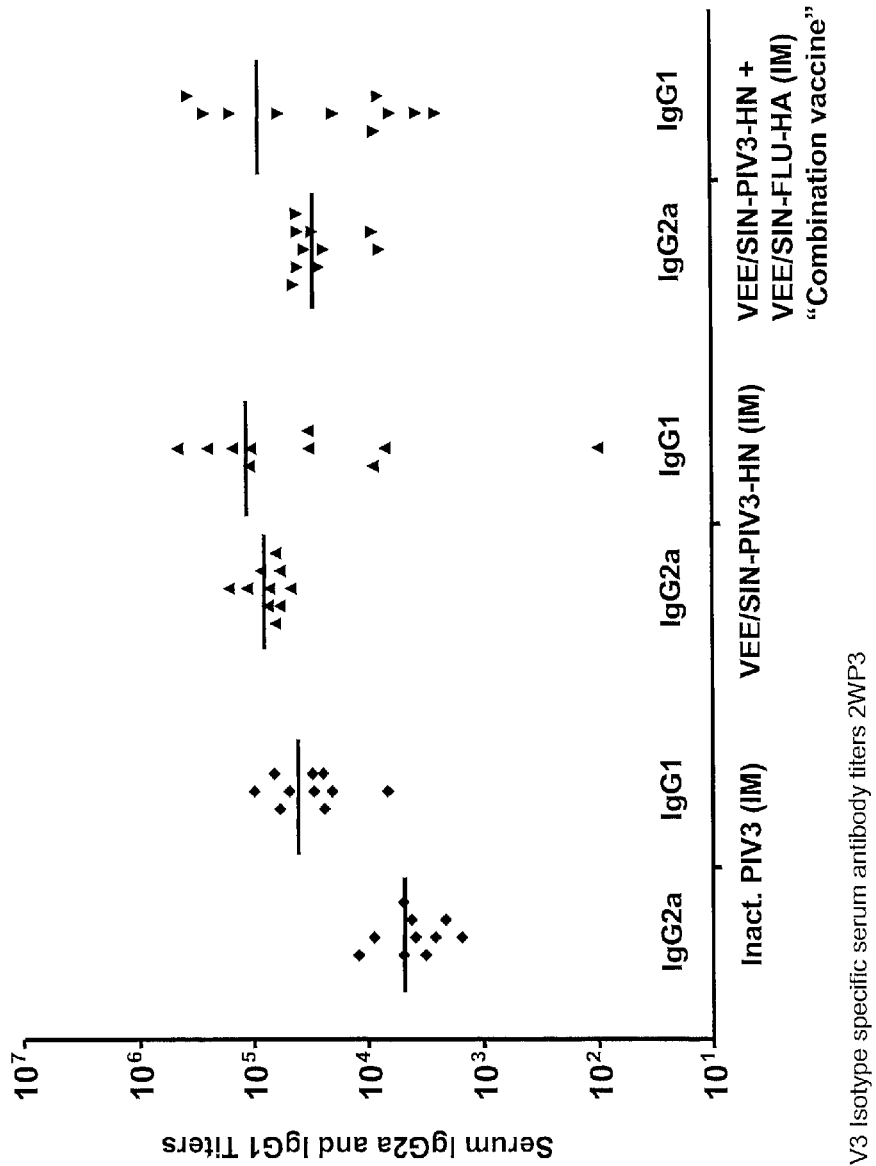
Figure 18. PIV specific serum antibody responses from inactivated PIV or alphavirus replicon particle PIV and PIV/FLU combination vaccines Figure 19. FLU specific serum antibody responses from alphavirus replicon particle FLU and PIV/FLU combination vaccines Anti-FLU Isotype specific serum antibody titers 2WP2

Figure 20. Immunization against SARS and FLU by sequential administration of VEE/SIN-SARS-Spike and VEE/SIN-FLU-HA replicon particles Figure 21. Low dosage alphavirus replicon particle vaccines expressing either HA or NA protect mice from intranasal FLU challenge Figure 22. Immunization with VEE/SIN replicon particles expressing FLU HA and/or NA provides protection from intranasal FLU challenge 100% protection
N1 and H1+N1 groups

- ♦ H1 only
- ■ N1 only
- ▲ H1 + N1

Percent survival vs Days after challenge $10^4$ IU replicon particle vaccine dose Figure 23. Immunization of hamsters with VEE/SIN-HN replicon particles by IM or IN routes provides complete protection from intranasal PIV3 challenge

B

| Vaccine | N | Mean virus titer ($\log_{10}$ TCID$_{50}$/g ± SEM) | |
|---|---|---|---|
| | | Nasal | Lung |
| VEE/SIN-HN 2x IM | 6 | <1.5 | <1.5 |
| VEE/SIN-HN 2x IN | 6 | <1.5 ± 0.8 | <1.5 |
| Mock Control | 6 | 6.0 ± 0.4 | 3.9 ± 0.7 |

Fig. 24B

Figure 25. PIV specific serum antibody responses from inactivated PIV or alphavirus replicon particle PIV and PIV/FLU combination vaccines Anti-PIV3 Isotype specific serum antibody titers 2WP2 x-axis: Naive | Inact. PIV3 IM x2 | VEE/SIN-PIV3-HN IM x2 | VEE/SIN-PIV3-HN + VEE/SIN-FLU-HA "Combination vaccine" IM x2 y-axis: Serum IgG2a and IgG1 Titers ($10^0$ to $10^7$)

SEQUENCE LISTING

<160> NUMBER OF SEQ ID NOS: 34

<210> SEQ ID NO 1
<211> LENGTH: 9
<212> TYPE: DNA
<213> ORGANISM: Artificial Sequence
<220> FEATURE:
<223> OTHER INFORMATION: Kozak sequence contained in the 5' primers

<400> SEQUENCE: 1 gccgccacc                                                                  9

<210> SEQ ID NO 2
<211> LENGTH: 39
<212> TYPE: DNA
<213> ORGANISM: Artificial Sequence
<220> FEATURE:
<223> OTHER INFORMATION: HA3F1 primer targeted to the H3 gene

<400> SEQUENCE: 2
gggtcgactg cagccgccac catgaagact atcattgct                                 39

<210> SEQ ID NO 3
<211> LENGTH: 39

```
<212> TYPE: DNA
<213> ORGANISM: Artificial Sequence
<220> FEATURE:
<223> OTHER INFORMATION: HA3R1 primer targeted to the H3 gene

<400> SEQUENCE: 3
gcatgcggcc gcatcgattc aaatgcaaat gttgcacct                      39

<210> SEQ ID NO 4
<211> LENGTH: 38
<212> TYPE: DNA
<213> ORGANISM: Artificial Sequence
<220> FEATURE:
<223> OTHER INFORMATION: NA2F1 primer targeted to N2 gene

<400> SEQUENCE: 4
gggtcgacag atctgccgcc accatgaatc caaatcaa                       38

<210> SEQ ID NO 5
<211> LENGTH: 39
<212> TYPE: DNA
<213> ORGANISM: Artificial Sequence
<220> FEATURE:
<223> OTHER INFORMATION: NA2R1 primer targeted to N2 gene

<400> SEQUENCE: 5
gcatgcggcc gcatcgatta tataggcatg agattgatg                      39

<210> SEQ ID NO 6
<211> LENGTH: 38
<212> TYPE: DNA
<213> ORGANISM: Artificial Sequence
<220> FEATURE:
<223> OTHER INFORMATION: HA1F1 primer targeted to H1 gene

<400> SEQUENCE: 6
gggtcgactg cagccgccac catgaaggca aaactact                       38

<210> SEQ ID NO 7
<211> LENGTH: 36
<212> TYPE: DNA
<213> ORGANISM: Artificial Sequence
<220> FEATURE:
<223> OTHER INFORMATION: HA1R1 primer targeted to H1 gene

<400> SEQUENCE: 7
gcatgcggcc gcatcgattc agatgcatat tctrca                         36

<210> SEQ ID NO 8
<211> LENGTH: 39
<212> TYPE: DNA
<213> ORGANISM: Artificial Sequence
<220> FEATURE:
<223> OTHER INFORMATION: NA1F1 primer targeted to N1 gene

<400> SEQUENCE: 8
gggtcgacag atctgccgcc accatgaatc caaaccara                      39

<210> SEQ ID NO 9
<211> LENGTH: 35
<212> TYPE: DNA
<213> ORGANISM: Artificial Sequence
<220> FEATURE:
<223> OTHER INFORMATION: NA1R1 primer targeted to N1 gene

<400> SEQUENCE: 9
```
gcatgcggcc gcatcgatct acttgtcaat gstga                                    35

<210> SEQ ID NO 10
<211> LENGTH: 42
<212> TYPE: DNA
<213> ORGANISM: Artificial Sequence
<220> FEATURE:
<223> OTHER INFORMATION: NPF1 primer targeted to WNP gene

<400> SEQUENCE: 10
gggtcgactc tagagccgcc accatggcgt cycaaggcac ca                            42

<210> SEQ ID NO 11
<211> LENGTH: 35
<212> TYPE: DNA
<213> ORGANISM: Artificial Sequence
<220> FEATURE:
<223> OTHER INFORMATION: NPR1 primer targeted to WNP gene

<400> SEQUENCE: 11
gcatgcggcc gcatcgatta attgtcgtay tcytc                                    35

<210> SEQ ID NO 12
<211> LENGTH: 44
<212> TYPE: DNA
<213> ORGANISM: Artificial Sequence
<220> FEATURE:
<223> OTHER INFORMATION: HA5F1 primer targeted to H5 gene

<400> SEQUENCE: 12
gcatggcgcg ccgtcgacgc caccatggar araayagtgc ttct                          44

<210> SEQ ID NO 13
<211> LENGTH: 34
<212> TYPE: DNA
<213> ORGANISM: Artificial Sequence
<220> FEATURE:
<223> OTHER INFORMATION: HA5R1 primer targeted to H5 gene

<400> SEQUENCE: 13
gcatgcggcc gcatcgatta aatgcaratt ctgc 34

<210> SEQ ID NO 14
<211> LENGTH: 41
<212> TYPE: DNA
<213> ORGANISM: Artificial Sequence
<220> FEATURE:
<223> OTHER INFORMATION: EMIRF2 primer targeted to IRES gene

<400> SEQUENCE: 14
tttggcgcgc catcgatgat atctgatttt ccaccatatt g 41

<210> SEQ ID NO 15
<211> LENGTH: 40
<212> TYPE: DNA
<213> ORGANISM: Artificial Sequence
<220> FEATURE:
<223> OTHER INFORMATION: EMIRR2 primer targeted to IRES gene

<400> SEQUENCE: 15
gcatgcggcc gcgtcgactt atcatcgtgt ttttcaaagg 40

<210> SEQ ID NO 16
<211> LENGTH: 40
<212> TYPE: DNA
<213> ORGANISM: Artificial Sequence

```
<220> FEATURE:
<223> OTHER INFORMATION: Oligonucleotide IN-F

<400> SEQUENCE: 16
atatatatat gcggccgctg gagggtttat tttgtgtgac                          40

<210> SEQ ID NO 17
<211> LENGTH: 32
<212> TYPE: DNA
<213> ORGANISM: Artificial Sequence
<220> FEATURE:
<223> OTHER INFORMATION: Oligonucleotide IN-R

<400> SEQUENCE: 17
atatatatat gtagcggcgg ccgcatcgat tc                                  32

<210> SEQ ID NO 18
<211> LENGTH: 79
<212> TYPE: DNA
<213> ORGANISM: Artificial Sequence
<220> FEATURE:
<223> OTHER INFORMATION: Oligonucleotide TM-F1

<400> SEQUENCE: 18
ctagaagaat caaaagaatg gataagaagg tcaaatcaaa aactagattc tattggaaat    60
tggcatcaat ctagcacta                                                79

<210> SEQ ID NO 19
<211> LENGTH: 88
<212> TYPE: DNA
<213> ORGANISM: Artificial Sequence
<220> FEATURE:
<223> OTHER INFORMATION: Oligonucleotide TM-R1

<400> SEQUENCE: 19
tagtacttaa ttgtagtgct agattgatgc caatttccaa tagaatctag tttttgattt    60
gaccttctta tccattcttt tgattctt                                      88

<210> SEQ ID NO 20
<211> LENGTH: 79
<212> TYPE: DNA
<213> ORGANISM: Artificial Sequence
<220> FEATURE:
<223> OTHER INFORMATION: Oligonucleotide TM-F2

<400> SEQUENCE: 20
ctagaagaat caaaagaatg gataagaagg tcaaatcaaa aactagattc tattggaaat    60
tggcatcaat ctagcacta                                                79

<210> SEQ ID NO 21
<211> LENGTH: 70
<212> TYPE: DNA
<213> ORGANISM: Artificial Sequence
<220> FEATURE:
<223> OTHER INFORMATION: Oligonucleotide TM-R2

<400> SEQUENCE: 21
ggccgcttat tgtttgtta gtacatatgg cttgtcattt tgatccactc gatttctctt    60
ttgaattctg                                                          70

<210> SEQ ID NO 22
<211> LENGTH: 33
<212> TYPE: DNA
```

```
<213> ORGANISM: Artificial Sequence
<220> FEATURE:
<223> OTHER INFORMATION: Oligonucleotide PIVf

<400> SEQUENCE: 22
atatatatat atacggcgcg ccaccatgcc aac                                    33

<210> SEQ ID NO 23
<211> LENGTH: 47
<212> TYPE: DNA
<213> ORGANISM: Artificial Sequence
<220> FEATURE:
<223> OTHER INFORMATION: Oligonucleotide PIVr

<400> SEQUENCE: 23
atatatatat gcggccgctt atgtagtgct agattgatgc caatttc                    47

<210> SEQ ID NO 24
<211> LENGTH: 43
<212> TYPE: DNA
<213> ORGANISM: Artificial Sequence
<220> FEATURE:
<223> OTHER INFORMATION: Oligonucleotide RSV-Gf

<400> SEQUENCE: 24
atatatatgg cgcgccccac catgtccaaa acaaggacc aac                          43

<210> SEQ ID NO 25
<211> LENGTH: 39
<212> TYPE: DNA
<213> ORGANISM: Artificial Sequence
<220> FEATURE:
<223> OTHER INFORMATION: Oligonucleotide RSV-Gr

<400> SEQUENCE: 25
atatatatat gcggccgcct actggcgtgg tgtgttggg                              39

<210> SEQ ID NO 26
<211> LENGTH: 44
<212> TYPE: DNA
<213> ORGANISM: Artificial Sequence
<220> FEATURE:
<223> OTHER INFORMATION: Oligonucleotide RSV-Ff

<400> SEQUENCE: 26
atatatatgg cgcgccccac catggagttg ctaatcctca aagc                       44

<210> SEQ ID NO 27
<211> LENGTH: 47
<212> TYPE: DNA
<213> ORGANISM: Artificial Sequence
<220> FEATURE:
<223> OTHER INFORMATION: Oligonucleotide RSV-Fr

<400> SEQUENCE: 27
atatatatat gcggccgctt agttactaaa tgcaatatta tttatac                    47

<210> SEQ ID NO 28
<211> LENGTH: 42
<212> TYPE: DNA
<213> ORGANISM: Artificial Sequence
<220> FEATURE:
<223> OTHER INFORMATION: Oligonucleotide HMPV-Gf

<400> SEQUENCE: 28
atatatatgg cgcgccccac catggaggtg aaagtggaga ac                         42
```

```
<210> SEQ ID NO 29
<211> LENGTH: 44
<212> TYPE: DNA
<213> ORGANISM: Artificial Sequence
<220> FEATURE:
<223> OTHER INFORMATION: Oligonucleotide HMPV-Gr

<400> SEQUENCE: 29
atatatatat gcggccgctt aactagtttg gttgtatgtt gttg              44

<210> SEQ ID NO 30
<211> LENGTH: 24
<212> TYPE: DNA
<213> ORGANISM: Artificial Sequence
<220> FEATURE:
<223> OTHER INFORMATION: Primer Sp-RT-R

<400> SEQUENCE: 30
ctcataaaca aatccataag ttcg                                    24

<210> SEQ ID NO 31
<211> LENGTH: 50
<212> TYPE: DNA
<213> ORGANISM: Artificial Sequence
<220> FEATURE:
<223> OTHER INFORMATION: Primer Sp-F-BbvCI

<400> SEQUENCE: 31
atatatatat cctcagccca ccatgtttat tttcttatta tttcttactc        50

<210> SEQ ID NO 32
<211> LENGTH: 41
<212> TYPE: DNA
<213> ORGANISM: Artificial Sequence
<220> FEATURE:
<223> OTHER INFORMATION: Primer Sp-R-NotI

<400> SEQUENCE: 32
atatatatgc ggccgcttat gtgtaatgta atttgacacc c                 41

<210> SEQ ID NO 33
<211> LENGTH: 40
<212> TYPE: DNA
<213> ORGANISM: Artificial Sequence
<220> FEATURE:
<223> OTHER INFORMATION: Primer SGP-forward

<400> SEQUENCE: 33
atatatatat gcggccgctg gagggtttat tttgtgtgac                   40

<210> SEQ ID NO 34
<211> LENGTH: 49
<212> TYPE: DNA
<213> ORGANISM: Artificial Sequence
<220> FEATURE:
<223> OTHER INFORMATION: Primer RSV F-reverse

<400> SEQUENCE: 34
atatatatat ccgcggccgc ttagttacta aatgcaatat tatttatac         49
```

ALPHAVIRUS VECTORS FOR RESPIRATORY PATHOGEN VACCINES

CROSS REFERENCE TO RELATED APPLICATIONS

This is a continuation application of U.S. application Ser. No. 12/791,140, filed on Jun. 1, 2010, which is a divisional application of U.S. application Ser. No. 11/597,347, filed Feb. 1, 2008 and now abandoned, which is the U.S. National Stage Entry of International Application No. PCT/US2005/018225, filed May 20, 2005 and published in English, which claims benefit of U.S. Provisional Application No. 60/573,433, filed May 21, 2004, and U.S. Provisional Application No. 60/643,737, filed Jan. 12, 2005. The teachings of the above applications are incorporated herein in their entirety by reference.

TECHNICAL FIELD

The present invention relates generally to compositions and methods for stimulating an immune response to respiratory pathogens. In particular, the invention relates to alphavirus replicons, alphavirus vector constructs, alphavirus replicon particles expressing one or more antigens derived from respiratory pathogens. The compositions described herein are useful for generating an immune response (e.g., prophylactic and/or therapeutic) against one or more respiratory pathogens.

BACKGROUND

Alphaviruses comprise a set of genetically, structurally, and serologically related arthropod-borne viruses of the Togaviridae family. At least twenty-six known viruses and virus subtypes have been classified within the alphavirus genus, including, Sindbis virus, Semliki Forest virus (SFV), Ross River virus (RR), and Venezuelan equine encephalitis (VEE) virus.

Sindbis virus is the prototype member of the Alphavirus genus of the Togaviridae family. Its replication strategy has been well characterized in a variety of cultured cells and serves as a model for other alphaviruses. Briefly, the genome of Sindbis (like other alphaviruses) is an approximately 12 kb single-stranded positive-sense RNA molecule that is capped, polyadenylated, and contained within a virus-encoded capsid protein shell. The nucleocapsid is further surrounded by a host-derived lipid envelope, into which two viral-specific glycoproteins, E1 and E2, are inserted and anchored by a cytoplasmic tail to the nucleocapsid. Certain alphaviruses (e.g., SFV) also maintain an additional protein, E3, which is a cleavage product of the E2 precursor protein, PE2.

After virus particle adsorption to target cells, penetration, and uncoating of the nucleocapsid to release viral genomic RNA into the cytoplasm, the replicative process is mediated by the four alphaviral nonstructural proteins (nsPs) and their precursors, translated from the 5' two-thirds of the viral genome. Synthesis of a full-length negative strand RNA, in turn, provides template for the synthesis of additional positive strand genomic RNA and an abundantly expressed 26S subgenomic RNA, initiated internally at the subgenomic junction region promoter. The alphavirus structural proteins are translated from the subgenomic 26S RNA, which represents the 3' one-third of the genome, and like the nsPs, are processed post-translationally into the individual proteins, capsid, E1 and E2 (pE2).

Among the respiratory virus pathogens, various approaches have been disclosed for utilizing alphavirus replicon vector based vaccines as a means to stimulate immune responses against respiratory viruses such as influenza (FLU), respiratory syncytial virus (RSV) and parainfluenza virus (PIV). More specifically, among the several studies related to FLU, each have focused exclusively on the use of replicon vectors expressing a single HA or single NP antigen (see Huckriede et al., 2004, Vaccine, 22:1104-13; Berglund et al., 1999, Vaccine 17:497-507; Berglund et al., 1998, Nat. Biotechnol. 16:562-565; Pushko et al., 1997, Virology 239:389-401; Zhou et al., 1995, PNAS 92:3009-3013; Vignuzzi et al., 2001, J. Gen. Virol. 82:1737-1747; Schultz-Cherry et al., 2000, Virology 278:55-59).

The use of alphavirus based strategies that incorporate genes encoding alternative FLU antigens other than HA or NP to stimulate an immune response, or alphavirus-based immunogenic compositions or vaccines that incorporate genes encoding more than one FLU antigen, have not been described. Thus, the need exists for improved alphavirus-based FLU vaccines that address these shortcomings.

As a vaccine strategy against RSV, alphavirus vectors expressing either the G or F antigens have been examined (U.S. Pat. Nos. 6,060,308A, 6,428,324B1, and 6,475,780B1; PCT applications WO9911808 and WO 9925858; Andersson et al., 2000, FEMS Immunol. Med. Micro. 29:247-253; Fleeton et al., 2001 J. Infect. Dis. 183:1395-1398). Similarly for PIV, vectors expressing either the HN or F antigens have been suggested (U.S. Pat. Nos. 6,060,308A, 6,428,324B1, and 6,475,780B1; PCT applications WO9911808 and WO 9925858). However, the use of alphavirus based strategies that incorporate alternative RSV or PIV antigens other than HN, G, or F to stimulate an immune response, or alphavirus-based immunogenic compositions or vaccines that combine multiple RSV and PIV antigens, have not been described.

There remains a need for compositions and methods of making and using alphavirus replicon vectors, vector constructs and replicon particles as a means to more effectively stimulate an immune response to respiratory pathogens such as viruses, bacteria and fungi, and for vaccines that comprise such alphavirus-based vectors. In addition, there remains a need for compositions and methods of making and using alphavirus replicon vectors and replicon particles in effective combination or as co-expression constructs, as a means to stimulate an immune response against more than one respiratory pathogen (e.g., combination immunogen or vaccine), and for vaccines that comprise such alphavirus-based replicons.

SUMMARY

Respiratory pathogens, such as respiratory viruses, bacteria and fungi, are suitable targets for alphavirus replicon vector-based vaccine approaches. Respiratory virus pathogens may include, for example, influenza virus (FLU), respiratory syncytial virus (RSV), parainfluenza virus (PIV), SARS coronavirus (SARS-CoV), human metapneumovirus (HMPV) and the like.

While the primary commercial application of such replicon-based approaches would be human prophylactic vaccines, the present invention also contemplates the use of analogous strategies for veterinary application, of which numerous animal respiratory virus pathogens from the above virus groups have been identified and characterized, such as for example in cows, horses, pigs, poultry, dogs and cats. Specific, non-limiting examples of respiratory virus pathogens in the veterinary field include influenza viruses, parainfluenza viruses, avian infectious bronchitis virus, bovine respiratory syncytial virus, porcine reproductive and respiratory syndrome virus, equine herpes virus, bovine rhinotracheitis virus, canine distemper virus, and feline calicivirus.

The present invention includes compositions comprising alphavirus replicon vectors, alphavirus vector constructs and alphavirus replicon particles encoding one or more heterologous polypeptides derived from a respiratory pathogen, and methods of making and using these replicon vectors, vector constructs and replicon particles. In certain embodiments, the alphavirus replicon vectors, vector constructs or particles comprise two or more heterologous sequences that encode combinations of proteins derived from one or more respiratory pathogens.

In one aspect, the alphavirus vector constructs or particles comprise a first heterologous nucleic acid encoding a protein derived from a respiratory pathogen. In certain embodiments, the respiratory pathogen comprises a virus, for example influenza (FLU) and the heterologous nucleic acid encodes a hemagglutin (HA) or neuroamidase (NA) protein.

In another aspect, the immunogenic compositions described herein comprise combinations of heterologous sequences, including, but not limited to, heterologous sequences encoding the same protein from different strains of the pathogen (e.g., FLU HA proteins from different strains, including strains that are causing or have the potential to cause pandemics); heterologous sequences encoding different proteins from the same pathogen (e.g., FLU H1 and H2 proteins or RSV G and F proteins); heterologous sequences encoding the same protein from different pathogens (e.g., FLU neuraminidase and PIV neuraminidase); and/or heterologous sequences encoding different proteins from different pathogens. It is to be understood that the combinations exemplified herein are exemplary only and that any combination of proteins can be used.

Furthermore, any number of alphavirus replicon vectors, vector constructs or particles can be used to carry one or more of the heterologous sequences. In certain embodiments, the heterologous sequences are included on the same alphavirus replicon vectors, vector constructs or particles. For example, one or more influenza antigens (e.g., NA and/or HA proteins) can be encoded by one alphavirus construct or particle as described herein. Where multiple antigens are includes, the antigens may be derived from multiple pandemic (or potentially pandemic viruses) and/or from interpandemic (also referred to as "annual") influenza strains. The compositions are useful in generating a protective and/or therapeutic immune response in a subject against a potential pandemic and/or to provide a vaccine effective against multiple strains. Because the compositions described herein include a broader range of antigens than traditional egg-based FLU vaccines (which are typically limited to 3 antigens and by the supply of egg), they may provide improved protection. Moreover, because the compositions described herein allow for a broader range of antigens to be included, they reduce or eliminate the need to reformulate flu vaccines annually, for example in response to antigenic shift. Increased potency, such as in elderly, young or immune compromised individuals also may be provided by compositions of the present invention.

In other embodiments, one or more heterologous sequences are included in separate alphavirus replicon vectors, vector constructs or particles (e.g., one or more heterologous sequences in a first alphavirus replicon vector, vector construct or particle and one or more heterologous sequences on a second alphavirus replicon vector, vector construct or particle).

Thus, it will be apparent that the ability of the compositions described herein to include multiple antigen proteins from one or more respiratory pathogens (e.g., multiple pandemic and/or interpandemic FLU antigens) allow for the generation of immune responses against a broader range of strains and pathogens than previously described. It will also be apparent that compositions described herein may be used in a variety of combinations, including, but not limited to, in priming administrations prior to boosting administrations with one or more additional immunogenic compositions.

In certain embodiments, the compositions described herein may be used as priming administrations and proteins used as boosting. The boosting proteins can include one or more of the proteins encoded by the heterologous sequences and/or additional proteins. For instance, compositions as described herein including heterologous sequences encoding multiple antigenic FLU proteins (pandemic and/or interpandemic) may be administered one or more times prior to administration of one or more FLU proteins (e.g., traditional 3-antigen FLU vaccines)

Alternatively, compositions described herein may be used in both priming and boosting. For instance, compositions as described herein including heterologous sequences encoding multiple antigenic FLU proteins from pandemic strains may be administered prior to compositions as described herein including heterologous sequences encoding multiple antigen FLU proteins from interpandemic strains.

In any of the embodiments described herein, more than one prime may be followed by more than one boost.

Accordingly, the invention includes, but is not limited to, the following numbered embodiments:

1. An immunogenic composition, comprising: (a) an alphavirus replicon vector, vector construct or replicon particle containing a heterologous nucleic acid encoding an influenza virus neuraminidase protein; and (b) a pharmaceutically acceptable carrier, diluent, or excipient.
2. The immunogenic composition according to embodiment 1, wherein said nucleic acid encoding a neuraminidase protein is derived from an influenza virus subtype selected from the group consisting of N1, N2, N3, N4, N5, N6, N7, N8, and N9.
3. The immunogenic composition according to embodiment 1, wherein said alphavirus replicon vector, vector construct or replicon particle further comprises a heterologous nucleic acid encoding an influenza virus hemagglutinin protein.
4. The immunogenic composition according to embodiment 3, wherein said nucleic acid encoding a hemagglutinin protein is derived from an influenza virus subtype selected from the group consisting of H1, H2 H3, H4, H5, H6, H7, H8, H9, H10, H11, H12, H13, H14, and H15.
5. The immunogenic composition according to embodiment 3, wherein said nucleic acid encoding a neuraminidase protein is operably linked to a first alphavirus subgenomic junction region promoter, and said nucleic acid encoding a hemagglutinin protein is operably linked to a second alphavirus subgenomic junction region promoter.
6. The immunogenic composition according to embodiment 3, wherein the heterologous nucleic acid further comprises a nucleic acid corresponding to an internal ribosome entry site (IRES).
7. An immunogenic composition, comprising: (a) an alphavirus replicon vector, vector construct or replicon particle containing a first heterologous nucleic acid encoding a parainfluenza virus hemagglutinin-neuraminidase protein and a second heterologous nucleic acid encoding a parainfluenza virus fusion protein; and (b) a pharmaceutically acceptable carrier, diluent, or excipient.

8. The immunogenic composition according to embodiment 7, wherein said nucleic acid encoding a hemagglutinin-neuraminidase protein is operably linked to a first alphavirus subgenomic junction region promoter, and said nucleic acid encoding a fusion protein is operably linked to a second alphavirus subgenomic junction region promoter.

9. The immunogenic composition according to embodiment 7, wherein the nucleic acid further comprises a nucleic acid corresponding to an internal ribosome entry site (IRES).

10. An immunogenic composition, comprising: (a) an alphavirus replicon vector, vector construct or replicon particle containing a first heterologous nucleic acid encoding a respiratory syncytial virus glycoprotein G and a second heterologous nucleic acid encoding a respiratory syncytial virus fusion protein, wherein said first and second heterologous nucleic acids are separated by an internal ribosome entry site (IRES); and (b) a pharmaceutically acceptable carrier, diluent, or excipient.

11. An immunogenic composition, comprising: (a) an alphavirus replicon vector, vector construct or replicon particle containing a heterologous nucleic acid encoding a human metapneumovirus glycoprotein; and (b) a pharmaceutically acceptable carrier, diluent, or excipient.

12. An immunogenic composition, comprising: (a) an alphavirus replicon vector, vector construct or replicon particle containing a first heterologous nucleic acid encoding an influenza virus protein and a second heterologous nucleic acid encoding a protein selected from the group consisting of a SARS coronavirus protein, a respiratory syncytial virus protein, a parainfluenza virus protein and a human metapneumovirus protein; and (b) a pharmaceutically acceptable carrier, diluent, or excipient.

13. The immunogenic composition of embodiment 12, wherein said second heterologous nucleic acid encodes a SARS coronavirus protein.

14. An immunogenic composition, comprising: (a) an alphavirus replicon vector, vector construct or replicon particle containing a first heterologous nucleic acid encoding a parainfluenza virus protein and a second heterologous nucleic acid encoding a protein selected from the group consisting of a respiratory syncytial virus protein, a SARS coronavirus protein and a human metapneumovirus protein; and (b) a pharmaceutically acceptable carrier, diluent, or excipient.

15. The immunogenic composition of embodiment 14, wherein said second heterologous nucleic acid encodes a respiratory syncytial virus protein.

16. An immunogenic composition, comprising: (a) an alphavirus replicon vector, vector construct or replicon particle containing a first heterologous nucleic acid encoding a respiratory syncytial virus protein and a second heterologous nucleic acid encoding a protein selected from the group consisting of a human metapneumovirus protein, a parainfluenza virus protein and a SARS coronavirus protein; and (b) a pharmaceutically acceptable carrier, diluent, or excipient.

17. The immunogenic composition of embodiment 16, wherein said second heterologous nucleic acid encodes a human metapneumovirus protein.

18. An immunogenic composition, comprising: (a) a first alphavirus replicon vector, vector construct or replicon particle containing a heterologous nucleic acid encoding an influenza virus protein; (b) a second alphavirus replicon vector, vector construct or replicon particle containing a heterologous nucleic acid encoding a protein selected from the group consisting of a SARS coronavirus protein, a respiratory syncytial virus protein, a parainfluenza virus protein and a human metapneumovirus protein; and (c) a pharmaceutically acceptable carrier, diluent, or excipient.

19. The immunogenic composition of embodiment 18, wherein said second alphavirus replicon vector, vector construct or replicon particle encodes a SARS coronavirus protein.

20. An immunogenic composition, comprising: (a) a first alphavirus replicon vector, vector construct or replicon particle containing a heterologous nucleic acid encoding parainfluenza virus protein; (b) a second alphavirus replicon vector, vector construct or replicon particle containing a heterologous nucleic acid encoding a protein selected from the group consisting of a respiratory syncytial virus proteins, a SARS coronavirus protein and a human metapneumovirus protein; and (c) a pharmaceutically acceptable carrier, diluent, or excipient.

21. The immunogenic composition of embodiment 20, wherein said second alphavirus replicon vector, vector construct or replicon particle encodes a respiratory syncytial virus protein.

22. An immunogenic composition, comprising: (a) a first alphavirus replicon vector, vector construct or replicon particle containing a heterologous nucleic acid encoding a respiratory syncytial virus protein; (b) a second alphavirus replicon vector, vector construct or replicon particle containing a heterologous nucleic acid encoding a protein selected from the group consisting of a human metapneumovirus protein, a parainfluenza virus protein and a SARS coronavirus protein; and (c) a pharmaceutically acceptable carrier, diluent, or excipient.

23. The immunogenic composition of embodiment 22, wherein said second alphavirus replicon vector, vector construct or replicon particle encodes a human metapneumovirus protein.

24. An immunogenic composition, comprising: (a) a first alphavirus replicon vector, vector construct or replicon particle containing a first heterologous nucleic acid encoding an influenza virus protein; (b) a second alphavirus replicon vector, vector construct or replicon particle containing a second heterologous nucleic acid encoding an influenza virus protein, wherein said second heterologous nucleic acid is different from said first heterologous nucleic acid; and (c) a pharmaceutically acceptable carrier, diluent, or excipient.

25. An immunogenic composition, comprising: (a) a first alphavirus replicon vector, vector construct or replicon particle containing a first heterologous nucleic acid encoding a parainfluenza virus protein; (b) a second alphavirus replicon vector, vector construct or replicon particle containing a second heterologous nucleic acid encoding a parainfluenza virus protein, wherein said second heterologous nucleic acid is different from said first heterologous nucleic acid; and (c) a pharmaceutically acceptable carrier, diluent, or excipient.

26. An immunogenic composition, comprising: (a) a first alphavirus replicon vector, vector construct or replicon particle containing a first heterologous nucleic acid encoding and respiratory syncytial virus protein; (b) a second alphavirus replicon vector, vector construct or replicon particle containing a second heterologous nucleic acid encoding a respiratory syncytial virus protein, wherein said second heterologous nucleic acid is different from said first heterologous nucleic acid; and (c) a pharmaceutically acceptable carrier, diluent, or excipient.

27. An immunogenic composition, comprising: (a) a first alphavirus replicon vector, vector construct or replicon particle containing a first heterologous nucleic acid encoding a SARS coronavirus protein; (b) a second alphavirus replicon vector, vector construct or replicon particle containing a second heterologous nucleic acid encoding a SARS coronavirus protein, wherein said second heterologous nucleic acid is different from said first heterologous nucleic acid; and (c) a pharmaceutically acceptable carrier, diluent, or excipient.

28. An immunogenic composition, comprising: (a) a first alphavirus replicon vector, vector construct or replicon particle containing a first heterologous nucleic acid encoding a human metapneumovirus protein; (b) a second alphavirus replicon vector, vector construct or replicon particle containing a second heterologous nucleic acid encoding a human metapneumovirus protein, wherein said second heterologous nucleic acid is different from said first heterologous nucleic acid; and (c) a pharmaceutically acceptable carrier, diluent, or excipient.

29. An immunogenic composition, comprising: (a) an alphavirus replicon vector, vector construct or replicon particle containing a first heterologous nucleic acid encoding an influenza virus protein and a second heterologous nucleic acid encoding an influenza virus protein, wherein said second heterologous nucleic acid is different from said first heterologous nucleic acid; and (b) a pharmaceutically acceptable carrier, diluent, or excipient.

30. An immunogenic composition according to any of embodiments 1-29 further comprising an adjuvant.

31. The immunogenic composition according to any of embodiments 12, 18, 24 and 29, wherein said nucleic acid encoding an influenza virus protein is selected from the group consisting of a sequence encoding a hemagglutinin protein, a sequence encoding a neuraminidase protein, a sequence encoding a nucleocapsid protein, and a sequence encoding a matrix protein.

32. The immunogenic composition according to any of embodiments 12, 13, 14, 16, 18, 19, 20, 22, and 27, wherein said nucleic acid encoding a SARS coronavirus protein is selected from the group consisting of a nucleic acid encoding a spike protein, a nucleic acid encoding an envelope protein, a nucleic acid encoding a nucleocapsid protein, and a nucleic acid encoding a matrix protein.

33. The immunogenic composition according to any of embodiments 12, 14, 16, 17, 18, 20, 22, 23, and 28, wherein said nucleic acid encoding a human metapneumovirus protein is selected from the group consisting of a nucleic acid encoding a glycoprotein G, a nucleic acid encoding a fusion protein, a nucleic acid encoding a nucleocapsid protein, and a nucleic acid encoding a matrix protein.

34. The immunogenic composition according to any of embodiments 12, 14, 16, 18, 20, 22, and 25, wherein said nucleic acid encoding a parainfluenza virus protein is selected from the group consisting of a nucleic acid encoding a hemagglutinin-neuraminidase protein, a nucleic acid encoding a fusion protein, a nucleic acid encoding a nucleocapsid protein, and a nucleic acid encoding a matrix protein.

35. The immunogenic composition according to any of embodiments 12, 14, 15, 16, 18, 20, 21, 22 and 26, wherein said nucleic acid encoding a respiratory syncytial virus protein is selected from the group consisting of a nucleic acid encoding a glycoprotein G, a nucleic acid encoding a fusion protein, a nucleic acid encoding a nucleocapsid protein, and a nucleic acid encoding a matrix protein.

36. The immunogenic composition according to any of embodiments 1-29, wherein said alphavirus replicon vector, vector construct and replicon particle is derived from one or more alphaviruses selected from the group consisting of a Sindbis virus, a Semliki Forest virus, a Venezuelan equine encephalitis virus, and a Ross River virus.

37. The immunogenic composition according to any of embodiments 1-29, wherein said immunogenic composition is lyophilized.

38. A method of stimulating an immune response in a mammal, the method comprising administering an immunogenic composition according to embodiments 1-30 to said mammal, thereby generating an immune response.

39. The method of stimulating an immune response according to embodiment 38, further comprising a second step of administering a second immunogenic composition, wherein said second immunogenic composition comprises: (a) a protein, polypeptide or portion thereof, derived from substantially the same source as the heterologous nucleic acid(s); and (b) a pharmaceutically acceptable carrier, diluent, or excipient.

40. The method according to embodiment 39, wherein said second step of administering a second immunogenic composition, further comprises administering an adjuvant.

41. The method according to embodiment 38, wherein said immunogenic composition is administered by a route selected from the group consisting of intramuscular, intranasal, subcutaneous, intradermal, intratracheal, and oral.

42. The method of stimulating an immune response according to embodiment 38, further comprising a second step of administering a second immunogenic composition, wherein said second immunogenic composition comprises: (a) a non-alphavirus derived viral vector encoding a protein, polypeptide or portion thereof, derived from substantially the same source as the heterologous nucleic acid(s); and (b) a pharmaceutically acceptable carrier, diluent, or excipient.

43. The method of stimulating an immune response according to embodiment 38, further comprising a second step of administering a second immunogenic composition, wherein said second immunogenic composition comprises: (a) an attenuated virus encoding a protein, polypeptide or portion thereof, derived from substantially the same source as the heterologous nucleic acid(s); and (b) a pharmaceutically acceptable carrier, diluent, or excipient.

44. A vaccine comprising an immunogenic composition as in any of embodiments 1-37.

45. An immunogenic composition, comprising: (a) a preparation of substantially purified, inactivated parainfluenza virus; (b) a pharmaceutically acceptable carrier, diluent, or excipient; and (c) an adjuvant.

46. The immunogenic composition according to embodiment 45, wherein said adjuvant is selected from the group consisting of MF59, LTK63 and alum.

47. A parainfluenza virus vaccine comprising: (a) a preparation of substantially purified, inactivated parainfluenza virus; (b) a pharmaceutically acceptable carrier, diluent, or excipient; and (c) an adjuvant.

48. The vaccine according to embodiment 45, wherein said adjuvant is selected from the group consisting of MF59, LTK63 and alum.
49. A method of stimulating an immune response in a mammal, the method comprising administering an immunogenic composition according to embodiment 45 or a vaccine according to embodiment 47 to said mammal, thereby generating an immune response.
50. The method according to embodiment 49, wherein said immunogenic composition or vaccine is administered by a route selected from the group consisting of intramuscular, intranasal, subcutaneous, intradermal, intratracheal, and oral.

These and other aspects and embodiments of the invention will become evident upon reference to the following detailed description, attached figures and various references set forth herein that describe in more detail certain procedures or compositions (e.g., plasmids, sequences, etc.).

BRIEF DESCRIPTION OF THE FIGURES

FIG. 1 is a schematic illustration depicting the general configuration of representative alphavirus replicon vectors and packaging components used to generate alphavirus replicon particles.

FIG. 2 is a schematic illustration of representative alphavirus replicon vectors encoding one or more influenza virus antigens.

FIG. 3 is a schematic illustration of representative alphavirus replicon vectors encoding one or more parainfluenza virus antigens.

FIG. 4 is a schematic illustration of representative alphavirus replicon vectors encoding one or more respiratory syncytial virus antigens.

FIG. 5 is a schematic illustration of representative alphavirus replicon vectors encoding antigens selected from at least two different respiratory virus pathogens.

FIG. 6 is a graph showing FLU HA specific antibody titers in mice immunized with alphavirus replicon particles as compared to conventional HA subunit vaccine antigen.

FIG. 7 is a graph showing FLU specific neutralizing antibodies (determined as HI titers) in mice immunized with alphavirus replicon particles as compared to HA subunit vaccine antigen.

FIG. 8 is a graph comparing the immunogenicity of various doses of SIN and VEE/SIN replicon particles expressing FLU HA antigen.

FIG. 9 is a graph showing protection of mice from intranasal FLU virus challenge after immunization with alphavirus replicon particles expressing either FLU HA or NA.

FIG. 10 is a graph showing the induction of FLU neutralizing antibodies in rhesus macaques immunized with VEE/SIN replicon particles expressing FLU HA antigen.

FIG. 11 is a graph showing the dual expression of FLU HA and NA from bicistronic VEE/SIN replicon particles, using either duplicated subgenomic promoters or an IRES element.

FIG. 12 is a graph showing the induction of PIV specific antibody responses in mice immunized IM, IN or IN followed by IM with replicon particles expressing PIV HN antigen.

FIG. 13 is a graph showing induction of PIV antibody responses in mice immunized with decreasing dosages of alphavirus replicon particles expressing HN FIG. 14 is a graph showing the induction of PIV specific antibody in mice. immunized with an inactivated PIV vaccine with or without adjuvant (MF59 or LTK63), and administered LM or IN followed by IM.

FIG. 15 is a graph demonstrating the induction of PIV antibody responses in hamsters immunized once with VEE/SIN replicon particles expressing HN or an inactivated PIV vaccine with MF59 adjuvant.

FIG. 16 is a graph demonstrating the induction of PIV antibody responses in hamsters immunized twice with VEE/SIN replicon particles expressing HN or an inactivated PIV vaccine with MF59 adjuvant.

FIG. 17 is a table demonstrating the protection of hamsters from intranasal PIV challenge following immunization with VEE/SIN replicon particles expressing HN antigen or an inactivated vaccine with MF59 adjuvant.

FIG. 18 is a graph showing the induction of PIV specific antibody responses following immunization with an alphavirus replicon particle based PIV/FLU combination vaccine.

FIG. 19 is a graph showing the induction of FLU specific antibody responses following immunization with an alphavirus replicon particle based PIV/FLU combination vaccine.

FIG. 20 is a graph showing the induction of SARS and FLU specific antibody responses in mice immunized sequentially with alphavirus replicon particles expressing SARS S protein and alphavirus replicon particles expressing FLU HA protein.

FIG. 21, panels A and B, are graphs showing protection of mice from intranasal FLU virus challenge after immunization with low dosage amounts of alphavirus replicon particles expressing either FLU HA or NA.

FIG. 22 is a graph depicting protection of mice from intranasal FLU virus challenge after immunization with an alphavirus replicon particle vaccine preparation that expresses both HA and NA antigens.

FIG. 23A is a graph depicting the immunogenicity in hamsters of an alphavirus replicon particle vaccine expressing PIV3 HN antigen administered either IM or IN and the resulting complete protection of these vaccinated animals from intranasal challenge with PIV3 virus.

FIG. 23B is a table depicting the results shown in the graph of FIG. 23A.

FIGS. 24A-B are graphs depicting the dual expression of PIV3 HN (right columns) and RSV F (left columns) from bicistronic alphavirus replicon particles (FIG. 24B) and from a combination of replicon particles separately expressing PIV HN and RSV F (FIG. 24A).

FIG. 25 is a graph showing the induction of PIV specific antibody responses following immunization with an alphavirus replicon particle based PIV/FLU combination vaccine.

DETAILED DESCRIPTION

Figure 24A:
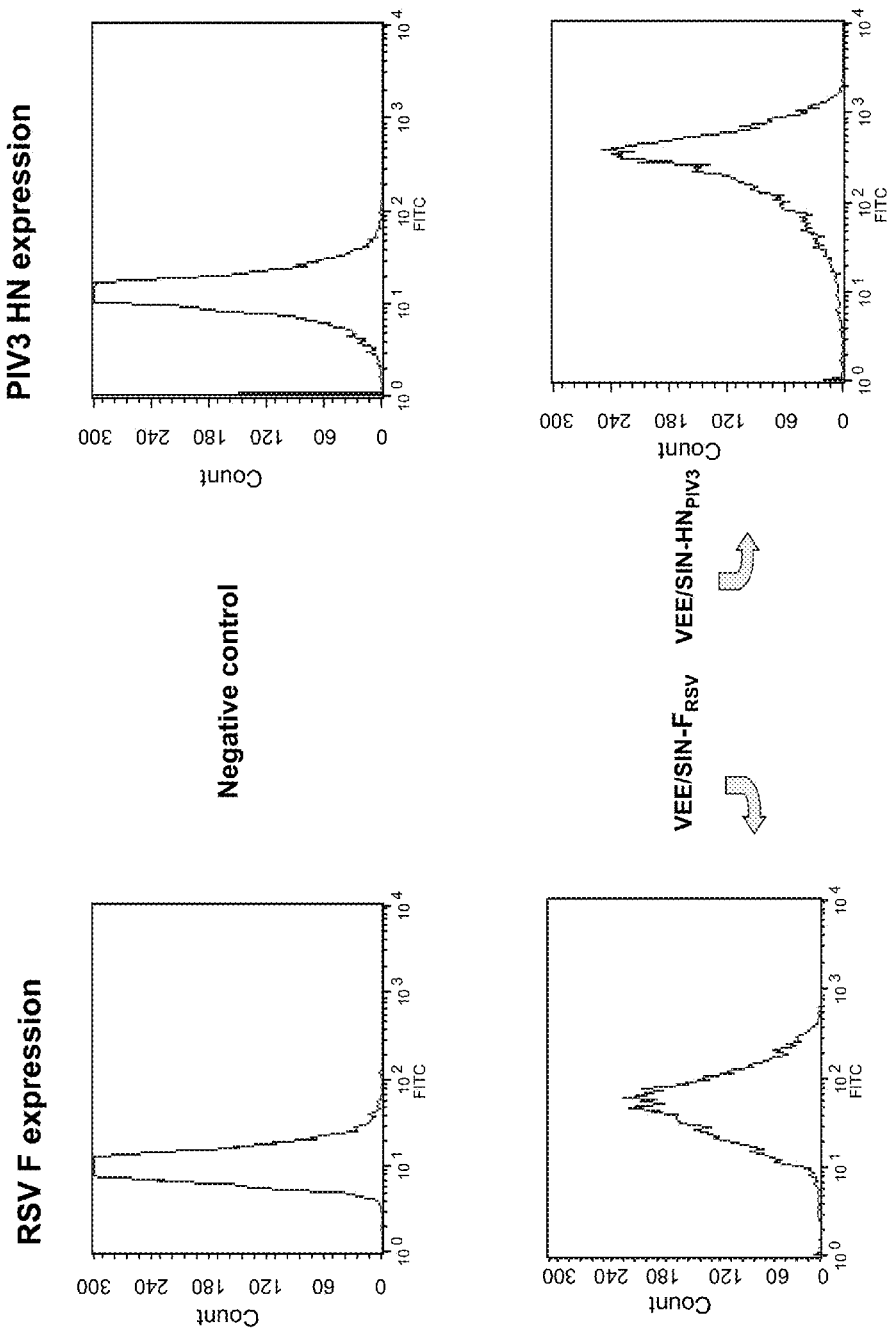

The invention relates to immunogenic compositions comprising an alphavirus replicon vector, an alphavirus vector construct or an alphavirus replicon particle comprising at least one heterologous nucleic acid encoding a respiratory pathogen. The immunogenic compositions (e.g., vaccines) are useful in generating an immune response when administered to a subject.

The practice of the present invention will employ, unless otherwise indicated, conventional methods of chemistry, biochemistry, molecular biology, immunology and pharmacology, within the skill of the art. Such techniques are explained fully in the literature. See, e.g., *Remington's Pharmaceutical Sciences*, 18th Edition (Easton, Pa.: Mack Publishing Company, 1990); *Methods In Enzymology* (S. Colowick and N. Kaplan, eds., Academic Press, Inc.); and *Handbook of Experimental Immunology*, Vols. I-IV (D. M. Weir and C. C. Blackwell, eds., 1986, Blackwell Scientific Publications); Sambrook, et al., *Molecular Cloning: A Laboratory Manual* (2nd Edition, 1989); *Handbook of Surface and Colloidal Chemistry* (Birdi, K. S. ed., CRC Press, 1997); *Short Protocols in Molecular Biology*, 4th ed. (Ausubel et al. eds., 1999, John Wiley & Sons); *Molecular Biology Techniques: An Intensive Laboratory Course*, (Ream et al., eds., 1998, Academic Press); *PCR (Introduction to Biotechniques Series)*, 2nd ed. (Newton & Graham eds., 1997, Springer Verlag); Peters and Dalrymple, *Fields Virology* (2d ed), Fields et al. (eds.), B.N. Raven Press, New York, N.Y.

All publications, patents and patent applications cited herein, whether supra or infra, are hereby incorporated by reference in their entirety.

As used in this specification, the singular forms "a," "an" and "the" include plural references unless the content clearly dictates otherwise. Thus, for example, reference to "a particle" includes a mixture of two or more such particles.

Prior to setting forth the invention definitions of certain terms that will be used hereinafter are set forth.

A "nucleic acid" molecule can include, but is not limited to, prokaryotic sequences, eukaryotic mRNA or other RNA, cDNA from eukaryotic mRNA or other RNA, genomic DNA sequences from eukaryotic (e.g., mammalian) DNA, and even synthetic DNA sequences. The term also captures sequences that include any of the known base analogs of DNA and RNA and includes modifications such as deletions, additions and substitutions (generally conservative in nature), to the native sequence. These modifications may be deliberate, as through site-directed mutagenesis, or may be accidental. Modifications of polynucleotides may have any number of effects including, for example, facilitating expression of the polypeptide product in a host cell.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein that includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts that produce the proteins or errors due to PCR amplification. Furthermore, modifications may be made that have one or more of the following effects: reducing toxicity; facilitating cell processing (e.g., secretion, antigen presentation, etc.); and facilitating presentation to B-cells and/or T-cells. The terms "polypeptide," and "protein" are used interchangeably herein to denote any polymer of amino acid residues. The terms encompass peptides, oligopeptides, dimers, multimers, and the like. Such polypeptides can be derived from natural sources or can be synthesized or recombinantly produced. The terms also include postexpression modifications of the polypeptide, for example, glycosylation, acetylation, phosphorylation, etc.

A polypeptide as defined herein is generally made up of the 20 natural amino acids Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y) and Val (V) and may also include any of the several known amino acid analogs, both naturally occurring and synthesized analogs, such as but not limited to homoisoleucine, asaleucine, 2-(methylenecyclopropyl)glycine, S-methylcysteine, S-(prop-1-enyl)cysteine, homoserine, ornithine, norleucine, norvaline, homoarginine, 3-(3-carboxyphenyl)alanine, cyclohexylalanine, mimosine, pipecolic acid, 4-methylglutamic acid, canavanine, 2,3-diaminopropionic acid, and the like. Further examples of polypeptide agents that will find use in the present invention are set forth below.

By "wild type" polypeptide, polypeptide agent or polypeptide drug, is meant a naturally occurring polypeptide sequence (and, optionally, its corresponding secondary structure). An "isolated" or "purified" protein or polypeptide is a protein that is separate and discrete from a whole organism with which the protein is normally associated in nature. It is apparent that the term denotes proteins of various levels of purity. Typically, a composition containing a purified protein will be one in which at least about 35%, preferably at least about 40-50%, more preferably, at least about 75-85%, and most preferably at least about 90% or more, of the total protein in the composition will be the protein in question.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

Techniques for determining amino acid sequence "similarity" are well known in the art. In general, "similarity" means the exact amino acid-to-amino acid comparison of two or more polypeptides at the appropriate place, where amino acids are identical or possess similar chemical and/or physical properties such as charge or hydrophobicity. A so-termed "percent similarity" then can be determined between the compared polypeptide sequences.

Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide-to-nucleotide or amino acid-to-amino acid correspondence of two polynucleotides or polypeptide sequences, respectively.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358S, National Biomedical Research Foundation, Washington, D.C., USA, and normalized by Gribskov, Nucl. Acids Res. 14(6):6745-6763 (1986). An implementation of this algorithm for nucleic acid and peptide sequences is provided by the Genetics Computer Group (Madison, Wis.) in their BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

For example, percent identity of a particular nucleotide sequence to a reference sequence can be determined using the homology algorithm of Smith and Waterman with a default scoring table and a gap penalty of six nucleotide positions. Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated, the "Match" value reflects "sequence identity." Other suitable programs for calculating the percent identity or similarity between sequences are generally known in the art, such as the alignment program BLAST, which can also be used with default parameters. For example, BLASTN and BLASTP can be used with the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following interne address: http://www.ncbi.nlm.gov/cgi-bin/BLAST.

One of skill in the art can readily determine the proper search parameters to use for a given sequence in the above programs. For example, the search parameters may vary based on the size of the sequence in question. Thus, for example, a representative embodiment of the present invention would include an isolated polynucleotide having X contiguous nucleotides, wherein (i) the X contiguous nucleotides have at least about 50% identity to Y contiguous nucleotides derived from any of the sequences described herein, (ii) X equals Y, and (iii) X is greater than or equal to 6 nucleotides and up to 5000 nucleotides, preferably greater than or equal to 8 nucleotides and up to 5000 nucleotides, more preferably 10-12 nucleotides and up to 5000 nucleotides, and even more preferably 15-20 nucleotides, up to the number of nucleotides present in the full-length sequences described herein, including all integer values falling within the above-described ranges.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

The term "derived from" is used to identify the viral source of a molecule (e.g., polynucleotide, polypeptide). A first polynucleotide is "derived from" second polynucleotide if it has the same or substantially the same base pair sequence as a region of the second polynucleotide, its cDNA, complements thereof, or if it displays sequence identity as described above. Thus, a viral sequence or polynucleotide is "derived from" a particular virus (e.g., species) if it has (i) the same or substantially the same sequence as the virus sequence or (ii) displays sequence identity to polypeptides of that virus as described above.

A first polypeptide is "derived from" a second polypeptide if it is (i) encoded by a first polynucleotide derived from a second polynucleotide, or (ii) displays sequence identity to the second polypeptides as described above. Thus, a virus polypeptide (protein) is "derived from" a particular virus if it is (i) encoded by an open reading frame of a polynucleotide of that virus (viral polynucleotide), or (ii) displays sequence identity, as described above, to polypeptides of that virus.

Both polynucleotide and polypeptide molecules can be physically derived from the virus or produced recombinantly or synthetically, for example, based on known sequences.

The term "heterologous" is a relative term, which when used with reference to nucleic acids indicates that the nucleic acid comprises two or more subsequences that are not found in the same relationship to each other in nature. Thus, in the pending case, a nucleic acid encoding a respiratory viral protein is heterologous to the sequences of the alphavirus replicon vector, vector construct or replicon particle within which it is contained.

"Subgenomic RNA" refers to an RNA molecule of a length or size that is smaller than the genomic RNA from which it was derived. Subgenomic RNA is transcribed from an internal promoter whose sequences reside within the genomic RNA or its complement. In preferred embodiments, the subgenomic RNA is produced from an alphavirus vector construct, RNA vector replicon, or defective helper construct and encodes one or more alphavirus structural proteins or other heterologous sequences of interest. Generally, the subgenomic RNA resembles a typical mRNA with 5' and 3' end non-translated regions and a protein encoding open reading frame.

As used herein, the phrase "vector construct" generally refers to any assembly that is capable of directing the expression of a nucleic acid sequence(s) or gene(s) of interest. The vector construct typically includes a transcriptional promoter/enhancer or locus defining element(s), or other elements which control gene expression by other means such as alternate splicing, nuclear RNA export, post-translational modification of messenger, or post-transcriptional modification of protein. In addition, the vector construct typically includes a sequence which, when transcribed, is operably linked to the sequence(s) or gene(s) of interest and acts as a translation initiation sequence. The vector construct may also optionally include a signal that directs polyadenylation, a selectable marker, as well as one or more restriction sites and a translation termination sequence. Examples of vector constructs include ELVIS vectors, which comprise the cDNA complement of RNA vector constructs, RNA vector constructs themselves, alphavirus vector constructs, CMV vector constructs and the like.

"Alphavirus vector construct" refers to an assembly that is capable of directing the expression of a sequence or gene of interest. Such vector constructs are comprised of a 5' sequence that is capable of initiating transcription of an alphavirus RNA (also referred to as 5' conserved nucleotide sequence elements (CSE), or, 5' cis replication sequence), as well as sequences which, when expressed, code for biologically active alphavirus nonstructural proteins (e.g., nsP1, nsP2, nsP3, nsP4), an alphavirus RNA polymerase recognition sequence (also referred to as 3' CSE, or, 3' cis replication sequence), and, optionally a polyadenylate tract. In addition, the vector construct may include a viral subgenomic "junction region" promoter, sequences from one or more structural protein genes or portions thereof, extraneous nucleic acid molecule(s) which are of a size sufficient to allow production of virus-like particles (e.g., replicon particles), a 5' promoter which is capable of initiating the synthesis of viral RNA from cDNA in vitro or in vivo (e.g., within a eukaryotic cell), a heterologous sequence to be expressed, and one or more restriction sites for insertion of heterologous sequences.

"Alphavirus RNA replicon vector," "RNA replicon vector," "replicon vector" or "replicon" refers to an RNA molecule that is capable of directing its own amplification or self-replication in vivo, within a target cell. To direct its own amplification, the RNA molecule should encode the enzyme(s) necessary to catalyze RNA amplification (e.g., alphavirus nonstructural proteins nsP1, nsP2, nsP3, nsP4) and also contain cis RNA sequences required for replication which are recognized and utilized by the encoded enzymes(s). An alphavirus RNA vector replicon should contain the following ordered elements: 5' viral or cellular sequences required for nonstructural protein-mediated amplification (may also be referred to as 5' CSE, or 5' cis replication sequence, or 5' viral sequences required in cis for replication, or 5' sequence which is capable of initiating transcription of an alphavirus), sequences which, when expressed, code for biologically active alphavirus nonstructural proteins (e.g., nsP1, nsP2, nsP3, nsP4), and 3' viral or cellular sequences required for nonstructural protein-mediated amplification (may also be referred as 3' CSE, or 3' viral sequences required in cis for replication, or an alphavirus RNA polymerase recognition sequence). The alphavirus RNA vector replicon may contain a means to express one or more heterologous sequence(s), such as for example, an IRES or a viral (e.g., alphaviral) subgenomic promoter (e.g., junction region promoter) which may, in certain embodiments, be modified in order to increase or reduce viral transcription of the subgenomic fragment, or to decrease homology with defective helper or structural protein expression cassettes, and one or more heterologous sequence(s) to be expressed. A replicon can also contain additional sequences, for example, one or more heterologous sequence(s) encoding one or more polypeptides (e.g., a protein-encoding gene or a 3' proximal gene) and/or a polyadenylate tract. The replicon should not contain sequences encoding for all of the alphavirus structural proteins (capsid, E2, E1). Non-limiting examples of heterologous sequences that can be expressed by replicon vectors are described, for example in U.S. Pat. No. 6,015,686, incorporated by reference in its entirety herein, and include for example antigens, lymphokines, cytokines, etc.

A "packaging signal" or "packaging sequence" refers to a cis-acting sequence that is involved in incorporating nucleotides (e.g., genomic DNA or RNA) into viral particles (virions). Packaging signals from many viruses have been described. See, e.g., Youil R. et al. (2003) Human gene therapy 14(10):1017-1034; Beasley B E et al (2002) J. of Virology 76(10):4950-4960; Watanabe T et al. (2003) J. of Virology 77(19):10575-10583.

"Recombinant Alphavirus Particle" or "replicon particle" refers to a virion-like structural unit containing an alphavirus RNA vector replicon. Generally, a recombinant alphavirus particle or replicon particle comprises one or more alphavirus structural proteins, a lipid envelope and an RNA vector replicon. Preferably, the recombinant alphavirus particle contains a nucleocapsid structure that is contained within a host cell-derived lipid bilayer, such as a plasma membrane, in which alphaviral-encoded envelope glycoproteins are embedded. The particle may also contain other components (e.g., targeting elements, other viral structural proteins, or other receptor binding ligands) that direct the tropism of the particle from which the alphavirus was derived.

"Alphavirus structural protein expression cassette" refers to a vector construct that is capable of expression of one or more alphavirus structural proteins. The alphavirus structural protein expression cassette may be a "Defective helper construct" that is capable of RNA amplification or replication, and expression of one or more alphavirus structural proteins in response to biologically active alphavirus nonstructural proteins supplied in trans. The defective helper construct typically contains the following ordered elements: a 5' amplification or cis replication sequence, a viral subgenomic junction region promoter, sequences which, when expressed, code for one or more biologically active alphavirus structural proteins (e.g., C, E3, E2, 6K, E1), 3' amplification or cis replication sequences, and a polyadenylate tract. The defective helper construct may also contain a 5' promoter which is capable of initiating the synthesis of viral RNA from cDNA in vitro or in vivo (e.g., in a eukaryotic cell), a 3' sequence which controls transcription termination, splice recognition sequences, a catalytic ribozyme processing sequence, a sequence encoding a selectable marker, and/or a nuclear export signal. A defective helper construct should not encode all four functional alphavirus nonstructural proteins.

The terms "5' viral or cellular sequences required for nonstructural protein-mediated amplification" and "5' sequences required for nonstructural protein-mediated amplification" and "amplification sequences" and "5' amplification sequences" and "5' CSE" and "5' viral sequences required in cis for replication" and "5' sequence that is capable of initiating transcription of an alphavirus" are used interchangeably to refer to a functional element that provides a recognition site at which the virus or virus-derived vector synthesizes positive strand RNA. Thus, it may be a complement of the actual sequence contained within the virus or vector, which corresponds to the 3' end of the minus-strand RNA copy, which is bound by the nonstructural protein replicase complex, and possibly additional host cell factors, from which transcription of the positive-strand RNA is initiated. A wide variety of sequences have been utilized as amplification sequences including, for example, alphavirus 5'-end nontranslated regions (NTR) and other adjacent sequences, such as for example sequences through nucleotides 210, 250, 300, 350, 400, or 450. Alternatively, for example in the case of Sindbis (SIN) vectors, non-alphavirus nucleotides 10-75 for tRNA Asparagine (tRNAasp) (Schlesinger et al., U.S. Pat. No. 5,091,309) have been used.

As used herein, the term "5' modified amplification sequence" refers to a nucleotide (RNA or DNA) molecule comprising an amplification sequence as defined above, whose primary structure (sequence) has been modified (e.g., substitutions, additions, deletions) as compared to known amplification signals, such that the modified sequences are defective as a packaging signal but retain their amplification (replication) functionality. For example, modified amplification sequences may include reduced homology to packaging signals at the primary sequence level, while the secondary structure remains that of the original amplification sequence. Modified amplification sequences can further include additional sequences, so long as secondary structure and/or cis-acting amplification capability is maintained.

The term "3' Proximal Gene" refers to a nucleotide sequence encoding a protein, which is contained within a replicon vector, Eukaryotic Layered Vector Initiation System, defective helper RNA or structural protein expression cassette, and located within a specific position relative to another element. The position of this 3' proximal gene should be determined with respect to the 3' sequence required for nonstructural protein-mediated amplification (defined above), wherein the 3' proximal gene is the protein-encoding sequence 5' (upstream) of, and immediately preceding this element.

The term "viral subgenomic promoter" refers to a sequence of virus origin that, together with required viral and cellular polymerase(s) and other factors, permits transcription of an RNA molecule of less than genome length. For an alphavirus (alphaviral) subgenomic promoter or alphavirus (alphaviral) subgenomic junction region promoter, this sequence is derived generally from the region between the nonstructural and structural protein open reading frames (ORFs) and normally controls transcription of the subgenomic mRNA. Typically, the alphavirus subgenomic promoter consists of a core sequence that provides most promoter-associated activity, as well as flanking regions (e.g., extended or native promoter) that further enhance the promoter-associated activity. The subgenomic promoter may be a complement of the actual sequence contained within the virus or vector, which corresponds to the region in a minus-strand RNA copy, which promotes transcription initiation of the positive-strand subgenomic mRNA. For example, in the case of the alphavirus prototype, Sindbis virus, the normal subgenomic junction region promoter typically begins at approximately nucleotide number 7579 and continues through at least nucleotide number 7612 (and possibly beyond). At a minimum, nucleotides 7579 to 7602 are believed to serve as the core sequence necessary for transcription of the subgenomic fragment.

The terms "3' viral or cellular sequences required for nonstructural protein-mediated amplification" or "3' sequences required for nonstructural protein-mediated amplification" are used interchangeably with the terms 3' CSE, or 3' cis replication sequences, or 3' viral sequences required in cis for replication, or an alphavirus RNA polymerase recognition sequence. This sequence is a functional element that provides a recognition site at which the virus or virus-derived vector begins replication (amplification) by synthesis of the negative RNA strand. A wide variety of sequences may be utilized for this function. For example, the sequence may include a complete alphavirus 3'-end nontranslated region (NTR), such as for example, with SIN, which would include nucleotides 11,647 to 11,703, or a truncated region of the 3' NTR, which still maintains function as a recognition sequence (e.g., nucleotides 11,684 to 11,703). Other examples of sequences that may be utilized in this context include, but are not limited to, non-alphavirus or other sequences that maintain a similar functional capacity to permit initiation of negative strand RNA synthesis (e.g., sequences described in George et al., (2000) J. Virol. 74:9776-9785).

"Stable transformation" refers to the introduction of a nucleic acid molecule into a living cell, and long-term or permanent maintenance of that nucleic acid molecule in progeny cells through successive cycles of cell division. The nucleic acid molecule may be maintained in any cellular compartment, including, but not limited to, the nucleus, mitochondria, or cytoplasm. In preferred embodiments, the nucleic acid molecule is maintained in the nucleus. Maintenance may be intrachromosomal (integrated) or extrachromosomal, as an episomal event. "Alphavirus packaging cell line" refers to a cell which contains an alphavirus structural protein expression cassette and which produces recombinant alphavirus particles after introduction of an alphavirus vector construct, RNA vector replicon, eukaryotic layered vector initiation system (e.g., U.S. Pat. No. 5,814,482), or recombinant alphavirus particle. The parental cell may be of mammalian or non-mammalian origin. Within preferred embodiments, the packaging cell line is stably transformed with the structural protein expression cassette.

"Eukaryotic Layered Vector Initiation System" refers to an assembly that is capable of directing the expression of a sequence or gene of interest. The Eukaryotic Layered Vector Initiation System should contain a 5' promoter that is capable of initiating in vivo (i.e. within a eukaryotic cell) the synthesis of RNA from cDNA, and a nucleic acid vector sequence (e.g., viral vector) that is capable of directing its own replication in a eukaryotic cell and also expressing a heterologous sequence. Preferably, the nucleic acid vector sequence is an alphavirus-derived sequence and is comprised of 5' viral or cellular sequences required for nonstructural protein-mediated amplification (also referred to as 5' CSE, or 5' cis replication sequence, or 5' viral sequences required in cis for replication, or 5' sequence which is capable of initiating transcription of an alphavirus), as well as sequences which, when expressed, code for biologically active alphavirus nonstructural proteins (e.g., nsP1, nsP2, nsP3, nsP4), and 3' viral or cellular sequences required for nonstructural protein-mediated amplification (also referred to as 3' CSE, or 3' viral sequences required in cis for replication, or an alphavirus RNA polymerase recognition sequence). In addition, the vector sequence may include a means to express heterologous sequence(s), such as for example, a viral (e.g., alphaviral) subgenomic promoter (e.g., junction region promoter) which may, in certain embodiments, be modified in order to prevent, increase, or reduce viral transcription of the subgenomic fragment, or to decrease homology with defective helper or structural protein expression cassettes, and one or more heterologous sequence(s) to be expressed. Preferably the heterologous sequence(s) comprises a protein-encoding gene and said gene is the 3' proximal gene within the vector sequence. The Eukaryotic Layered Vector Initiation System may also contain a polyadenylation sequence, splice recognition sequences, a catalytic ribozyme processing sequence, a nuclear export signal, and a transcription termination sequence. In certain embodiments, in vivo synthesis of the vector nucleic acid sequence from cDNA may be regulated by the use of an inducible promoter or subgenomic expression may be inducible through the use of translational regulators or modified nonstructural proteins.

A "pathogen" refers to any organism that is associated with or causes disease. Thus, the term "respiratory pathogen" refers any pathogenic organism that is transmitted by respiration or is associated with or causes disease in the respiratory tract. Respiratory pathogens are known in the art and include, but are not limited to, the viruses, bacteria, parasites and fungi described herein.

An "antigen" refers to a molecule containing one or more epitopes (either linear, conformational or both) that will stimulate a host's immune system to make a humoral and/or cellular antigen-specific response. The term is used interchangeably with the term "immunogen." Normally, an epitope will include between about 3-15, generally about 5-15 amino acids. A B-cell epitope is normally about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term "antigen" denotes both subunit antigens, (i.e., antigens which are separate and discrete from a whole organism with which the antigen is associated in nature), as well as, killed, attenuated or inactivated bacteria, viruses, fungi, parasites or other microbes as well as tumor antigens, including extracellular domains of cell surface receptors and intracellular portions that may contain T-cell epitopes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide that expresses an antigen or antigenic determinant in vivo, such as in gene therapy and DNA immunization applications, is also included in the definition of antigen herein.

Epitopes of a given protein can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Nat'l Acad Sci. USA* 81:3998-4002; Geysen et al. (1986) *Molec. Immunol* 23:709-715, all incorporated herein by reference in their entireties.

Similarly, conformational epitopes are readily identified by determining spatial conformation of amino acids such as by, e.g., x-ray crystallography and nuclear magnetic resonance. See, e.g., *Epitope Mapping Protocols*, supra.

For purposes of the present invention, antigens can be derived from any of several known viruses, bacteria, parasites and fungi, as described more fully below. The term also intends any other antigen to which an immune response is desired. Furthermore, for purposes of the present invention, an "antigen" refers to a protein that includes modifications, such as deletions, additions and substitutions (generally conservative in nature), to the native sequence, so long as the protein maintains the ability to elicit an immunological response, as defined herein. These modifications may be deliberate, as through site-directed mutagenesis, or may be accidental, such as through mutations of hosts that produce the antigens.

An "immunological response" to an antigen or composition is the development in a subject of a humoral and/or a cellular immune response to an antigen present in the composition of interest. For purposes of the present invention, a "humoral immune response" refers to an immune response mediated by antibody molecules, including secretory (IgA) or IgG molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. In addition, a chemokine response may be induced by various white blood or endothelial cells in response to an administered antigen.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189-4199; Doe et al., *Eur. J. Immunol.* (1994) 24:2369-2376. Recent methods of measuring cell-mediated immune response include measurement of intracellular cytokines or cytokine secretion by T-cell populations (e.g., by ELISPOT technique), or by measurement of epitope specific T-cells (e.g., by the tetramer technique)(reviewed by McMichael, A. J., and O'Callaghan, C. A., *J. Exp. Med.* 187(9):1367-1371, 1998; Mcheyzer-Williams, M. G., et al, *Immunol. Rev.* 150:5-21, 1996; Lalvani, A., et al, *J. Exp. Med.* 186; 859-865, 1997).

Thus, an immunological response as used herein may be one that stimulates CTLs, and/or the production or activation of helper T-cells. The production of chemokines and/or cytokines may also be stimulated. The antigen of interest may also elicit an antibody-mediated immune response. Hence, an immunological response may include one or more of the following effects: the production of antibodies (e.g., IgA or IgG) by B-cells; and/or the activation of suppressor, cytotoxic, or helper T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

An "immunogenic composition" is a composition that comprises an antigenic molecule (or nucleotide sequence encoding an antigenic molecule) where administration of the composition to a subject results in the development in the subject of a humoral and/or a cellular and/or mucosal immune response to the antigenic molecule of interest. The immunogenic composition can be introduced directly into a recipient subject, such as by injection, inhalation, oral, intranasal or any other parenteral or mucosal (e.g., intra-rectally or intra-vaginally) route of administration.

By "subunit vaccine" is meant a vaccine composition that includes one or more selected antigens but not all antigens, derived from or homologous to, an antigen from a pathogen of interest such as from a virus, bacterium, parasite or fungus. Such a composition is substantially free of intact pathogen cells or pathogenic particles, or the lysate of such cells or particles. Thus, a "subunit vaccine" can be prepared from at least partially purified (preferably substantially purified) immunogenic polypeptides from the pathogen, or analogs thereof. The method of obtaining an antigen included in the subunit vaccine can thus include standard purification techniques, recombinant production, or synthetic production.

Alphavirus Constructs and Particles

The immunogenic compositions described herein include one or more alphavirus constructs, replicon vectors or replicon particles, each construct or particle comprising one or more sequences encoding proteins derived from respiratory pathogens.

Several members of the alphavirus genus are being developed as "replicon" expression vectors for use vaccine and therapeutic applications. Replicon vectors may be utilized in any of several formats, including DNA vector constructs, RNA replicon vectors, and recombinant replicon particles. Such replicon vectors have been derived from alphaviruses that include, for example, SIN (Xiong et al. (1989) *Science* 243:1188-1191; Dubensky et al., (1996) *J. Virol.* 70:508-519; Hariharan et al. (1998) *J. Virol.* 72:950-958; Polo et al. (1999) *PNAS* 96:4598-4603), Semliki Forest virus (Liljestrom (1991) *Bio/Technology* 9:1356-1361; Berglund et al. (1998) *Nat. Biotech.* 16:562-565), VEE (Pushko et al. (1997) *Virology* 239:389-401), and chimeras derived from multiple alphaviruses (U.S. Pat. No. 6,376,236B1; WO2002099035; Perri et al. (2003) *J. Virol.* 77:10394-10403).

Generally speaking, an alphavirus replicon particle refers to a virus-like particle containing a self-replicating alphavirus vector or "replicon" nucleic acid. The replicon particle itself is generally considered to be replication incompetent or "defective," that is no progeny replicon particles will result when a host cell is infected with a replicon particle, because genes encoding one or more structural proteins necessary for packaging are deleted. Through the years, several synonymous terms including recombinant viral particle, recombinant alphavirus particle, alphavirus replicon particle and replicon particle have emerged that are used to describe replicon particles. However, as used herein, these terms all refer to virion-like units containing an alphavirus-derived RNA vector replicon. Moreover, these terms may be referred to collectively as vectors, vector constructs or gene delivery vectors.

A wide body of literature has now demonstrated the usefulness of alphavirus-derived replicon vectors (e.g., DNA, RNA, particles) for stimulating immune responses, such as in prophylactic and therapeutic applications (see for example, Dubensky et al., ibid; Berglund et al., ibid; Hariharan et al., ibid, Pushko et al., ibid; Polo et al., ibid; Davis et al. (2000) *J Virol.* 74:371-378; Schlesinger & Dubensky (1999) *Curr Opin. Biotechnol.* 10:434-439; Berglund et al. (1999) *Vaccine* 17:497-507; Kirman et al. (2003) *Infect. Immun.* 71:575-579; Pasetti et al. (2003) *J. Virol.* 77:5209-5217; Vajdy et al. (2001) *J. Inf. Dis.* 184:1613-1616; Perri et al. (2003) *J. Virol.* 77:10394-10403)). The present invention contemplates the derivation and use of alphavirus replicon vectors expressing one or more antigens from human or veterinary respiratory pathogens (e.g., viruses, bacteria, fungi) as a means to stimulate the antigen-specific immune response(s) and provide a protective vaccine modality.

The typical "replicon" configuration (FIG. 1) of alphavirus vector constructs, as described in more detail above and in U.S. Pat. Nos. 5,789,245, 5,843,723, 5,814,482, and 6,015,694, WO 00/61772, WO 02/99035), comprises a 5' sequence which initiates transcription of alphavirus RNA, a nucleotide sequence encoding alphavirus nonstructural proteins, a viral subgenomic junction region promoter which directs the expression of an adjacent heterologous nucleic acid sequence, an RNA polymerase recognition sequence and preferably a polyadenylate tract. Other terminology to define the same elements is also known in the art.

Although alphavirus vectors, such as those of the present invention, may be used directly for administration in vivo as RNA, or delivered as a plasmid-based cDNA (e.g., Eukaryotic Layered Vector Initiation System), often, for in vivo vaccine and therapeutic applications, the alphavirus RNA replicon vector or replicon RNA is first packaged into a virus-like particle, comprising alphavirus structural proteins (e.g., capsid protein and envelope glycoproteins). Because of their configuration, vector replicons do not express these alphavirus structural proteins necessary for packaging into recombinant alphavirus replicon particles. Thus, to generate replicon particles, the structural proteins must be provided in trans (FIG. 1).

Packaging may be accomplished by a variety of methods, including transient approaches such as co-transfection of in vitro transcribed replicon and defective helper RNA(s) (Liljestrom, *Bio/Technology* 9:1356-1361, 1991; Bredenbeek et al., *J. Virol.* 67:6439-6446, 1993; Frolov et al., *J. Virol.* 71:2819-2829, 1997; Pushko et al., *Virology* 239:389-401, 1997; U.S. Pat. Nos. 5,789,245 and 5,842,723) or plasmid DNA-based replicon and defective helper constructs (Dubensky et al., *J. Virol.* 70:508-519, 1996), as well as introduction of alphavirus replicons into stable packaging cell lines (PCL) (Polo et al., *PNAS* 96:4598-4603, 1999; U.S. Pat. Nos. 5,789,245, 5,842,723, 6,015,694; WO 9738087 and WO 9918226).

The trans packaging methodologies permit the modification of one or more structural protein genes (for example, to incorporate sequences of alphavirus variants such as attenuated mutants U.S. Pat. Nos. 5,789,245, 5,842,723, 6,015, 694), followed by the subsequent incorporation of the modified structural protein into the final replicon particles. In addition, such packaging permits the overall modification of alphavirus replicon particles by packaging of a vector construct or RNA replicon derived from a first alphavirus using structural proteins derived from a second alphavirus different from that of the vector construct (WO 95/07994; Polo et al., 1999, ibid; Gardner et al., Virol., 74:11849-11857, 2000; Perri et al. (2003) *J. Virol.* 77:10394-10403)).

A. Alphavirus Replicons and Particles

As noted above, replicon particles as described herein typically include one or more polynucleotide sequences (e.g., RNA replicon). When found in replicon particles, these polynucleotides are surrounded by (and interact with) one or more alphavirus structural proteins. Non-limiting examples of polynucleotide sequences and structural proteins that can be used in the practice of the invention are described herein.

A.1. Nucleotide Components

The particles, vectors and replicons described herein typically include a variety of nucleic acid sequences, both coding and non-coding sequences. It will be apparent that the compositions described herein generally comprise less than a complete alphavirus genome (e.g., contain less than all of the coding and/or non-coding sequences contained in a genome of an alphavirus).

A.2. Non-Coding Polynucleotide Components

The particles and replicons described herein typically contain sequences that code for polypeptides (e.g., structural or nonstructural) as well as non-coding sequences, such as control elements. Non-limiting examples of non-coding sequences include 5' sequences required for nonstructural protein-mediated amplification, a means for expressing a heterologous nucleotide sequence, and 3' sequences required for nonstructural protein-mediated amplification (U.S. Pat. Nos. 5,843,723; 6,015,694; 5,814,482; PCT publications WO 97/38087; WO 00/61772). It will be apparent from the teachings herein that one, more than one or all of the sequences described herein can be included in the particles, vectors and/or replicons described herein and, in addition, that one or more of these sequences can be modified or otherwise manipulated for use according to the teachings herein.

Thus, the polynucleotides described herein typically include a 5' sequence required for nonstructural protein-mediated amplification. Non-limiting examples of suitable 5' sequences include control elements such as native alphavirus 5'-end, a non-native DI alphavirus 5'-end, and a cellular RNA derived sequence (e.g., tRNA element) (e.g., Monroe et al., PNAS 80:3279-3283, 1983).

The polynucleotide sequences also generally include a means for expressing a heterologous nucleotide sequence (e.g., polypeptide encoding sequence). Non-limiting examples of such means include control elements such as promoters and the like, for example, a native alphavirus subgenomic promoter from homologous virus, a native alphavirus subgenomic promoter from heterologous virus, a core alphavirus subgenomic promoter (homologous or heterologous), minimal sequences upstream or downstream from core subgenomic promoter, mutations/deletions/additions of core or native subgenomic promoter, a non-alphavirus derived compatible subgenomic promoter (e.g. plant virus), an internal ribosome entry site (IRES), and/or a ribosomal readthrough element (e.g., BiP).

Non-limiting examples of suitable 3' sequences required for nonstructural protein-mediated amplification include control elements such as a native alphavirus 3'-end, a non-native DI alphavirus 3'-end and sequences containing mutations, deletions, or additions of above sequences.

A.3. Coding Sequences

The compositions described herein may also include one or more sequences coding for various alphavirus polypeptides, for example one or more of the nonstructural (nsP1, nsP2, nsP3, nsP4) or structural (e.g., capsid, envelope glycoprotein) alphavirus polypeptides.

As described in Strauss et al. (1984), supra, a wild-type SIN genome is 11,703 nucleotides in length, exclusive of the 5' cap and the 3'-terminal poly(A) tract. After the 5'-terminal cap there are 59 nucleotides of 5' nontranslated nucleic acid followed by a reading frame of 7539 nucleotides that encodes the nonstructural polypeptides and which is open except for a single opal termination codon. Following 48 untranslated bases located in the junction region that separates the nonstructural and structural protein coding sequences, there is an open reading frame 3735 nucleotides long that encodes the structural proteins. Finally, the 3' untranslated region is 322 nucleotides long. The nonstructural proteins are translated from the genomic RNA as two polyprotein precursors. The first includes nsP1, nsP2 and nsP3 is 1896 amino acids in length and terminates at an opal codon at position 1897. The fourth nonstructural protein, nsP4, is produced when readthrough of the opal codon produces a second polyprotein precursor of length 2513 amino acids, which is then cleaved post-translationally.

A wild-type alphavirus genome also includes sequences encoding structural proteins. In SIN, the structural proteins are translated from a subgenomic message which begins at nucleotide 7598, is 4106 nucleotides in length (exclusive of the poly(A) tract), and is co-terminal with the 3' end of the genomic RNA. Like the nonstructural proteins, the structural proteins are also translated as a polyprotein precursor that is cleaved to produce a nucleocapsid protein and two integral membrane glycoproteins as well as two small peptides not present in the mature virion. Thus, the replicons, particles and vectors of the present invention can include one or more coding sequences derived from one or more alphaviruses.

B. Alphavirus Structural Proteins

The structural proteins surrounding (and in some cases, interacting with) the alphavirus replicon or vector polynucleotide component(s) can include both capsid and envelope proteins. In most instances, the polynucleotide component(s) are surrounded by multiple copies of the capsid protein(s), which form the nucleocapsids. In turn, the nucleocapsid preferably is surrounded by a lipid envelope containing the envelope glycoprotein(s). Alphavirus capsid proteins and envelope glycoproteins are described generally in Strauss et al. (1994) Microbiol. Rev., 58:491-562. The capsid protein is the N-terminal protein of the alphavirus structural polyprotein, and following processing from the polyprotein, interacts with alphavirus RNA and other capsid protein monomers to form nucleocapsid structures. Alphavirus envelope glycoproteins (e.g., E2, E1) protrude from the enveloped particle as surface "spikes", which are functionally involved in receptor binding and entry into the target cell.

C. Methods of Producing Alphavirus Replicon Particles

The alphavirus replicon particles according to the present invention may be produced using a variety of published methods. Such methods include, for example, transient packaging approaches, such as the co-transfection of in vitro transcribed replicon and one or more defective helper RNA(s) (Liljestrom, Bio/Technology 9:1356-1361, 1991; Bredenbeek et al., J. Virol. 67:6439-6446, 1993; Frolov et al., J. Virol. 71:2819-2829, 1997; Pushko et al., Virology 239:389-401, 1997; U.S. Pat. Nos. 5,789,245 and 5,842,723) or plasmid DNA-based replicon and defective helper constructs (Dubensky et al., J. Virol. 70:508-519, 1996), as well as introduction of alphavirus replicons into stable packaging cell lines (PCL) (Polo et al., PNAS 96:4598-4603, 1999; U.S. Pat. Nos. 5,789,245, 5,842,723, 6,015,694; WO 97/38087, WO 99/18226, WO 00/61772, WO 00/39318, and WO 01/92552). Other production methods include the use of non-defective helper based RNA or DNA structural protein expression cassettes, which operably encode one or more alphavirus structural proteins (U.S. Pat. Nos. 5,789,245, 5,842,723, 6,015,694; WO 97/38087, WO 99/18226, WO 00/61772, WO 00/39318, WO 01/92552, WO2004085660A2, WO2003023026A1).

In preferred embodiments, stable alphavirus packaging cell lines are utilized for replicon particle production. The PCL may be transfected with in vitro transcribed replicon RNA, transfected with plasmid DNA-based replicon (e.g., ELVIS vector), or infected with a seed stock of replicon particles, and then incubated under conditions and for a time sufficient to produce high titer packaged replicon particles in the culture supernatant. In particularly preferred embodiments, PCL are utilized in a two-step process, wherein as a first step, a seed stock of replicon particles is produced by transfecting the PCL with a plasmid DNA-based replicon. A much larger stock of replicon particles is then produced in the second step, by infecting a fresh culture of the PCL with the seed stock. This infection may be performed using various multiplicities of infection (MOI), including a MOI=0.01, 0.05, 0.1, 0.5, 1.0, 3, 5, or 10. Preferably infection is performed at a low MOI (e.g., less than 1). Replicon particles at titers even >$10^8$ infectious units (IU)/ml can be harvested over time from PCL infected with the seed stock. In addition, the replicon particles can subsequently be passaged in yet larger cultures of naïve PCL by repeated low multiplicity infection, resulting in commercial scale preparations with the same high titer. Importantly, by using PCL of the "split" structural gene configuration, these replicon particle stocks may be produced free from detectable contaminating RCV.

Large-scale production of alphavirus replicon particles may be performed using a bioreactor. Preferably, the bioreactor is an external component bioreactor, which is an integrated modular bioreactor system for the mass culture, growth, and process control of substrate attached cells. The attachment and propagation of cells (e.g., alphavirus packaging cells) occurs in a vessel or chamber with tissue culture treated surfaces, and the cells are with fresh media for increased cell productivity. Monitoring and adjustments are performed for such parameters as gases, temperature, pH, glucose, etc., and crude vector is harvested using a perfusion pump. Typically, the individual components of an External Bioreactor separate external modules that are connected (i.e., via tubing). The external components can be pumps, reservoirs, oxygenators, culture modules, and other non-standard parts. A representative example of an External Component Bioreactor is the CellCube™ system (Corning, Inc).

In addition to using the external component bioreactor described herein, a more traditional Stir Tank Bioreactor may also be used, in certain instances, for alphavirus replicon particle production. In a Stir Tank Bioreactor, the alphavirus packaging cells may be unattached to any matrix (i.e., floating in suspension) or attached to a matrix (e.g., poly disks, micro- or macro carriers, beads). Alternatively, a Hollow Fiber Culture System may be used. Suspension adapted cell also may be utilized.

Following harvest, crude culture supernatants containing the chimeric alphavirus replicon particles may be clarified by passing the harvest through a filter (e.g., 0.2 uM, 0.45 uM, 0.65 uM, 0.8 uM pore size). Optionally, the crude supernatants may be subjected to low speed centrifugation prior to filtration to remove large cell debris. Within one embodiment, an endonuclease (e.g., Benzonase, Sigma #E8263) is added to the preparation of alphavirus replicon particles before or after a chromatographic purification step to digest exogenous nucleic acid. Further, the preparation may be concentrated prior to purification using one of any widely known methods (e.g., tangential flow filtration).

Crude or clarified alphavirus replicon particles may be concentrated and purified by chromatographic techniques (e.g., ion exchange chromatography, size exclusion chromatography, hydrophobic interaction chromatography, affinity chromatography). Two or more such purification methods may be performed sequentially. In preferred embodiments, at least one step of ion exchange chromatography is performed and utilizes an ion exchange resin, such as a tentacle ion exchange resin, and at least one step of size exclusion chromatography is performed. Briefly, clarified alphavirus replicon particle filtrates may be loaded onto a column containing a charged ion exchange matrix or resin (e.g., cation or anion exchange). The matrix or resin may consist of a variety of substances, including but not limited to cross-linked agarose, cross-linked polystyrene, cross-linked styrene, hydrophilic polyether resin, acrylic resin, and methacrylate based resin. The ion exchanger component may comprise, but is not limited to, a cationic exchanger selected from the list consisting of sulphopropyl cation exchanger, a carboxymethyl cation exchanger, a sulfonic acid exchanger, a methyl sulfonate cation exchanger, and an SO3-exchanger. In other embodiments, the ion exchanger component may comprise, but is not limited to, an anionic exchanger selected from the list consisting of DEAE, TMAE, and DMAE. Most preferably, ion exchange chromatography is performed using a tentacle cationic exchanger, wherein the ion exchange resin is a methacrylate-based resin with an SO3-cation exchanger (e.g., Fractogel® EDM SO3-).

The replicon particles may be bound to the ion exchange resin followed by one or more washes with buffer containing a salt (e.g., 250 mM or less NaCl). Replicon particles then may be eluted from the column in purified form using a buffer with increased salt concentration. In preferred embodiments, the salt concentration is a least 300 mM, 350 mM, 400 mM, 450 mM or 500 mM. Elution may be monitored preferably by a spectrophotometer at 280 nm, but also by replicon titer assay, transfer of expression (TOE) assay, or protein gel analysis with subsequent Coomassie staining or Western blotting.

The higher salt elution buffer subsequently may be exchanged for a more desirable buffer, for example, by dilution in the appropriate aqueous solution or by passing the particle-containing eluate over a molecular exclusion column. Additionally, the use of a molecular size exclusion column may also provide, in certain instances, further purification. For example, in one embodiment Sephacryl S-500 or S-400 (Pharmacia) chromatography may be used as both a buffer exchange as well as to further purify the fractions containing the replicon particles eluted from an ion exchange column. Using this particular resin, the replicon particles generally are eluted in the late void volume and show improvement in the level of purity as some of the contaminants are smaller in molecular weight and are retained on the column longer. However, alternative resins of different compositions as well as size exclusion could also be used that might yield similar or improved results. In these strategies, larger-sized resins such as Sephacryl S-1000 could be incorporated that would allow the replicon particles to enter into the matrix and thus be retained longer, allowing fractionation.

One of skill in the art will readily understand that introduction of replicon RNA into permissive cells may be performed by a variety of means, such as for example, transfection or electroporation of RNA (e.g., in vitro transcribed RNA), transcription of RNA within the cell from DNA (e.g., eukaryotic layered vector initiation system), or delivery by viral or virus-like particles (e.g., replicon particles) and introduction of defective helper RNA or mRNA encoding one or more alphavirus structural proteins into permissive cells may also be performed by a variety of means, such as for example, transfection or electroporation of RNA (e.g., in vitro transcribed RNA) or transcription of RNA within the cell from DNA (e.g., structural protein expression cassette).

D. Inactivated Viruses

The invention includes compositions comprising inactivated (or killed) virus (e.g., PIV) and methods for the production thereof. Inactivated viral compositions can be used as a prophylactic vaccine. Preferably the inactivated virus vaccine composition comprises an amount of inactivated virus which is equivalent to a virus titer of from about 4 to 8 logs plaque forming units (PFU) or 4 to 8 logs tissue culture infectious dose 50 (TCID50) per milliliter. Still more preferably the inactivated virus vaccine composition comprises an amount of inactivated virus which is equivalent to a virus titer of from about 5 to 9 logs plaque forming units (PFU) or 5 to 9 logs tissue culture infectious dose 50 (TCID50) per milliliter. The vaccine composition comprises a sufficient amount of the virus antigen to produce an immunological response in a primate.

Methods of inactivating or killing viruses are known in the art to destroy the ability of the viruses to infect mammalian cells. Such methods include chemical or physical means. Chemical means for inactivating a virus (e.g., PIV) include treatment of the virus with an effective amount of one or more of the following agents: detergents, formaldehyde, formalin, β-propiolactone, or UV light. Additional chemical means for inactivation include treatment with methylene blue, psoralen, carboxyfullerene (C60) or a combination of any thereof. Other methods of viral inactivation are known in the art, such as for example binary ethylamine, acetyl ethyleneimine, or gamma irradiation.

For example, β-propiolactone may be used at concentrations such as 0.01 to 0.5%, preferably at 0.5% to 0.2%, and still more preferably at 0.025 to 0.1%. The inactivating agent is added to virus containing culture supernatants (virus material) prior to or after harvesting said culture supernatants from vessels used for virus propagation, either with or without a step of cell disruption for release of cell-associated virus prior to harvesting. Further, the inactivating agent may be added after said culture supernatants have been stored frozen and thawed, or after one or more steps of purification to remove cell contaminants. β-propiolactone is added to the virus material, with the adverse shift in pH to acidity being controlled with sodium hydroxide (e.g., 1 N NaOH) or sodium bicarbonate solution. The combined inactivating agent-virus materials are incubated at temperatures from 4° C. to 37° C., for incubation times of preferably 12 to 72 hours.

Another inactivant that may be used is binary ethyleneimine. Equal volumes of a 0.2 molar bromoethylamine hydrobromide solution and a 0.4 molar sodium hydroxide solution are mixed and incubated at about 37° C. for 60 minutes. The resulting cyclized inactivant is binary ethyleneimine, which is added to the virus materials at 0.5 to 4 percent, and preferably at 1 to 3 percent, volume to volume. The inactivating virus materials are held from about 4° C. to 37° C. for 24 to 72 hours with periodic agitation. At the end of this incubation 20 ml. of a sterile 1 molar sodium thiosulfate solution is added to insure neutralization of the BEI.

In one embodiment, the invention includes an inactivating method that is designed to maximize exposure of the virus to the inactivating agent and to minimize long-term exposure of temperature sensitive virus particles to elevated temperatures. The invention includes an inactivation method comprising exposing the virus to the inactivation agent (such as BPL) for 12 to 24 hours at refrigeration temperatures followed by hydrolysis of any residual inactivating agent by elevating the temperature for only 3 hours. Preferably, the refrigeration temperatures are between 0 and 8° C., more preferably around 4° C. Preferably, the elevated temperature is between 33 and 41° C., more preferably around 37° C.

Diluted and undiluted samples of the inactivated virus materials are added to susceptible cell (tissue) culture (e.g., LLC-MK2, VERO) to detect any non-inactivated virus. The cultured cells are passaged multiple times and examined for the presence of virus based on any of a variety of methods, such as, for example, cytopathic effect (CPE) and antigen detection (e.g., via fluorescent antibody conjugates specific for the virus). Such tests allow determination of complete virus inactivation.

The viruses for inactivation or the alphavirus vectors typically will be cultured or propagated in a mammalian cell culture. The cell culture may be adherently growing cells or cells growing in suspension. Preferably the cells are of mammalian origin, but may also be derived from avian (e.g., hens' cells such as hens' embryo cells (CEF cells), EB45 cells), amphibian, reptile, insect, or fish sources. Mammalian sources of cells include, but are not limited to, human or non-human primate (e.g., MRC-5 (ATCC CCL-171), WI-38 (ATCC CCL-75), human embryonic kidney cells (293 cells, typically transformed by sheared adenovirus type 5 DNA), PER.C6, LLC-MK2 cells, VERO cells from monkey kidneys), horse, cow (e.g., MDBK cells), sheep, dog (e.g., MDCK cells from dog kidneys, ATCC CCL34 MDCK (NBL2) or MDCK 33016, deposit number DSM ACC 2219 as described in WO 97/37001), cat, and rodent (e.g., hamster cells such as BHK21-F, HKCC cells, or Chinese hamster ovary cells (CHO cells)), and may be obtained from a wide variety of developmental stages, including for example, adult, neonatal, fetal, and embryo. Preferably, the viruses of the invention are grown on LLC-MK2, VERO cells or fetal rhesus kidney cells.

Culture conditions for the above cell types are well-described in a variety of publications, or alternatively culture medium, supplements, and conditions may be purchased commercially, such as for example, as described in the catalog and additional literature of Cambrex Bioproducts (East Rutherford, N.J.). In certain embodiments, the host cells used in the methods described herein are cultured in serum free and/or protein free media. A medium is referred to as a serum-free medium in the context of the present invention in which there are no additives from serum of human or animal origin. Protein-free is understood to mean cultures in which multiplication of the cells occurs with exclusion of proteins, growth factors, other protein additives and non-serum proteins. The cells growing in such cultures naturally contain proteins themselves. Known serum-free media include Iscove's medium, Ultra-CHO medium (BioWhittaker) or EX-CELL (JRH Bioscience). Ordinary serum-containing media include Eagle's Basal Medium (BME) or Minimum Essential Medium (MEM) (Eagle, Science, 130, 432 (1959)) or Dulbecco's Modified Eagle Medium (DMEM or EDM), which are ordinarily used with up to 10% fetal calf serum or similar additives. Optionally, Minimum Essential Medium (MEM) (Eagle, Science, 130, 432 (1959)) or Dulbecco's Modified Eagle Medium (DMEM or EDM) may be used without any serum containing supplement. Protein-free media like PF-CHO (JHR Bioscience), chemically-defined media like ProCHO 4CDM (BioWhittaker) or SMIF 7 (Gibco/BRL Life Technologies) and mitogenic peptides like Primactone, Pepticase or HyPep™ (all from Quest International) or lactalbumin hydrolyzate (Gibco and other manufacturers) are also adequately known in the prior art. The media additives based on plant hydrolyzates have the special advantage that contamination with viruses, mycoplasma or unknown infectious agents can be ruled out.

The cell culture conditions to be used for the desired application (temperature, cell density, pH value, etc.) are variable over a very wide range owing to the suitability of the cell line employed according to the invention and can be adapted to the requirements of the virus or vector propagation.

Methods of purification of inactivated virus are known in the art and may include one or more of for instance gradient centrifugation, ultracentrifugation, continuous-flow ultracentrifugation and chromatography, such as ion exchange chromatography, size exclusion chromatography, and liquid affinity chromatography. See J P Gregersen "Herstellung von Virussimpfstoffen aus Zellkulturen" Chapter 4.2 in Pharmazeutische Biotecnologie (eds. O. Kayser and R H Mueller) Wissenschaftliche Verlagsgesellschaft, Stuttgart, 2000. See also, O'Neil et al., "Virus Harvesting and Affinity Based Liquid Chromatography. A Method for Virus Concentration and Purification", Biotechnology (1993) 11:173-177; Prior et al., "Process Development for Manufacture of Inactivated HIV-1", Pharmaceutical Technology (1995) 30-52; and Majhdi et al., "Isolation and Characterization of a Coronavirus from Elk Calves with diarrhea" Journal of Clinical Microbiology (1995) 35(11): 2937-2942.

Other examples of purification methods suitable for use in the invention include polyethylene glycol or ammonium sulfate precipitation (see Trepanier et al., "Concentration of human respiratory syncytial virus using ammonium sulfate, polyethylene glycol or hollow fiber ultrafiltration" Journal of Virological Methods (1981) 3(4):201-211; Hagen et al., "Optimization of Poly(ethylene glycol) Precipitation of Hepatitis Virus Used to prepare VAQTA, a Highly Purified Inactivated Vaccine" Biotechnology Progress (1996) 12:406-412; and Carlsson et al., "Purification of Infectious Pancreatic Necrosis Virus by Anion Exchange Chromatography Increases the Specific Infectivity" Journal of Virological Methods (1994) 47:27-36) as well as ultrafiltration and microfiltration (see Pay et al., Developments in Biological Standardization (1985) 60:171-174; Tsurumi et al., "Structure and filtration performances of improved cuprammonium regenerated cellulose hollow fiber (improved BMM hollow fiber) for virus removal" Polymer Journal (1990) 22(12):1085-1100; and Makino et al., "Concentration of live retrovirus with a regenerated cellulose hollow fiber, BMM", Archives of Virology (1994) 139(1-2):87-96.).

Preferably, the virus is purified using chromatography, such as ion exchange chromatography. Chromatic purification allows for the production of large volumes of virus containing suspension. The viral product of interest can interact with the chromatic medium by a simple adsorption/desorption mechanism, and large volumes of sample can be processed in a single load. Contaminants that do not have affinity for the adsorbent pass through the column. The virus material can then be eluted in concentrated form.

Preferred anion exchange resins for use in the invention include DEAE, EMD TMAE. Preferred cation exchange resins may comprise a sulfonic acid-modified surface. In one embodiment, the virus is purified using ion exchange chromatography comprising a strong anion exchange resin (i.e. EMD TMAE) for the first step and EMD-$SO_3$ (cation exchange resin) for the second step. A metal-binding affinity chromatography step can optionally be included for further purification. (See, e.g., WO 97/06243).

A preferred resin for use in the invention is Fractogel® EMD. This synthetic methacrylate based resin has long, linear polymer chains (so-called "tentacles") covalently attached. This "tentacle chemistry" allows for a large amount of sterically accessible ligands for the binding of biomolecules without any steric hindrance. This resin also has improved pressure stability.

Column-based liquid affinity chromatography is another preferred purification method for use in the invention. One example of a resin for use in this purification method is Matrex® Cellufine™ Sulfate (MCS). MCS consists of a rigid spherical (approx. 45-105 µm diameter) cellulose matrix of 3,000 Dalton exclusion limit (its pore structure excludes macromolecules), with a low concentration of sulfate ester functionality on the 6-position of cellulose. As the functional ligand (sulfate ester) is relatively highly dispersed, it presents insufficient cationic charge density to allow for most soluble proteins to adsorb onto the bead surface. Therefore the bulk of the protein found in typical virus pools (cell culture supernatants, i.e. pyrogens and most contaminating proteins, as well as nucleic acids and endotoxins) are washed from the column and a degree of purification of the bound virus is achieved.

Additional purification methods which may be used to purify inactivated virus include the use of a nucleic acid degrading agent, preferably a nucleic acid degrading enzyme, such as a nuclease having DNase and RNase activity, or an endonuclease, such as from *Serratia marcescens*, commercially available as Benzonase®, membrane adsorbers with anionic functional groups (e.g. Sartobind®) or additional chromatographic steps with anionic functional groups (e.g. DEAE or TMAE). An ultrafiltration/dialfiltration and final sterile filtration step could also be added to the purification method. Preferably, the purification includes treatment of the viral preparation with one or more nucleic acid degrading enzymes. These enzymes may be used to reduce the level of host cell nucleic acid in the viral purification process. Nucleic acid digesting enzymes for use in cell culture are known in the art and include, for example, Benzonase®.

The purified viral preparation of the invention is substantially free of contaminating proteins derived from the cells or cell culture and preferably comprises less than about 50 pg cellular nucleic acid/µg virus antigen. Still more preferably, the purified viral preparation comprises less than about 20 pg, and even more preferably, less than about 10 pg. Methods of measuring host cell nucleic acid levels in a viral sample are known in the art. Standardized methods approved or recommended by regulatory authorities such as the WHO or the FDA are preferred.

The invention includes an inactivated vaccine composition comprising a prophylactically effective amount of viral antigen, preferably an envelope glycoprotein or an immunogenic fragment thereof. The viral antigen is preferably present in a concentration amount of 0.1 to 50 µg antigen/dose, more preferably 0.3 to 30 µg antigen/dose. Still more preferably, the antigen is about 15 µg/dose.

In one embodiment, a lower concentration of viral antigen is used in inactivated vaccine compositions of the invention. Such lower concentration vaccines may optionally comprise an adjuvant to boost the host immune response to the antigen. In such a "low dose" vaccine, the viral antigen is preferably present in a concentration of less than 15 µg antigen/dose, (i.e., less than 10, 7.5, 5 or 3 µg antigen/dose.

The inactivated vaccine preparations of the invention may further comprise a stabilizer to preserve the integrity of the immunogenic proteins in the inactivated viral preparation. Stabilizers suitable for use in vaccines are known in the art and may include, for example, buffers, sugars, sugar alcohols, and amino acids. Stabilizing buffers are preferably adjusted to a physiological pH range and may include phosphate buffers, Tris buffers, TE (Tris/EDTA), TEN (Tris/NaCl/EDTA) and Earle's salt solution. Stabilizing sugars may include, for example, one or more of saccharose, glucose, fructose, dextranes, dextranesulphate, and trehalose. Stabilizing sugar alcohols may include, for example, Xylite/Xylitole, Mannite/Mannitol, Sorbite/Sorbitol, and Glycerol. Amino acids suitable for use in the invention include, for example, L-glutamine, arginine, cysteine, and lysine. Additional stabilizers which may be used in the invention include Tartaric acid, Pluronic F 68, and Tween 80.

Viral isolates which may be used for the inactivated viral preparations of the invention may be obtained from a variety of sources, such as for example, from a clinical sample that is purified (e.g., plaque purified) or from a known repository (e.g., ATCC). Methods of viral isolation are known in the art.

Respiratory Pathogens

The compositions and methods described herein thus comprise alphavirus replicon vectors, vector constructs or replicon particles comprising nucleic acid sequences encoding proteins from one or more respiratory pathogens such as viruses, fungi and/or bacteria. For purposes of the present invention, virtually any polypeptide or polynucleotide can be used.

Antigens can be derived from any of several known respiratory pathogens (e.g., bacteria, viruses, fungi), to which an immune response is desired. Furthermore, for purposes of the present invention, an "antigen" refers to a protein that includes modifications, such as deletions, additions and substitutions (generally conservative in nature), to the native sequence, so long as the protein maintains the ability to elicit an immunological response. These modifications may be deliberate, as through site-directed mutagenesis, or may be accidental, such as through mutations of hosts that produce the antigens.

Antigens may be used alone or in any combination. The combinations may include multiple antigens from the same pathogen, multiple antigens from different pathogens or multiple antigens from the same and from different pathogens. Thus, viral antigens from different respiratory virus pathogens may be included in the same composition or may be administered to the same subject separately.

It is generally preferred that combinations of antigens be used to raise an immune response. The nucleic acids may encode immunogenic proteins derived from the same respiratory pathogen or, alternatively, may encode immunogenic proteins derived from different respiratory pathogens. If the nucleic acids encoding the immunogenic proteins are derived from the same respiratory pathogen, it is preferred, but not required, that the nucleic acids be included in different alphavirus vectors or particles. Furthermore, when the nucleic acids encode immunogenic proteins derived from the same respiratory pathogen, the nucleic acids may be derived from the same or different strains.

Thus, the immunogenic compositions and vaccines described herein are intended to provide a more optimal or complete protection against respiratory pathogens, as well as increase the breadth of the protective immune response(s).

Non-limiting examples of viral respiratory pathogens of the present invention include the Orthomyxoviridae (e.g., influenza virus types A, B and C, etc. as described in Chapter 19 of *Vaccines*, 1998, eds. Plotkin & Mortimer (ISBN 0-7216-1946-0); Paramyxoviridae (e.g., parainfluenza virus, respiratory syncytial virus, human metapneumovirus, etc. as described in Chapters 9 to 11 of *Vaccines*, 1998, eds. Plotkin & Mortimer (ISBN 0-7216-1946-0); Coronaviridae (e.g., SARS coronavirus, Rota et al., 2003, Science 300:1394-1399); Picornaviridae (e.g., rhinovirus) influenza virus (Kawaoka et al., *Virology* (1990) 179:759-767; Webster et al., "Antigenic variation among type A influenza viruses," p. 127-168. In: P. Palese and D. W. Kingsbury (ed.), Genetics of influenza viruses. Springer-Verlag, New York).

Non-limiting examples of bacterial respiratory pathogens of the present invention include *Mycobacterium tuberculosis*; *Corynebacterium diphtheriae*; *Bordatella pertussis*; *Streptococcus pneumoniae* (e.g., a saccharide or protein antigen, particularly a saccharide from *Streptooccus pneumoniae*); nontypeable *Haemophilus influenzae*; *Moraxella catarrhalis*; *Pseudomonas aeruginosa*; *Bacillus anthracis* (anthrax) and *Legionella pneumophila* (Legionnaires' Disease).

Non-limiting examples of fungal respiratory pathogens include *Coccidioides immitis* (causative agent of Valley Fever), *Cryptococcosis* spp. (e.g., *Cryptococcus neoformans*), *Candida* spp. (e.g., *Candida albicans*), and *Aspergillus* spp.

A. Respiratory Syncytial Virus

Respiratory syncytial virus is the most common cause of bronchiolitis and pneumonia among infants and children under 1 year of age. Illness begins most frequently with fever, runny nose, cough, and sometimes wheezing. During their first RSV infection, between 25% and 40% of infants and young children have signs or symptoms of bronchiolitis or pneumonia, and 0.5% to 2% require hospitalization. Most children recover from illness in 8 to 15 days. The majority of children hospitalized for RSV infection are under 6 months of age. RSV also causes repeated infections throughout life, usually associated with moderate-to-severe cold-like symptoms; however, severe lower respiratory tract disease may occur at any age, especially among the elderly or among those with compromised cardiac, pulmonary, or immune systems.

RSV is a negative-sense, single-stranded RNA virus, belonging to the family Paramyxoviridae, and possesses multiple, well characterized target antigens for vaccine applications, such as the attachment (G) and fusion (F) glycoprotein "spikes" on its surface (Johnson et al., (1987) *J. Virol.*, 61:3163-3166). In addition to the G and F antigens, other RSV genes encoding polypeptides useful in the present invention include matrix protein (M), SH protein, nucleocapsid protein (N), P, L, M2-1 and M2-2 (see for example, GenBank accession No. M74568 and NC 001781; Wertz, et al. 1985 Proc. Natl. Acad. Sci. USA 82, 4075-4079; Johnson et al., (1988) *J. Gen. Virol.* 69:2623-2628; Johnson et al., (1987) Proc. Natl. Acad. Sci. USA 84:5625-5629; Collins et al., (1984) Proc. Natl., Acad. Sci USA 81:7683-7687; Collins et al., (1990) J. Gen. Virol. 71:3015-3020).

B. Parainfluenza

Human parainfluenza viruses (HPIVs) are second to RSV as a common cause of lower respiratory tract disease in young children. Similar to RSV, HPIVs can cause repeated infections throughout life, usually manifested by an upper respiratory tract illness (e.g., a cold and/or sore throat). HPIVs can also cause serious lower respiratory tract disease with repeat infection (e.g., pneumonia, bronchitis, and bronchiolitis), especially among the elderly, and among patients with compromised immune systems.

Each of the four HPIVs has different clinical and epidemiologic features. The most distinctive clinical feature of HPIV-1 and -2 is croup (i.e., laryngotracheobronchitis); HPIV-1 is the leading cause of croup in children, whereas HPIV-2 is less frequently detected. Both HPIV-1 and -2 can cause other upper and lower respiratory tract illnesses. HPIV-3 is more often associated with bronchiolitis and pneumonia. HPIV-4 is infrequently detected, possibly because it is less likely to cause severe disease.

PIVs are negative-sense, single-stranded RNA viruses belonging to the family Paramyxoviridae, which possess fusion (F) and hemagglutinin-neuraminidase (HN) glycoprotein "spikes" on their surface. There are four serotypes types of HPIV (1 through 4) and two subtypes (4a and 4b). In addition to the F and HN antigens, other PIV genes encoding polypeptides useful in the present invention include matrix protein (M), nucleocapsid (NP), phosphoprotein (P), L, accessory proteins V, C, D, W, X and I (see for example GenBank accession #Z11575, NC 001796, AF533012, and U51116, and Stokes, et al., 1992 Virus Res. 25:91-103).

C. Human Metapneumovirus

Human metapneumovirus is a recently discovered respiratory pathogen also of the family Paramyxoviridae belonging to the same subfamily, Pneumovirinae, as respiratory syncytial virus. HMPV was first recognized in the Netherlands in 2001 in nasopharyngeal aspirate samples collected from children over a 20-year period. It has since been identified in many countries throughout the world. Recent reports investigating HMPV have shown that HMPV-infected children who are hospitalized with respiratory illness frequently have clinical diagnoses of bronchiolitis and pneumonia, much like children infected with RSV. Clinical symptoms from HMPV-infected children have included nonproductive cough, nasal congestion, and wheezing. The most commonly reported abnormality on chest radiography was bilateral infiltrates, indicative of pneumonia. Recent studies have associated human metapneumovirus (HMPV) infection in children with respiratory disease of similar severity as respiratory syncytial virus (RSV) infection.

Similar to RSV and PIV, HMPV has multiple antigen targets useful in the immunogenic compositions described herein, including the envelope G glycoprotein (G) and fusion protein (F), matrix protein (M), nucleocapsid protein (N), SH protein, P, L, and M2 (see, for example Van Den Hoogen et al 2001, Nature Med. 7:719-724: and GenBank Accession #AF371337; Crowe (2004) *Pediatr. Infect. Dis. J.*, 23:S215-221).

D. SARS

Severe acute respiratory syndrome (SARS) is a viral respiratory illness caused by a coronavirus, called SARS-associated coronavirus (SARS-CoV). SARS was first reported in Asia in February 2003. Over the next few months, the illness spread to more than two dozen countries in North America, South America, Europe, and Asia before the SARS global outbreak of 2003 was contained. According to the World Health Organization (WHO), a total of 8,098 people worldwide became sick with SARS during the 2003 outbreak. Of these, 774 died. In general, SARS begins with a high fever (temperature greater than 100.4° F. [>38.0° C.]). Other symptoms may include headache, an overall feeling of discomfort, and body aches. Some people also have mild respiratory symptoms at the outset. About 10 percent to 20 percent of patients have diarrhea. After 2 to 7 days, SARS patients may develop a dry cough. Most patients develop pneumonia.

SARS-CoV, like other coronaviruses, is a large positive strand RNA viruses with multiple antigen targets, including the spike glycoprotein (S) (Song et al., (2004) *J. Virol.* 78:10328-10335). SARS-CoV genes encoding polypeptides useful for the present invention include, for example Spike glycoprotein (S), E, M, N, ORF1a, ORF1b, and a variety of relatively small proteins of less defined function (Rota et al., 2003, Science 300:1394-1399; Marra et al., 2003, Science 300:1399-1404; Ruan et al., 2003, Lancet 361:1779-1785; Eickmann et al., 2003, Science 302:1504-1505). SARS polypeptides are also described in WO 04/092360.

E. Influenza

Influenza viruses include three different types: A, B, and C. Influenza type A viruses are divided into subtypes based on two proteins on the surface of the virus, hemagglutinin (HA) and neuraminidase (NA). There are 15 different HA subtypes and 9 different NA subtypes. The viruses are classified according to their surface proteins. For example, an "H7N2 virus" designates an influenza A subtype that has a hemagglutinin 7 protein and a neuraminidase 2 protein. Wild birds are the natural host to all subtypes of influenza A viruses. Influenza B and certain subtypes of influenza A (H1N1, H1N2 and H3N2) normally circulate among humans and cause yearly epidemics of disease. Type C influenza viruses are milder and do not cause epidemics. Type A viruses historically have been the ones responsible for influenza pandemics.

Influenza viruses include pandemic, emerging pandemic and future pandemic human strains. The characteristics of an influenza strain that give it the potential to cause a pandemic outbreak are: (a) it contains a new hemagglutinin compared to the hemagglutinins in currently-circulating human strains, i.e. one that has not been evident in the human population for over a decade (e.g. H2), or are rarely seen in the human population (e.g. H5, H7 or H9, that have generally been found only in bird populations), such that the human population will be immunologically naïve to the strain's hemagglutinin; (b) it is capable of being transmitted horizontally in the human population; and (c) it is pathogenic to humans.

Uncomplicated influenza illness is characterized by the abrupt onset of constitutional and respiratory signs and symptoms (e.g., fever, myalgia, headache, severe malaise, nonproductive cough, sore throat, and rhinitis). Among children, otitis media, nausea, and vomiting are also commonly reported with influenza illness. Respiratory illness caused by influenza is difficult to distinguish from illness caused by other respiratory pathogens on the basis of symptoms alone. Influenza illness typically resolves after a limited number of days for the majority of persons, although cough and malaise can persist for >2 weeks. Among certain persons, influenza can exacerbate underlying medical conditions (e.g., pulmonary or cardiac disease), lead to secondary bacterial pneumonia or primary influenza viral pneumonia, or occur as part of a coinfection with other viral or bacterial pathogens. Young children with influenza infection can have initial symptoms mimicking bacterial sepsis with high fevers, and ≤20% of children hospitalized with influenza can have febrile seizures Influenza infection has also been associated with encephalopathy, transverse myelitis, Reye syndrome, myositis, myocarditis, and pericarditis.

The risks for complications, hospitalizations, and deaths from influenza are higher among persons aged ≥65 years, young children, and persons of any age with certain underlying health conditions (see Persons at Increased Risk for Complications) than among healthy older children and younger adults. Influenza-related deaths can result from pneumonia as well as from exacerbations of cardiopulmonary conditions and other chronic diseases. Older adults account for ≥90% of deaths attributed to pneumonia and influenza.

In addition to those influenza viruses that normally infect humans, avian influenza viruses that are typically genetically distinguishable from influenza viruses that normally infect people and cause varying degrees of illness in poultry also are contemplated in the present invention. Birds that are infected with avian influenza viruses shed virus in saliva, nasal secretions and feces. Disease spreads when susceptible birds have contact with contaminated excretions. While avian influenza A viruses do not usually infect humans, several instances of human infections and outbreaks of avian influenza have been reported since 1997. It is believed that most cases of avian influenza infection in humans have resulted from contact with infected poultry or contaminated surfaces. An example of an avian influenza virus reported to infect humans is H7 influenza virus, which circulates among birds worldwide and can be deadly, particularly to domesticated birds such as chickens and other poultry. In 2003, however, the Netherlands reported outbreaks of influenza A (H7N7) in poultry on several farms. Later, infections were reported among pigs and humans. In total, 83 people were confirmed to have H7N7 influenza virus infection associated with this poultry outbreak. These cases occurred mostly among poultry workers. The state of Delaware also reported an outbreak of avian influenza A (H7N2) among poultry. Affected poultry are being culled and quarantine measures have been instituted. This H7N2 virus is significantly different from the H7N7 virus. Outbreaks of influenza A (H5N1) are currently occurring among bird populations in countries throughout Asia and in humans in Thailand and Vietnam. H5N1 avian influenza viruses have previously caused human illness in Hong Kong in 1997 (18 cases) and in 2 people from Hong Kong who traveled to China in 2003. Preferred FLU antigens of the present invention include the surface glycoproteins hemagglutinin (HA) and neuraminidase (NA).

A variety of influenza subtypes are the source of target antigens contemplated by the present invention, including for example those with an H1, H2, H3, H4, H5, H6, H7, H8, H9, H10, H11, H12, H13, H14, or H15 hemagglutinin and N1, N2, N3, N4, N5, N6, N7, N8, and N9 neuraminidase (e.g., H7N7, H7N2, H5N1, H5N2, H3N2, H1N1, H2N2, H3N8 strains). FLU gene encoding antigens of the present invention include hemagglutinin (HA), neuraminidase (NA), nucleocapsid (NP), matrix protein ($M_1$), ion channel protein ($M_2$), $NS_1$, $NS_2$, $PB_1$, $PB_2$, and PA (see for Lamb et al., 2001, Fields Virology, Knipe and Howley, eds., pp. 1487-1532, Lippincott, Williams and Wilkins; Wright et al., 2001, Fields Virology, Knipe and Howley, eds., pp. 1533-1579, Lippincott, Williams and Wilkins).

As noted above, one or more influenza proteins (antigens) can be encoded by one or more alphavirus constructs or particles as described herein. In certain embodiments, described herein are compositions comprising a first alphavirus construct or particle comprising one FLU antigen (HA and/or NA). Alternatively, in other embodiments, the immunogenic compositions comprise multiple influenza antigens (e.g., HA and/or NA) (either in the same particle or in different constructs or particles) where the antigens are derived from multiple pandemic or potentially pandemic influenza strains. The compositions are used to generate a protective and/or therapeutic immune response in a subject against infection by pandemic or potential pandemic influenza strains and interpandemic influenza strains or to provide a "universal" flu vaccine.

Multiple influenza proteins (antigens) can be encoded by one or more alphavirus constructs or particles encoding multiple influenza antigens (e.g., HA and/or NA) (either in the same particle or in different constructs or particles) where the antigens are derived from multiple pandemic or potentially pandemic influenza strains. The compositions are used to generate a protective and/or therapeutic immune response in a subject against infection by pandemic or potential pandemic influenza strains or to provide a "universal" pandemic flu vaccine.

Similarly, one or more constructs or particles comprising sequences encoding multiple FLU proteins (e.g., NA and/or HA proteins) (either in the same particle or in different constructs or particles) from interpandemic influenza strains can be generated in order to provide immunogenic compositions (e.g., vaccines) having a broader range of antigens than traditional egg-based FLU vaccines (which are limited by supply of egg) or to provide a universal vaccine which would not need to be reformulated annually and/or help in preventing antigenic shift.

F. Bacterial Respiratory Pathogens

The respiratory bacterial pathogens, from which the nucleic acids encoding the immunogenic proteins can be derived, include but are not limited to: *Mycobacterium tuberculosis* (e.g., lipoproteins, LPS, BCG antigens, a fusion protein of antigen S5B (AgS5B) and/or ESAT-6 optionally formulated in cationic lipid vesicles (Infect Immun. 2004

October; 72(10): 6148), *Mycobacterium tuberculosis* (Mtb) isocitrate dehydrogenase associated antigens (*Prot Natl Acad Sci USA.* 2004 Aug. 24; 101(34): 12652), and/or MPT51 antigens (Infect Immun. 2004 July; 72(7): 3829); *Corynebacterium diphtheriae; Bordatella pertussis; Streptococcus pneumoniae* (e.g., a saccharide or protein antigen, particularly a saccharide from *Streptooccus pneumoniae*); nontypeable *Haemophilus influenzae; Moraxella catarrhalis* (e.g., outer membrane protein antigens (HMW-OMP), C-antigen, and/or LPS); *Pseudomonas aeruginosa* (e.g., endotoxin A, Wzz protein, *P. aeruginosa* LPS, more particularly LPS isolated from PAO1 (O5 serotype), and/or Outer Membrane Proteins, including Outer Membrane Proteins F (OprF) (*Infect Immun.* 2001 May; 69(5): 3510-3515); *Bacillus anthracis* (anthrax) (e.g., *B. anthracis* antigens (optionally detoxified) from A-components (lethal factor (LF) and edema factor (EF)), both of which may share a common B-component known as protective antigen (PA)); and/or *Legionella pneumophila* (Legionnaires' Disease): *L. pneumophila* antigens—optionally derived from cell lines with disrupted asd genes (*Infect Immun.* 1995 May; 66(5): 1898).

Where not specifically referenced, further bacterial antigens of the invention may be capsular antigens, polysaccharide antigens or protein antigens of any of the above. Further bacterial antigens may also include an outer membrane vesicle (OMV) preparation. Additionally, antigens include live, attenuated, split, and/or purified versions of any of the aforementioned bacteria. The bacterial or microbial derived antigens of the present invention may be gram-negative or gram-positive and aerobic or anaerobic.

Additionally, any of the above bacterial-derived saccharides (polysaccharides, LPS, LOS or oligosaccharides) can be conjugated to another agent or antigen, such as a carrier protein (for example $CRM_{197}$). Such conjugation may be direct conjugation effected by reductive amination of carbonyl moieties on the saccharide to amino groups on the protein, as provided in U.S. Pat. No. 5,360,897 and *Can J Biochem Cell Biol.* 1984 May; 62(5):270-5. Alternatively, the saccharides can be conjugated through a linker, such as, with succinamide or other linkages provided in *Bioconjugate Techniques,* 1996 and *CRC, Chemistry of Protein Conjugation and Cross-Linking,* 1993.

G. Fungal Respiratory Pathogens

The respiratory fungal pathogens, from which the nucleic acids encoding the immunogenic proteins can be derived, include but are not limited to: *Coccidioides* spp. including *Coccidioides immiti,* the causative agent of Valley Fever (antigen-2 or proline rich antigen (Ag2/PRA) (Silva et al. (2005) FEMS Immunol Med Microbiol. 2005 43(3):393-8)); *Cryptococcosis* spp. such *Cryptococcus neoformans* (e.g., Cryptococcal antigen (Liaw et al. (1998) *J Clin Microbiol.* 33(6):1588-91)), *Candida* spp. *Candida albicans*), and *Aspergillus* spp.

Respiratory fungal antigens from which the nucleic acids encoding the immunogenic proteins can be derived include fungal antigens that cause a respiratory disorder following inhalation or sensitization.

H. Combinations

As noted above, the immunogenic composition preferably comprises nucleic acid encoding two or more immunogenic proteins from at least one respiratory pathogen. The immunogenic compositions can include any combination of proteins described herein. In addition, the nucleic acids encoding the immunogenic proteins may be included in different alphavirus vector constructs or replicon particles, for example, when the immunogenic proteins are derived from PIV, RSV or SARS. For instance, if the composition includes two nucleic acids encoding the same or different PIV proteins, it may be preferably that the two nucleic acids are included in separate alphavirus constructs or particles. Similarly, if the composition includes two nucleic acids encoding the same or different SARS proteins or the same or different RSV proteins, it may be preferably that the two nucleic acids are included in separate alphavirus constructs or particles.

The invention also encompasses nucleic acids encoding multiple immunogenic proteins that are included in the same alphavirus vector construct or replicon particle.

H. Cell Lines

The antigens from respiratory pathogens can be produced in a variety of different expression systems known in the art; for example those used with mammalian cells, avian cells, baculoviruses, bacteria, and yeast. Such expression systems will typically use polynucleotides encoding the immunogenic proteins. Such sequences can be obtained using standard techniques of molecular biology, including translating the amino acid sequences listed herein. Accordingly, the invention includes polynucleotides encoding for the viral antigens of the invention. In addition, the viral antigens of the invention can be produced (at least in part, preferably in whole) via synthetic chemistry methods.

Insect cell expression systems, such as baculovirus systems, are known to those of skill in the art and described in, e.g., Summers and Smith, *Texas Agricultural Experiment Station Bulletin* No. 1555 (1987). Materials and methods for baculovirus/insect cell expression systems are commercially available in kit form from, inter alia, Invitrogen, San Diego Calif. Avian cell expression systems are also known to those of skill in the art and described in, e.g., U.S. Pat. Nos. 5,340,740; 5,656,479; 5,830,510; 6,114,168; and 6,500,668; European Patent No. EP 0787180B; European Patent Application No. EP03291813.8; WO 03/043415; and WO 03/076601. Similarly, bacterial and mammalian cell expression systems are also known in the art and described in, e.g., *Yeast Genetic Engineering* (Barr et al., eds., 1989) Butterworths, London.

A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (e.g., Hep G2), Madin-Darby bovine kidney ("MDBK") cells, as well as others. Mammalian sources of cells include, but are not limited to, human or non-human primate (e.g., PERC.6 cells which are described, for example, in WO 01/38362 and WO 02/40665, incorporated by reference herein in their entireties, as well as deposited under ECACC deposit number 96022940), MRC-5 (ATCC CCL-171), WI-38 (ATCC CCL-75), fetal rhesus lung cells (ATCC CL-160), human embryonic kidney cells (293 cells, typically transformed by sheared adenovirus type 5 DNA), VERO cells from monkey kidneys), horse, cow (e.g., MDBK cells), sheep, dog (e.g., MDCK cells from dog kidneys, ATCC CCL34 MDCK (NBL2) or MDCK 33016, deposit number DSM ACC 2219 as described in WO 97/37001), cat, and rodent (e.g., hamster cells such as BHK21-F, HKCC cells, or Chinese hamster ovary cells (CHO cells)), and may be obtained from a wide variety of developmental stages, including for example, adult, neonatal, fetal, and embryo.

Avian sources of cells include, but are not limited to, chicken cells (e.g., chicken embryonic stem cells (e.g., EBx® cells), chicken embryonic fibroblasts, chicken embryonic germ cells)). Similarly, bacterial hosts such as *E. coli, Bacillus subtilis*, and *Streptococcus* spp., will find use with the present expression constructs. Yeast hosts useful in the present invention include, inter alia, *Saccharomyces cerevisiae, Candida albicans, Candida maltosa, Hansenual polymorpha, Kluyveromyces fragilis, Kluyveromyces lactis, Pichia guillerimondii, Pichia pastoris, Schizosaccharomyces pombe* and *Yarrowia lipodytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Pharmaceutical Compositions

The present invention also provides pharmaceutical compositions comprising any of the alphavirus replicon particles, vectors and/or replicons, and inactivated viruses as described herein in combination with a pharmaceutically acceptable carrier, diluent, or excipient. The present invention contemplates that procedures described above for inactivated virus vaccines also may be applicable to alphavirus vectors (e.g., replicon particles). Within certain preferred embodiments, a sufficient amount of formulation buffer is added to the purified replicon particles to form an aqueous suspension. In preferred embodiments, the formulation buffer comprises a saccharide and a buffering component in water, and may also contain one or more amino acids or a high molecular weight structural additive. The formulation buffer is added in sufficient amount to reach a desired final concentration of the constituents and to minimally dilute the replicon particles. The aqueous suspension may then be stored, preferably at −70° C., or immediately dried.

The aqueous suspension can be dried by lyophilization or evaporation at ambient temperature. Briefly, lyophilization involves the steps of cooling the aqueous suspension below the gas transition temperature or below the eutectic point temperature of the aqueous suspension, and removing water from the cooled suspension by sublimation to form a lyophilized replicon particle. Within one embodiment, aliquots of the formulated recombinant virus are placed into an Edwards Refrigerated Chamber (3 shelf RC3S unit) attached to a freeze dryer (Supermodulyo 12K). A multistep freeze drying procedure as described by Phillips et al. (*Cryobiology* 18:414, 1981) is used to lyophilize the formulated replicon particles, preferably from a temperature of −40° C. to −45° C. The resulting composition contains less than 10% water by weight of the lyophilized replicon particles. Once lyophilized, the replicon particles are stable and may be stored at −20° C. to 25° C., as discussed in more detail below. In the evaporative method, water is removed from the aqueous suspension at ambient temperature by evaporation. Within one embodiment, water is removed by a spray-drying process, wherein the aqueous suspension is delivered into a flow of preheated gas, usually which results in the water rapidly evaporating from droplets of the suspension. Once dehydrated, the recombinant virus is stable and may be stored at −20° C. to 25° C.

The aqueous solutions used for formulation preferably comprise a saccharide, a buffering component, and water. The solution may also include one or more amino acids and a high molecular weight structural additive. This combination of components acts to preserve the activity of the replicon particles upon freezing and also lyophilization or drying through evaporation. Although a preferred saccharide is lactose, other saccharides may be used, such as sucrose, mannitol, glucose, trehalose, inositol, fructose, maltose or galactose. A particularly preferred concentration of lactose is 3%-4% by weight.

The high molecular weight structural additive aids in preventing particle aggregation during freezing and provides structural support in the lyophilized or dried state. Within the context of the present invention, structural additives are considered to be of "high molecular weight" if they are greater than 5000 M.W. A preferred high molecular weight structural additive is human serum albumin. However, other substances may also be used, such as hydroxyethyl-cellulose, hydroxymethyl-cellulose, dextran, cellulose, gelatin, or povidone. A particularly preferred concentration of human serum albumin is 0.1% by weight.

The buffering component acts to buffer the solution by maintaining a relatively constant pH. A variety of buffers may be used, depending on the pH range desired, preferably between 7.0 and 7.8. Suitable buffers include phosphate buffer and citrate buffer. In addition, it is preferable that the aqueous solution contains a neutral salt that is used to adjust the final formulated replicon particles to an appropriate iso-osmotic salt concentration. Suitable neutral salts include sodium chloride, potassium chloride or magnesium chloride. A preferred salt is sodium chloride. The lyophilized or dehydrated replicon particles of the present invention may be reconstituted using a variety of substances, but are preferably reconstituted using water. In certain instances, dilute salt solutions that bring the final formulation to isotonicity may also be used.

A. Adjuvants

Immunogenic compositions (e.g., vaccines) of the invention may be administered in conjunction with other immunoregulatory agents. In particular, compositions will usually include an adjuvant. Adjuvants for use with the invention include, but are not limited to, one or more of the following set forth below:

A. Mineral Containing Compositions

Mineral containing compositions suitable for use as adjuvants in the invention include mineral salts, such as aluminum salts and calcium salts. The invention includes mineral salts such as hydroxides (e.g. oxyhydroxides), phosphates (e.g. hydroxyphosphates, orthophosphates), sulfates, etc. (e.g. see chapters 8 & 9 of *Vaccine Design* . . . (1995) eds. Powell & Newman. ISBN: 030644867X. Plenum.), or mixtures of different mineral compounds (e.g. a mixture of a phosphate and a hydroxide adjuvant, optionally with an excess of the phosphate), with the compounds taking any suitable form (e.g. gel, crystalline, amorphous, etc), and with adsorption to the salt(s) being preferred. The mineral containing compositions may also be formulated as a particle of metal salt (WO00/23105).

Aluminum salts may be included in vaccines of the invention such that the dose of $Al^{3+}$ is between 0.2 and 1.0 mg per dose.

In one embodiment the aluminum based adjuvant is alum (aluminum potassium sulfate ($AlK(SO_4)_2$)), or an alum derivative, such as that formed in-situ by mixing an antigen in phosphate buffer with alum, followed by titration and precipitation with a base such as ammonium hydroxide or sodium hydroxide.

Another aluminum-based adjuvant for use with the immunogenic compositions described herein is aluminum hydroxide adjuvant ($Al(OH)_3$) or crystalline aluminum oxyhydroxide (AlOOH), which is an excellent adsorbant, having a surface area of approximately 500 $m^2/g$. Alternatively, aluminum phosphate adjuvant ($AlPO_4$) or aluminum hydroxyphosphate, which contains phosphate groups in place of some or all of the hydroxyl groups of aluminum hydroxide adjuvant is provided. Preferred aluminum phosphate adjuvants provided herein are amorphous and soluble in acidic, basic and neutral media.

In another embodiment, the adjuvant comprises both aluminum phosphate and aluminum hydroxide. In a more particular embodiment thereof, the adjuvant has a greater amount of aluminum phosphate than aluminum hydroxide, such as a ratio of 2:1, 3:1, 4:1, 5:1, 6:1, 7:1, 8:1, 9:1 or greater than 9:1, by weight aluminum phosphate to aluminum hydroxide. More particular still, aluminum salts in the vaccine are present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the preferred aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, aluminum phosphate adjuvant (iep=4) adsorbs lysozyme, but not albumin at pH 7.4. Should albumin be the target, aluminum hydroxide adjuvant would be selected (iep 11.4). Alternatively, pretreatment of aluminum hydroxide with phosphate lowers its isoelectric point, making it a preferred adjuvant for more basic antigens.

A. Oil-Emulsions

Oil-emulsion compositions suitable for use as adjuvants include squalene-water emulsions, such as MF59 (5% Squalene, 0.5% Tween 80, and 0.5% Span 85, formulated into submicron particles using a microfluidizer). See WO90/14837. See also, Podda, "The adjuvanted influenza vaccines with novel adjuvants: experience with the MF59-adjuvanted vaccine", Vaccine (2001) 19: 2673-2680; Frey et al., "Comparison of the safety, tolerability, and immunogenicity of a MF59-adjuvanted influenza vaccine and a non-adjuvanted influenza vaccine in non-elderly adults", Vaccine (2003) 21:4234-4237. MF59 is used as the adjuvant in the FLUAD™ influenza virus trivalent subunit vaccine.

Particularly preferred adjuvants for use with the immunogenic compositions described herein are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v Tween 80™ (polyoxyelthylenesorbitan monooleate), and/or 0.25-1.0% Span 85™ (sorbitan trioleate), and, optionally, N-acetylmuramyl-L-alanyl-D-isoglutaminyl-L-alanine-2-(1'-2'-dipalmitoyl-sn-glycero-3-huydroxyphosphophoryloxy)-ethylamine (MTP-PE), for example, the submicron oil-in-water emulsion known as "MF59" (International Publication No. WO90/14837; U.S. Pat. Nos. 6,299,884 and 6,451,325, and Ott et al., "MF59—Design and Evaluation of a Safe and Potent Adjuvant for Human Vaccines" in *Vaccine Design: The Subunit and Adjuvant Approach* (Powell, M. F. and Newman, M. J. eds.) Plenum Press, New York, 1995, pp. 277-296). MF59 contains 4-5% w/v Squalene (e.g. 4.3%), 0.25-0.5% w/v Tween 80™, and 0.5% w/v Span 85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 µg/dose, more preferably 0-250 µg/dose and most preferably, 0-100 µg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 µg MTP-PE per dose, and so on. MF69, another submicron oil-in-water emulsion for use herein, contains 4.3% w/v squalene, 0.25% w/v Tween 80™, and 0.75% w/v Span 85™ and optionally MTP-PE. Yet another submicron oil-in-water emulsion is MF75, also known as SAF, containing 10% squalene, 0.4% Tween 80™, 5% pluronic-blocked polymer L121, and thr-MDP, also microfluidized into a submicron emulsion. MF75-MTP denotes an MF75 formulation that includes MTP, such as from 100-400 µg MTP-PE per dose.

Submicron oil-in-water emulsions, methods of making the same and immunostimulating agents, such as muramyl peptides, for use in the compositions, are described in detail in International Publication No. WO90/14837 and U.S. Pat. Nos. 6,299,884 and 6,451,325.

Complete Freund's adjuvant (CFA) and incomplete Freund's adjuvant (IFA) may also be used as adjuvants in the invention.

B. Saponin Formulations

Saponin formulations may also be used as adjuvants. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponins can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO96/33739).

Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP0109942, WO96/11711 and WO96/33739. Optionally, the ISCOMS may be devoid of (an) additional detergent(s), See WO00/07621.

A review of the development of saponin based adjuvants can be found in Barr, et al., "ISCOMs and other saponin based adjuvants", Advanced Drug Delivery Reviews (1998) 32:247-271. See also Sjolander, et al., "Uptake and adjuvant activity of orally delivered saponin and ISCOM vaccines", Advanced Drug Delivery Reviews (1998) 32:321-338.

C. Virosomes and Virus Like Particles (VLPs)

Virosomes and Virus Like Particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in WO03/024480, WO03/024481, and Niikura et al., "Chimeric Recombinant Hepatitis E Virus-Like Particles as an Oral Vaccine Vehicle Presenting Foreign Epitopes", Virology (2002) 293:273-280; Lenz et al., "Papillomarivurs-Like Particles Induce Acute Activation of Dendritic Cells", Journal of Immunology (2001) 5246-5355; Pinto, et al., "Cellular Immune Responses to Human Papillomavirus (HPV)-16 L1 Healthy Volunteers Immunized with Recombinant HPV-16 L1 Virus-Like Particles", Journal of Infectious Diseases (2003) 188: 327-338; and Gerber et al., "Human Papillomavirus Virus-Like Particles Are Efficient Oral Immunogens when Coadministered with *Escherichia coli* Heat-Labile Entertoxin Mutant R192G or CpG", Journal of Virology (2001) 75(10):4752-4760. Virosomes are discussed further in, for example, Gluck et al., "New Technology Platforms in the Development of Vaccines for the Future", Vaccine (2002) 20:B10-B16. Immunopotentiating reconstituted influenza virosomes (IRIV) are used as the subunit antigen delivery system in the intranasal trivalent INFLEXAL™ product {Mischler & Metcalfe (2002) *Vaccine* 20 Suppl 5:B17-23} and the INFLUVAC PLUS™ product.

D. Bacterial or Microbial Derivatives

Adjuvants suitable for use in the invention include bacterial or microbial derivatives such as:

(1) Non-toxic Derivatives of Enterobacterial Lipopolysaccharide (LPS)

Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g. RC-529. See Johnson et al. (1999) *Bioorg Med Chem Lett* 9:2273-2278.

(2) Lipid A Derivatives

Lipid A derivatives include derivatives of lipid A from *Escherichia coli* such as OM-174. OM-174 is described for example in Meraldi et al., "OM-174, a New Adjuvant with a Potential for Human Use, Induces a Protective Response with Administered with the Synthetic C-Terminal Fragment 242-310 from the circumsporozoite protein of *Plasmodium berghei*", Vaccine (2003) 21:2485-2491; and Pajak, et al., "The Adjuvant OM-174 induces both the migration and maturation of murine dendritic cells in vivo", Vaccine (2003) 21:836-842.

(3) Immunostimulatory Oligonucleotides

Immunostimulatory oligonucleotides suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpG's can include nucleotide modifications/analogs such as phosphorothioate modifications and can be double-stranded or single-stranded. Optionally, the guanosine may be replaced with an analog such as 2'-deoxy-7-deazaguanosine. See Kandimalla, et al., "Divergent synthetic nucleotide motif recognition pattern: design and development of potent immunomodulatory oligodeoxyribonucleotide agents with distinct cytokine induction profiles", Nucleic Acids Research (2003) 31(9): 2393-2400; WO02/26757 and WO99/62923 for examples of possible analog substitutions. The adjuvant effect of CpG oligonucleotides is further discussed in Krieg, "CpG motifs: the active ingredient in bacterial extracts?", Nature Medicine (2003) 9(7): 831-835; McCluskie, et al., "Parenteral and mucosal prime-boost immunization strategies in mice with hepatitis B surface antigen and CpG DNA", FEMS Immunology and Medical Microbiology (2002) 32:179-185; WO98/40100; U.S. Pat. Nos. 6,207,646; 6,239,116 and 6,429,199.

The CpG sequence may be directed to TLR9, such as the motif GTCGTT or TTCGTT. See Kandimalla, et al., "Toll-like receptor 9: modulation of recognition and cytokine induction by novel synthetic CpG DNAs", Biochemical Society Transactions (2003) 31 (part 3): 654-658. The CpG sequence may be specific for inducing a Th1 immune response, such as a CpG-A ODN, or it may be more specific for inducing a B cell response, such a CpG-B ODN. CpG-A and CpG-B ODNs are discussed in Blackwell, et al., "CpG-A-Induced Monocyte IFN-gamma-Inducible Protein-10 Production is Regulated by Plasmacytoid Dendritic Cell Derived IFN-alpha", J. Immunol. (2003) 170(8):4061-4068; Krieg, "From A to Z on CpG", TRENDS in Immunology (2002) 23(2): 64-65 and WO01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla, et al., "Secondary structures in CpG oligonucleotides affect immunostimulatory activity", BBRC (2003) 306:948-953; Kandimalla, et al., "Toll-like receptor 9: modulation of recognition and cytokine induction by novel synthetic GpG DNAs", Biochemical Society Transactions (2003) 31(part 3):664-658; Bhagat et al., "CpG penta- and hexadeoxyribonucleotides as potent immunomodulatory agents" BBRC (2003) 300:853-861 and WO03/035836.

(4) ADP-ribosylating Toxins and Detoxified Derivatives Thereof.

Bacterial ADP-ribosylating toxins and detoxified derivatives thereof may be used as adjuvants in the invention. Preferably, the protein is derived from *E. coli* (i.e., *E. coli* heat labile enterotoxin "LT"), cholera ("CT"), or pertussis ("PT"). The use of detoxified ADP-ribosylating toxins as mucosal adjuvants is described in WO95/17211 and as parenteral adjuvants in WO98/42375. Preferably, the adjuvant is a detoxified LT mutant such as LT-K63, LT-R72, and LTR192G. The use of ADP-ribosylating toxins and detoxified derivatives thereof, particularly LT-K63 and LT-R72, as adjuvants can be found in the following references: Beignon, et al., "The LTR72 Mutant of Heat-Labile Enterotoxin of *Escherichia coli* Enhances the Ability of Peptide Antigens to Elicit CD4+ T Cells and Secrete Gamma Interferon after Coapplication onto Bare Skin", Infection and Immunity (2002) 70(6):3012-3019; Pizza, et al., "Mucosal vaccines: non toxic derivatives of LT and CT as mucosal adjuvants", Vaccine (2001) 19:2534-2541; Pizza, et al., "LTK63 and LTR72, two mucosal adjuvants ready for clinical trials" Int. J. Med. Microbiol (2000) 290(4-5):455-461; Scharton-Kersten et al., "Transcutaneous Immunization with Bacterial ADP-Ribosylating Exotoxins, Subunits and Unrelated Adjuvants", Infection and Immunity (2000) 68(9):5306-5313; Ryan et al., "Mutants of *Escherichia coli* Heat-Labile Toxin Act as Effective Mucosal Adjuvants for Nasal Delivery of an Acellular Pertussis Vaccine: Differential Effects of the Nontoxic AB Complex and Enzyme Activity on Th1 and Th2 Cells" Infection and Immunity (1999) 67(12):6270-6280;

Partidos et al., "Heat-labile enterotoxin of *Escherichia coli* and its site-directed mutant LTK63 enhance the proliferative and cytotoxic T-cell responses to intranasally co-immunized synthetic peptides", Immunol. Lett. (1999) 67(3):209-216; Peppoloni et al., "Mutants of the *Escherichia coli* heat-labile enterotoxin as safe and strong adjuvants for intranasal delivery of vaccines", Vaccines (2003) 2(2):285-293; and Pine et al., (2002) "Intranasal immunization with influenza vaccine and a detoxified mutant of heat labile enterotoxin from *Escherichia coli* (LTK63)" J. Control Release (2002) 85(1-3):263-270. Numerical reference for amino acid substitutions is preferably based on the alignments of the A and B subunits of ADP-ribosylating toxins set forth in Domenighini et al., Mol. Microbiol (1995) 15(6):1165-1167.

E. Bioadhesives and Mucoadhesives

Bioadhesives and mucoadhesives may also be used as adjuvants. Suitable bioadhesives include esterified hyaluronic acid microspheres (Singh et al. (2001) *J. Cont. Rele.* 70:267-276) or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants. See, e.g. WO99/27960.

F. Microparticles

Microparticles may also be used as adjuvants. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly (□-hydroxy acid), a polyhydroxybutyric acid, a polyorthoester, a polyanhydride, a polycaprolactone, etc.), with poly (lactide-co-glycolide) are preferred, optionally treated to have a negatively-charged surface (e.g. with SDS) or a positively-charged surface (e.g. with a cationic detergent, such as CTAB).

G. Liposomes

Examples of liposome formulations suitable for use as adjuvants are described in U.S. Pat. Nos. 6,090,406, 5,916,588, and EP 0 626 169.

H. Polyoxyethylene ether and Polyoxyethylene Ester Formulations

Adjuvants suitable for use with the immunogenic compositions described herein include polyoxyethylene ethers and polyoxyethylene esters. WO99/52549. Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152).

Preferred polyoxyethylene ethers are selected from the following group; polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

I. Polyphosphazene (PCPP)

PCPP formulations are described, for example, in Andrianov et al., "Preparation of hydrogel microspheres by coacervation of aqueous polyphophazene solutions", Biomaterials (1998) 19(1-3):109-115 and Payne et al., "Protein Release from Polyphosphazene Matrices", Adv. Drug. Delivery Review (1998) 31(3):185-196.

J. Muramyl Peptides

Examples of muramyl peptides suitable for use as adjuvants in the invention include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-sn-glycero-3-hydroxyphosphoryloxy)-ethylamine MTP-PE).

K. Imidazoquinoline Compounds.

Examples of imidazoquinoline compounds suitable for use adjuvants in the invention include Imiquimod and its analogues, described further in Stanley, "Imiquimod and the imidazoquinolines: mechanism of action and therapeutic potential" Clin Exp Dermatol (2002) 27(7):571-577; Jones, "Resiquimod 3M", Curr Opin Investig Drugs (2003) 4(2): 214-218; and U.S. Pat. Nos. 4,689,338, 5,389,640, 5,268, 376, 4,929,624, 5,266,575, 5,352,784, 5,494,916, 5,482,936, 5,346,905, 5,395,937, 5,238,944, and 5,525,612.

L. Thiosemicarbazone Compounds.

Examples of thiosemicarbazone compounds, as well as methods of formulating, manufacturing, and screening for compounds all suitable for use as adjuvants in the invention include those described in WO04/60308. The thiosemicarbazones are particularly effective in the stimulation of human peripheral blood mononuclear cells for the production of cytokines, such as TNF-•.

M. Tryptanthrin Compounds.

Examples of tryptanthrin compounds, as well as methods of formulating, manufacturing, and screening for compounds all suitable for use as adjuvants in the invention include those described in WO04/64759. The tryptanthrin compounds are particularly effective in the stimulation of human peripheral blood mononuclear cells for the production of cytokines, such as TNF-•.

The invention may also comprise combinations of aspects of one or more of the adjuvants identified above. For example, the following adjuvant compositions may be used in the invention:

(1) a saponin and an oil-in-water emulsion (WO99/11241);

(2) a saponin (e.g., QS21)+a non-toxic LPS derivative (e.g. 3dMPL) (see WO94/00153);

(3) a saponin (e.g., QS21)+a non-toxic LPS derivative (e.g. 3dMPL)+a cholesterol;

(4) a saponin (e.g. QS21)+3dMPL+IL-12 (optionally+a sterol) (WO98/57659);

(5) combinations of 3dMPL with, for example, QS21 and/or oil-in-water emulsions (See European patent applications 0835318, 0735898 and 0761231);

(6) SAF, containing 10% Squalane, 0.4% Tween 80, 5% pluronic-block polymer L121, and thr-MDP, either microfluidized into a submicron emulsion or vortexed to generate a larger particle size emulsion.

(7) Ribi™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dPML).

(9) one or more mineral salts (such as an aluminum salt)+an immunostimulatory oligonucleotide (such as a nucleotide sequence including a CpG motif).

N. Human Immunomodulators

Human immunomodulators suitable for use as adjuvants in the invention include cytokines, such as interleukins (e.g. IL-1, IL-2, IL-4, IL-5, IL-6, IL-7, IL-12, etc.), interferons (e.g. interferon-macrophage colony stimulating factor, and tumor necrosis factor.

Aluminum salts and MF59 are preferred adjuvants for use with injectable influenza vaccines. Bacterial toxins and bioadhesives are preferred adjuvants for use with mucosally-delivered vaccines, such as nasal vaccines.

The contents of all of the above cited patents, patent applications and journal articles are incorporated by reference as if set forth fully herein.

Applications

The alphavirus replicons, replicon particles and vector constructs can be used to deliver a wide variety of nucleotide sequences including, for example, heterologous sequences which encode antigens from respiratory pathogens, which stimulate an immune response. The above nucleotide sequences include those referenced previously, and may be obtained from repositories, readily cloned from viral or other RNA using published sequences, or synthesized, for example, on an Applied Biosystems Inc. DNA synthesizer (e.g., APB DNA synthesizer model 392 (Foster City, Calif.)).

The present invention also provides methods for delivering these selected heterologous sequences to a warm-blooded mammal (e.g., a mammal such as a human or other warm-blooded animal such as a horse, cow, pig, sheep, dog, cat, rat or mouse) for use as a vaccine or therapeutic, comprising the step of administering to the mammal replicon particles, replicon vectors, vector constructs or Eukaryotic Layered Vector Initiation Systems as described herein, which are capable of expressing the selected heterologous sequence. Delivery may be by a variety of routes (e.g., intravenously, intramuscularly, intradermally, subcutaneously, orally, intranasally).

It should be noted that the preferred method for production of alphavirus replicon particles of the present invention should use techniques known in the art to minimize the possibility of generating contaminating replication-competent virus (RCV). One such strategy is the use of defective helpers or PCL that contain "split" structural protein expression cassettes (see U.S. Pat. Nos. 5,789,245; 6,242,259; 6,329,201). In this context, the alphavirus structural protein genes are segregated into separate expression constructs (e.g., capsid separate from glycoproteins) such that recombination to regenerate a complete complement of expressed structural proteins is highly unlikely.

The following examples are included to more fully illustrate the present invention. Additionally, these examples provide preferred embodiments of the invention and are not meant to limit the scope thereof.

EXAMPLES

Example 1

Construction of Alphavirus Replicon Vectors Containing Influenza Virus HA, NA or NP Antigen Encoding Genes The influenza virus strains A/Panama/2007/99 Resvir-17 (H3N2) (recommended vaccine strain for production in 2000-2003) and WS/33 (H1N1) were obtained from the National Institute of Biological Standards and Controls (NIBSC, Herdfordshire, UK). Total RNA was extracted from either a virus seed stock or from allantoic fluid of eggs infected with these viruses using QIAamp® Viral RNA Mini Kit (QIAGEN GmbH, Hilden, Germany). The influenza virus RNA was then used as template for reverse transcription as follows:

1 µl of RNA was annealed with 20 ng of oligonucleotides for priming (Table 1) in a total volume of 12 µl. First stranded DNAs were synthesized in a 20 µl volume using 200 units of Moloney Murine Leukemia Virus-derived reverse transcriptase without RNase H activity (Superscript II RNase Gibco-BRL Eggenstein, Germany) and the reaction condition recommended by the manufacturer. After 60 minutes at 42° C., the reaction mix was denatured for 30 minutes at 95° C. Complementary DNA sequences from the influenza virus strain A/HK/213/03 (H5N1) was kindly provided by Dr. Robert Newman at NIBSC.

DNA sequences encoding haemagglutinin (HA), neuraminidase (NA) and nucleoprotein (NP) were separately amplified by PCR from 1 µl cDNA with 60 units of thermostable Pwo DNA polymerase (Roche Applied Science, Rotkreuz, Switzerland) in 50-µl reaction mixtures. Each 5' and 3' PCR primer contains artificial restriction endonuclease sites for cloning purposes. In addition, the 5' primers contain a canonical Kozak sequence (GCCGC-CACC, SEQ ID NO:1) just before the initiation codon of the gene for efficient translation of the gene of interest in eukaryotic cells. After 30 cycles of PCR (denaturation step at 95° C. for 45 seconds, annealing step at 60° C. for 45 seconds, and extension step at 72° C. for 90 seconds), the product was further incubated at 72° C. for 7 minutes. Subsequently 4 µl of 100 mM $MgCl_2$ and 2 µl of Klenow fragment of E. coli DNA polymerase (5 units/g were added to the reaction and incubated at 37° C. for 15 minutes.

The DNA was purified with QIAquick PCR Purification Kit (QIAGEN) to remove salts and unincorporated mono- and oligonucleotides. Amplified fragments except the haemagglutinin gene of the pandemic viral strain (H5) were cloned as follows. After restriction digestion with Sal I and Not I, DNA fragments of expected sizes (1.7, 1.4 and 1.5 kb for haemagglutinin, neuraminidase and nucleoprotein, respectively) were isolated by preparative agarose gel electrophoresis. Recovered DNA fragments were ligated to pBluescript KS vector (digested with Sal I and Not I) using T4 DNA ligase and transformed into XL-10 E. coli competent cells (Stratagene, La Jolla, Calif.). The H5 cDNA fragment was digested with Asc I and Not I followed by preparative agarose gel electrophoresis. The purified H5 fragment was ligated using T4 DNA ligase to pBluescript KS vector of which Sal I site had been converted to an Asc I site and transformed to XL-10 E. coli competent cells. Several cDNA clones were isolated from single E. coli colonies to verify that no artificial mutations had been introduced in the amplified DNA fragments.

The individual influenza genes were then subcloned into an alphavirus replicon vector as follows (FIG. 2). The haemagglutinin and neuraminidase gene fragments (Sal I-Not I) of Resvir-17 (H3 and N2) were excised from pBluescript and subcloned into the Xho I-Not I sites of the Sindbis virus replicon backbone SINCR (Gardner et al., 2000, J. Virol. 74:11849-11857. In order to subclone the H3 fragments into the VEE/SIN replicon vector backbone, pVCRchim2.1 (Perri et al., 2003, J. Virol. 77:10394-10403), the pBluescript clone was first digested with Sal I, blunt-ended with Klenow fragment, excised by Not I restriction. The isolated H3 fragment was transferred to pVCRchim2.1 of which Asc I site had been blunt-ended. For subcloning of the haemagglutinin (H1), neuraminidase (N1) and nucleoprotein (WNP) genes of WS/33 into the pVCRchim2.1 vector, the Sal I recognition sequence at one of the insertion sites was converted to an Asc I by Sal I restriction, filling the cohesive end with dNTP and Klenow fragment and ligation with Asc I linker.

After extensive digestion with Asc I, DNA fragments were isolated by preparative agarose gel electrophoresis. Recovered DNA fragments were self-ligated using T4 DNA ligase and introduced to XL-10 E. coli cells. Plasmid DNA from transformed E. coli clones was submitted to Asc I/Not I double restriction. The H5 fragment was purified directly by Asc I/Not I double digestion. The insert fragments were separated from the vector DNA by preparative agarose gel electrophoresis. The purified DNA fragments were ligated to the pVCRchim2.1 vector (digested with Asc I and Not I) using T4 DNA ligase. All pVCRchim2.1 vectors ligated with inserts were transformed to XL-1 blue E. coli electrocompetent cells (Stratagene, La Jolla, Calif.).

Other influenza virus genes may be generated in a similar manner by one of skill in the art, using the teachings provided herein. Additionally, it should be appreciated that analogous alphavirus vector constructs derived from other alphaviruses may be readily substituted without undue experimentation.

Table 1 shows the sequences of various primers used for PCR and reverse transcription.

TABLE 1

| Target Gene | Primer Name | Sequence | Sequence Added |
|---|---|---|---|
| H3 | HA3F 1 (cDNA and PCR 5' primer) | 5'-GGGTCGACTG CAGCCGCCAC CATGAAGACT ATCATTGCT (SEQ ID NO: 2) | Sal I, Pst I, Kozak |
| H3 | HA3R1 (PCR 3' primer) | 5'-GCATGCGGCC GCATCGATTC AAATGCAAAT GTTGCACCT (SEQ ID NO: 3) | Not I, Cla I |
| N2 | NA2F1 (cDNA and PCR 5' primer) | 5'-GGGTCGACAG ATCTGCCGCC ACCATGAATC CAAATCAA (SEQ ID NO: 4) | Sal I, Bgl II, Kozak |
| N2 | NA2R1 (PCR 3' primer) | 5'-GCATGCGGCC GCATCGATTA TATAGGCATG AGATTGATG (SEQ ID NO: 5) | Not I, Cla I |
| H1 | HA1F1 (cDNA and PCR 5' primer) | 5'-GGGTCGACTG CAGCCGCCAC CATGAAGGCA AAACTACT (SEQ ID NO: 6) | Sal I, Pst I, Kozak |
| H1 | HA1R1 (PCR 3' primer) | 5'-GCATGCGGCC GCATCGATTC AGATGCATAT TCTRCA (SEQ ID NO: 7) | Not I, Cla I |
| N1 | NA1F1 (cDNA and PCR 5' primer) | 5'-GGGTCGACAG ATCTGCCGCC ACCATGAATC CAAACCARA (SEQ ID NO: 8) | Sal I, Bgl II, Kozak |
| N1 | NA1R1 (PCR 3' primer) | 5'-GCATGCGGCC GCATCGATCT ACTTGTCAAT GSTGA (SEQ ID NO: 9) | Not I, Cla I |
| WNP (NP of WS/33) | NPF1 (cDNA and PCR 5' primer) | 5'-GGGTCGACTC TAGAGCCGCC ACCATGGCGT CYCAAGGCAC CA (SEQ ID NO: 10) | Sal I, Xba I, Kozak |
| WNP (NP of WS/33) | NPR1 (PCR 3' primer) | 5'-GCATGCGGCC GCATCGATTA ATTGTCGTAY TCYTC (SEQ ID NO: 11) | Not I, Cla I |
| H5 | HA5F1 (cDNA and PCR 5' primer) | 5'-GCATGGCGCG CCGTCGACGC CACCATGGAR ARAAYAGTGC TTCT (SEQ ID NO: 12) | Asc I, Sal I, Kozak |
| H5 | HA5R1 (PCR 3' primer) | 5'-GCATGCGGCC GCATCGATTA AATGCARATT CTGC (SEQ ID NO: 13) | Not I, Cla I |
| IRES | EMIRF2 (PCR 5' primer) | 5'-TTTGGCGCGC CATCGATGAT ATCTGATTTT CCACCATATT G (SEQ ID NO: 14) | Asc I, Cla I |
| IRES | EMIRR2 (PCR 3' primer) | 5'-GCATGCGGCC GCGTCGACTT ATCATCGTGT TTTTCAAAGG (SEQ ID NO: 15) | Not I, Sal I |

R = A or G,
S = C or G,
Y = C or T

Example 2

Construction of Alphavirus Replicon Vectors Containing at Least Two Genes Encoding Influenza Virus Antigens Additional replicon vector constructs were generated that contain at least two separate antigen-encoding genes within the same replicon vector, for example, as a bicistronic construct (FIG. 2). Specifically, in one representative example, the internal ribosomal entry site (IRES) sequence of encephalomyocarditis virus (EMCV) (Dule, et al., 1992, J. Virol. 86:6126) was used to co-express both a hemagglutinin and neuraminidase antigen.

The IRES was subcloned into pBluescript adding artificial cloning sites by PCR using a plasmid containing IRES (pIRES) and primers indicated in Table 1. The Asc I-Cla I fragment encoding HA1 and Sal I-Not I fragment encoding NA1 were subcloned into the newly constructed IRES plasmid using the same restriction sites. Asc I/Not I double restriction yielded a 3.6 kb fragment, which contains H1, IRES and N1 sequences in that order. This fragment was purified with preparative agarose gel and subcloned to the pVCRchim2.1 vector (digested with Asc I and Not I) in the same manner as the other monocistronic constructs.

In addition, a second (e.g., duplicated) alphavirus subgenomic junction region promoter was used to express the second influenza virus gene, as follows and as described below for PIV genes. More specifically, the above vector construct expressing FLU NA alone was used as template for the PCR amplification of a fragment comprising the alphavirus subgenomic promoter and NA gene. Oligonucleotides IN-F and IN-R listed below, were used as PCR primers under standard conditions.

```
IN-F
                                    (SEQ ID NO: 16)
5'-ATATATATATGCGGCCGCTGGAGGGTTTATTTTGTGTGAC

IN-R
                                    (SEQ ID NO: 17)
5'-ATATATATATGTAGCGGCGGCCGCATCGATTC
```

The PCR products were purified, digested with NotI and ligated into the alphavirus vector expressing HA alone, which was also digested with NotI, to generate the bicistronic HA+NA construct with duplicated subgenomic promoters providing expression of the two FLU genes.

In addition to replicon vectors that express both the FLU HA and NA genes, other combinations of FLU genes may be substituted in the present invention, such as for example HA+NP, NA+NP, HA+M, NA+M, and the like. The FLU genes may be obtained from any FLU virus source, including for example from predominantly avian strains (e.g., H5, H7, H9) described above. It should also be appreciated that analogous multi-cistronic (e.g., bicistronic) alphavirus vector constructs derived from other alphaviruses may be readily constructed in a similar manner by one of skill in the art without undue experimentation.

Example 3

Production of Alphavirus Replicon Particles Expressing One or more Influenza Virus Antigens Alphavirus replicon particles containing the above described replicon constructs are prepared using any number of available methods described above and used in the field (e.g., RNA co-transfection with in vitro transcribed defective helper RNA(s), introduction into packaging cell lines).

In particular, influenza virus gene containing replicon vectors described above were transcribed in vitro and used to produce replicon particles as described in Perri et al. (2003) J. Virol. 77:10394-10403). Replicon particles were harvested as cell culture supernatants, clarified by filtration, subjected to ion exchange chromatography (WO0192552), subjected to an additional filtration step, and the purified replicon particle material formulated in a pharmaceutically acceptable diluent. Determination of replicon particle titer and absence of contaminating replicon-competent virus was performed using standard techniques in the field, essentially as described in U.S. Pat. Nos. 6,015,694, 5,789,245, 5,843,723, 6,451,592; Perri et al. (2003) J. Virol. 77:10394-10403); Polo et al., ibid; WO0192552).

Antigen expression following infection of culture cells was confirmed by immunostaining using an appropriate antigen-specific antibody. Referring now to FIG. 11, there are shown the results of Fluorescent Activated Cell sorting studies carried out to determine antigen expression following infection of cells with alphavirus particles expressing one or more influenza antigens.

FIG. 11 demonstrates the expression of both FLU HA and NA antigens from the two different bicistronic alphavirus replicon configurations described above (one with internal ribosome entry site, IRES, the other with a duplicated alphavirus subgenomic promoter, sgp), following infection of cultured cells. Other combinations of FLU antigens may be similarly expressed in a bicistronic configuration for use as an immunogenic or vaccine composition, based on the teachings provided herein. The present invention also contemplates the combination of two or more different replicon particles (e.g., expressing different FLU antigens) in an immunogenic or vaccine composition and methods for stimulating an immune response using such combinations. Non-limiting examples of such combinations include for example particles encoding FLU HA+particles encoding FLU NA, particles encoding FLU HA+particles encoding FLU NP, particles encoding FLU NA+particles encoding FLU NP, particles encoding FLU NA+particles encoding FLU M, particles encoding both FLU HA+NA from a first strain+particles encoding FLU HA from a second strain, and the like.

Example 4

Generation of Alphavirus Replicon Vectors Containing Human Parainfluenza Virus HN or F Antigen-encoding Genes To generate alphavirus replicon particles expressing the fusion protein (F) from human parainfluenza virus type 3 (hPIV3), the F open reading frame (nt. 4690 to nt. 5589 of genome sequence, GenBank accession Z11575, and Stokes, et al., 1992 Virus Res. 25 (1-2), 91-103) was synthesized as a duplex DNA molecule by standard commercial gene synthesis techniques, the sequence was verified, and the synthesized gene cloned into the pUC18 vector by GenScript Corporation.

During the synthesis, an Asc I restriction site and Kozak consensus sequence were added just upstream the ATG initiation codon, and a Not I site was added just downstream the stop codon. The plasmid containing the F gene was then digested with AscI and NotI and the F gene subcloned into the VCR-Chim2.1 replicon backbone, generating VCR-Chim2.1-$F_{PIV3}$ (FIG. 3).

Truncated versions of envelope glycoproteins of the present invention also are generated wherein all or part of the transmembrane anchor region (and optionally cytoplasmic tail) is deleted so as to result in a secreted form of the protein. For example, the PIV F gene is modified such that the membrane anchor region (amino acid residues 494-516) is removed. More specifically, a segment of the F gene in VCR-Chim2.1-$F_{PIV3}$, between the convenient restriction sites XbaI and NotI (region coding for the last 73 amino acid residues) is replaced with a DNA fragment generated by overlapping oligonucleotides that regenerate this fragment with a deletion of 22 amino acid residues corresponding to the transmembrane anchor and a silent mutation adding a convenient restriction site (ScaI) for clone screening. The following oligonucleotides are used:

```
TM-F1 (SEQ ID NO: 18):
ctagaagaatcaaaagaatggataagaaggtcaaatcaaaaactagatt ctattggaaattggcatcaatctagcacta TM-R1 (SEQ ID NO: 19):
tagtacttaattgtagtgctagattgatgccaatttccaatagaatcta gttttttgatttgaccttcttatccattcttttgattctt TM-F2 (SEQ ID NO: 20):
ctagaagaatcaaaagaatggataagaaggtcaaatcaaaaactagatt ctattggaaattggcatcaatctagcacta TM-R2 (SEQ ID NO: 21):
Ggccgcttatttgtttgttagtacatatggcttgtcattttgatccact cgatttctcttttgaattctg
```

Oligonucleotides are re-constituted as per the supplier's recommendation to yield 100 nM solutions of each individual oligo. To assemble the fragment, 100 pmoles of each oligo is mixed in a single reaction tube containing T4 polynucleotide kinase buffer (New England Biolabs, Beverly, Mass.), 1 mM rATP, water, and 10 units of T4 polynucleotide kinase enzyme (New England Biolabs, Beverly, Mass.) in a final reaction volume of 500 ul. The phosphorylation reaction is allowed to proceed for 30 minutes at 37° C., at which time the reaction is supplemented with an additional 10 units of T4 polynucleotide kinase and allowed to continue for an additional 30 minutes.

At the conclusion of the reaction, the tube containing the mixture is heated to 95° C. for 5' in a beaker containing a large volume of water to denature the enzyme and any DNA strands that may have already annealed. The beaker is then removed from the heat source and allowed to slowly cool to ambient temperature, in order for the complementary oligonucleotides to anneal into full duplex DNA strands.

Once cooled, 0.2 pmoles of the reacted material is ligated with 100 pmoles of VCR-Chim2.1-$F_{PIV3}$ DNA previously digested with XbaI and NotI, alkaline phosphatase treated, and gel purified (the 12 kb band). The ligation is transformed into competent bacteria according to standard methods and transformants are analyzed for the presence of the appropriate terminal enzyme sites, for insert size, evidence of insert duplication, and orientation. Several positive transformants are then randomly chosen and sequences confirmed. Any sequence errors can be corrected by standard site-directed mutagenesis. A construct deleted of both the transmembrane domain and cytoplasmic tail also is generated by using standard PCR methods, the oligonucleotides below as primers, and VCR-Chim2.1-$F_{PIV3}$ as template.

```
PIVf:
                                      (SEQ ID NO: 22)
5'-ATATATATATATACGGCGCGCCACCATGCCAAC

PIVr:
                                      (SEQ ID NO: 23)
5'-ATATATATATGCGGCCGCTTATGTAGTGCTAGATTGATGCCAATTTC
```

The truncated F gene PCR product is then substituted into VCR-Chim2.1-$F_{PIV3}$ in place of the full-length PIV F gene using standard techniques.

Similarly to F, in order to generate alphavirus replicon particles expressing the hPIV3 HN antigen, the HN open reading frame (nt. 6806 to nt. 8524 of the genome sequence) also was synthesized using standard commercial techniques known in the art and cloned into pUC18 by GenScript Corporation. In this case, the Asc I and Not I restriction sites and Kozak consensus sequences also were added. This plasmid was then digested with Asc I and Not I, and cloned into VCR-Chim2.1 to generate VCR-Chim2.1-$HN_{PIV3}$ (FIG. 3). Expression of HN was confirmed by transfection of BHK cells with in vitro transcribed RNA synthesized from VCR-Chim2.1-$HN_{PIV3}$ template using standard procedures, followed by western blot analysis using PIV specific polyclonal antisera raised against inactivated PIV3 virus.

It should also be appreciated that other PIV genes also may be used and that analogous single or bicistronic alphavirus vector constructs derived from other alphaviruses may be readily constructed in a similar manner by one of skill in the art without undue experimentation. Also, PIV genes may be generated for cloning into the alphavirus vector backbones using standard RT-PCR techniques, such as those described below for RSV genes.

Example 5

Generation of Alphavirus Replicon Vectors Co-expressing Both Human Parainfluenza Virus HN and F Antigens Alphavirus replicon vectors co-expressing the hPIV3 HN and F antigens may be constructed in multiple ways (FIG. 3), for example as an IRES-bicistronic construct (described above) or as a double-subgenomic promoter construct (also described above).

Specifically, the HN antigen is expressed from a first alphavirus subgenomic promoter and the F antigen is expressed from a second alphavirus subgenomic promoter. Such as construct is readily made by cloning the F gene as a cassette already containing the F open reading frame and the alphavirus subgenomic promoter from construct VCR-Chim2.1-$F_{PIV3}$ or VCR-Chim2.1-$FdlSP_{PIV3}$ (described above).

These constructs are digested with the single restriction enzymes Msc I (located at −82 from transcription start) or Swa I (located at −566 from transcription start), ligated to a Not I linker, digested with Not I, gel purified, and ligated to VCR-Chim2.1-$HN_{PIV3}$ previously treated with NotI and alkaline phosphatase. Transformants are then screened for the presence of the insert and the correct orientation with appropriate restriction digests, such as Asc I, which releases a 1.7 kb (for the Msc I-Not I cassette) or a 2.2 kb (for the Swa I-Not I cassette). Alternatively, standard PCR methodologies, such as those describe above, may be used to accomplish the same construction.

Example 6

Production of Alphavirus Replicon Particles Expressing One or more Parainfluenza Virus Antigens Alphavirus replicon particles containing replicon constructs described above may be prepared using any number of available methods described above and used in the field (e.g., replicon RNA co-transfection with one or more in vitro transcribed defective helper RNAs, replicon introduction into packaging cell lines). For example, the parainfluenza virus HN gene-containing replicon vector described in Examples 4 and 5, was transcribed in vitro and used to produce replicon particles as described in Perri et al. (2003) *J. Virol.* 77:10394-10403).

Replicon particles were harvested from cell culture supernatants, clarified by filtration, subjected to ion exchange chromatography (WO0192552), subject to an additional filtration step, and the purified replicon particle material was formulated in a pharmaceutically acceptable diluent. Determination of replicon particle titer and absence of contaminating replicon-competent virus was performed using standard techniques in the field (see for example, U.S. Pat. Nos. 6,015,694, 5,789,245, 5,843,723, 6,451,592; Perri et al. (2003) *J. Virol.* 77:10394-10403); Polo et al., ibid; WO0192552). Expression of the PIV antigen was confirmed by immunostaining and western blot with an appropriate antibody following infection of cultured cells Example 7

Generation of Alphavirus Replicon Vectors Containing Respiratory Syncytial Virus G or F Antigen-encoding Genes To construct alphavirus replicon vectors expressing the RSV fusion glycoprotein (F), the F open reading frame was generated from the human A2 strain (nt. 5661-7382 of genome sequence, GenBank accession #M74568; Wertz, et al. 1985 Proc. Natl. Acad. Sci, USA 82, 4075-4079), as a duplex DNA molecule by standard commercial gene synthesis techniques, the sequence was verified, and the synthesized gene cloned into the pUC18 vector by Retrogen Corporation.

During the synthesis, an Asc I restriction site and Kozak consensus sequence were added just upstream the ATG initiation codon, and a Not I site was added just downstream the stop codon. The plasmid containing the F gene was then digested with AscI and NotI and the F gene subcloned into the VCR-Chim2.1 replicon backbone, generating VCR-Chim2.1-$F_{RSV}$ (FIG. 4).

Alphavirus replicon vectors expressing the G attachment protein from respiratory syncytial virus (RSV) are generated as follows. A cDNA sequence encoding for the G protein is generated from a human isolate, such as for example, the A2 strain (GenBank accession #M74568; Wertz, et al. 1985 Proc. Natl. Acad. Sci. USA 82, 4075-4079). The cDNA of the 900 nucleotide gene (from nt. 4690 to nt. 5589 of the genome sequence) is generated by reverse transcription of polyA mRNA extracted from cells infected with the RSV (extracted with Triazol, BRL, followed by Oligotex, Qiagen) using Superscript Pre-amplification kit (GIBCO-BRL) and a poly-dT oligonucleotide. Then the cDNA is amplified by the standard three step PCR amplification (30 cycles of 30 sec at 94° C., 30 sec at 60° C., 1 min at 72° C.), using Vent Polymerase (NEB) or Pfu (Stratagene) and the following oligonucleotides:

```
RSV-Gf:
                                     (SEQ ID NO: 24)
atatatatggcgcgccccaccatgtccaaaaacaaggaccaac RSV-Gr:
                                     (SEQ ID NO: 25)
atatatatgcggccgcctactggcgtggtgtgttggg
```

The RSV-Gf oligonucleotide contains the convenient restriction site AscI followed by the Kozak consensus sequence placed upstream the starting ATG. The RSV-Gr oligonucleotide contains the restriction site Not I. Following amplification, the DNA fragment is purified with QIAquick-spin (Qiagen), digested with AscI and Not I and gel purified. The fragment is then ligated to the VCR Chim2.1 replicon vector DNA that has been previously digested with AscI and Not I, treated with shrimp alkaline phosphatase, and purified from a 0.7% agarose gel, to generate a construct VCR-Chim2.1-$G_{RSV}$ (FIG. 4). Similarly, cDNA encoding for the F protein (nt. 5661-7382 of genome sequence) is generated from a human or animal (veterinary) isolate, such as for example, the A2 strain, as described in the previous example. The cDNA is amplified by the standard three step PCR amplification (30 cycles of 30 sec at 94° C., 30 sec at 60° C., 1 min at 72° C.), using Vent Polymerase (NEB) or Pfu (Stratagene) and the following oligonucleotides:

```
RSV-Ff:
                                     (SEQ ID NO: 26)
atatatatggcgcgccccaccatggagttgctaatcctcaaagc RSV-Fr:
                                     (SEQ ID NO: 27)
atatatatgcggccgcttagttactaaatgcaatattatttatac
```

The RSV-Ff oligonucleotide contains the convenient restriction site AscI followed by the Kozak consensus sequence placed just upstream the starting ATG, and the RSV-Gr oligonucleotide contains the restriction site NotI. The amplified fragment is then treated and cloned into VCR-Chim2.1 as described in the previous example, generating the construct VCR-Chim2.1-$F_{RSV}$ (FIG. 4). Alternatively, the RSV G gene may be synthesized commercially, as described above for PIV genes.

Truncated versions of envelope glycoproteins from respiratory virus pathogens of the present invention (e.g., RSV F) also may be generated by one of skill in the art using standard molecular biology techniques wherein all or part of the transmembrane anchor region (and optionally cytoplasmic tail) is deleted so as to result in a secreted form of the glycoprotein. Other modifications to the envelope glycoprotein genes of the present invention also are contemplated and may be readily substituted, such as for example, deletion or substitution of 5'-end nontranslated regions, incorporation of heterologous leader sequences, and the like.

In a similar manner, the sequence for RSV M 2-1 is synthesized commercially with flanking AscI and NotI sites and cloned into the VCR-Chim2.1 backbone.

Transformants arising from this ligation are analyzed first for the presence of the appropriate cloning sites, for insert size, and evidence of insert duplication. Several positive transformants are randomly chosen and submitted for sequence confirmation.

Example 8

Construction of Alphavirus Replicon Vectors Co-expressing Both the Respiratory Syncytial Virus G and F Antigens Alphavirus replicon vectors co-expressing both the RSV G and F antigens, or either F or G plus an additional antigen (e.g., M2-1), are constructed in multiple ways (FIG. 4), such as for example as an IRES-bicistronic construct (described above) or as a double-subgenomic promoter construct (also described above).

In one representative example, the G antigen is expressed from a first alphavirus subgenomic promoter and the F antigen is expressed from a second alphavirus subgenomic promoter, within the same replicon vector. This construct is readily made by cloning the F gene sequence as a cassette containing the F open reading frame and the alphavirus subgenomic promoter from construct VCR-Chim2.1-$F_{RSV}$ described above.

This construct is digested with the single restriction enzymes Msc I (located at −82 from transcription start) or Swa I (located at −566 from transcription start), ligated to NotI linker, digested with NotI, gel purified, and ligated to VCR-Chim2.1-$G_{hRSV}$ previously treated with NotI and alkaline phosphatase. Transformants are then screened for the presence of the insert and the correct orientation with appropriate restriction digests such as Asc I, which releases a 1 kb (for the Msc I-NotI cassette) or a 1.5 kb (for the Swa I-Not I cassette).

The present invention also contemplates that analogous single or bicistronic alphavirus vector constructs derived from other alphaviruses may be readily constructed in a similar manner by one of skill in the art using the teachings provided herein.

Example 9

Production of Alphavirus Replicon Particles Expressing One or more Respiratory Syncytial Virus Antigens Alphavirus replicon particles containing the above described replicon constructs may be prepared using any number of available methods described above and used in the field (e.g., RNA co-transfection with in vitro transcribed defective helper RNA, introduction into packaging cell lines), For example, respiratory syncytial virus G gene-containing replicon vector is transcribed in vitro and used to produce replicon particles as described in Perri et al. (2003) *J. Virol.* 77:10394-10403). Replicon particles are obtained by harvesting transfected cell culture supernatants, clarifying by filtration, subjecting to ion exchange chromatography (WO0192552), subjecting to an additional filtration step, and formulating the purified replicon particle material in a pharmaceutically acceptable diluent. Determination of replicon particle titer and absence of contaminating replicon-competent virus is performed using standard techniques in the field (U.S. Pat. Nos. 6,015,694, 5,789,245, 5,843,723, 6,451,592; Perri et al. (2003) *J. Virol.* 77:10394-10403); Polo et al., ibid; WO0192552), Confirmation of antigen expression is by immunostaining or other suitable techniques following infection of cultured cells with the replicon particles.

Example 10

Construction of Alphavirus Replicon Vectors Containing the Human Metapneumovirus G Antigen-Encoding Gene To construct alphavirus replicon vectors expressing the human metapneumovirus (HMPV) attachment protein (G), the cDNA sequence encoding for the G protein is generated from a human virus isolate, such as for example isolate 00-1 (Van Den Hoogen et al 2001, Nature Med. 7:719-724, GenBank Accession #AF371337), by RT-PCR on RNA extracted from infected cultures as described in previous examples. The forward oligonucleotide for the PCR amplification includes the Asc I site and Kozak consensus sequence, and the reverse oligo includes the Not I site as follows:

```
HMPV-Gf:
                                    (SEQ ID NO: 28)
atatatatggcgcgcccaccatggaggtgaaagtggagaac HMPV-Gr:
                                    (SEQ ID NO: 29)
atatatatgcggccgcttaactagtttggttgtatgttgttg
```

The amplified fragment is then treated and cloned into VCR-Chim2.1 as described in previous examples, generating the replicon VCR-Chim2.1-$G_{HMPV}$. Replicon particles containing this vector are produced as described above.

Example 11

Construction of Alphavirus Replicon Vectors Containing the SARS Coronavirus Spike Antigen-Encoding Gene The SARS virus spike gene can be incorporated into alphavirus replicon vectors in its entirety (encoding full-length spike protein) or in a modified form that includes, for example, sequence deletions or truncations, such that the encoded a spike protein is of less than full-length (e.g., deleted of transmembrane region and cytoplasmic tail). For example, the spike gene may be cloned as a full-length gene into the VCR-chim2.1 vector (WO 02/99035) by standard RT-PCR conditions. For the reverse transcription step in standard RT-PCR, the Superscript pre-amplification kit (Invitrogen) and the following primer is used:

```
Sp-RT-R
                                    (SEQ ID NO: 30)
Ctcataaacaaatccataagttcg
```

For the amplification step, the cDNA polymerase advantage kit (Clonetech) and the following primers are used:

```
Sp-F-BbvCI
                                    (SEQ ID NO: 31)
atatatatat cctcagc ccacc atgtttatttctctattatttctt
actc Sp-R-NotI
                                    (SEQ ID NO: 32)
Atatatatgcggccgcttatgtgtaatgtaatttgacaccc
```

The forward primer is designed to contain the ccacc sequence (Kozak, 1991 JBC 19867-70) in front of the ATG codon to optimize translation efficiency of the spike gene.

Also, the forward primer contains the BbvCI restriction site and the reverse primer contains the NotI restriction site for subsequent cloning of the PCR amplified gene. The PCR product is purified using the QIAquick Nucleotide Removal kit (QIAgen), digested with BbvCI and NotI, gel purified with QIAquick Gel Extraction kit (QIAgen), and ligated to plasmid VCR-Chim2.1 pre-digested with the same enzymes.

Clones containing the SARS spike sequence are verified by sequencing and the new construct is called VCR-Chim2.1-SARSspike.

To generate VEErep/SINenv-SARSspike replicon particles the plasmids VCR-Chim2.1-SARSspike, VCR-DH-Scap (WO 02/99035), and VCR-DH-Sglyd1160 (WO 02/99035) were linearized with the restriction enzyme PmeI and used for in vitro transcription as described previously (Polo et al. 1999, PNAS 96: 4598-603, WO 02/99035). The transcripts are co-transfected into BHK cells as previously described (Polo et al., 1999, ibid., WO 02/99035). The transfected cells are incubated at 34° C., the supernatants collected at 20 and 30 hrs post-electroporation, clarified by centrifugation, and purified by chromatography as previously described (PCT WO 01/92552).

Expression of the SARS spike protein from the replicon particle vector was verified by infecting BHK cells overnight with purified VEErep/SINenv-SARSspike or VEErep/SINenv-GFP (WO 02/99035) replicon particles. In addition, BHK cells also were transfected in parallel with in vitro transcribed VCR-Chim2.1-SARSspike replicon RNA. At 16 hrs post-infection and transfection, cells were lysed and a sample of the lysate analyzed by western blot using an antibody that recognizes SARS virus spike protein, confirming expression.

Example 12

Production of an Inactivated PIV Vaccine

PIV3 strain JS was used to infect LLC-MK2 cells and media supernatant collected at 96 hours post infection was clarified and filtered through a 0.2 um filter. Approximately 450 ml of the harvested media was applied to a 10 ml column containing the cationic exchange resin, Fractogel® EMD $SO_3^-$ (M) (s-Fractogel®, EM Industries). The column had been sanitized with 0.5 N NaOH followed by 10 column volumes of WFI and equilibrated with 10 mM sodium phosphate, 125 mM sodium chloride, pH 7.0.

The clarified supernatant was passed through the column at a flow rate of 115 cm/hour. The column was washed with approximately 40 column volumes of equilibration buffer. A single step elution was made by applying approximately 20 ml of buffer containing 10 mM sodium phosphate, 400 mM sodium chloride, pH 7.0. The eluted peak as based on absorbance at 280 nm was diluted to 125 mM sodium chloride and 40 mg/ml lactose.

Inactivation of the PIV3 was effected by the addition of β-propiolactone (catalogue #P 1424, Spectrum Chemical Mfg. Corp., Gardena, Calif.). Stock solution of β-propiolactone was first diluted to 1:200 into highly purified water, then slowly, dropwise, diluted to a concentration of 1:2000 directly into the virus stock. The solution was carefully mixed and allowed to incubate over night at 4° C. The inactivation of the β-propiolactone was achieved by incubation at 37° C. for 4 hours.

To assess the effectiveness of the inactivation, aliquots of the inactivated virus were serially diluted onto LLC-MK2 cells and incubated for 7 days. No detection of virus was seen in the inactivated sample as determined by cytopathic effect (CPE). Total protein concentration of β-propiolactone-inactivated virus was estimated to be 0.5 mg/ml by BCA (Pierce Chemical). Immunogenicity of the inactivated virus was confirmed in both mice and hamsters using intramuscular and intranasal immunizations. A single dose for an intra-nasal immunization comprised of 5 µg β-propiolactone-inactivated virus and 10 µg LTK63 adjuvant in a total volume of 0.03 ml for mice and 0.1 ml for hamsters. A dose for intramuscular immunization comprised 5 µg β-propiolactone-inactivated virus diluted in 0.05 ml lactose buffer then gently mixed by inversion with and equal volume of MF59 adjuvant just prior to immunization. Total volume of intramuscular immunizations for both mice and hamsters was 0.1 ml.

Example 13

Stimulation of an Influenza Virus Specific Immune Response Using an Alphavirus Replicon Particle Vaccine To demonstrate stimulation of a FLU antigen-specific immune response, SIN replicon particles expressing HA antigen were used to immunize BALB/c mice in parallel with commercial subunit FLU vaccine antigen. Replicon particles and protein were administered intramuscularly twice and HA-specific serum antibody responses were determined by standard ELISA assay following each immunization.

Nunc Maxisorp® flat-bottom plates were coated overnight at 4° C. with a PBS solution containing 2.5 µg/m monovalent subunit influenza vaccine preparation (Chiron S.r.l., Italy). Plates were then washed three times with PBS (pH7.2) supplemented with 0.05% Tween-20 (PBS-T). After washing wells were blocked against non-specific binding using 5% (w/v) dry milk in PBS-T for 1 hour at 37° C. Sample sera were serially diluted in PBS-T by three fold starting from 1:50. After incubation with diluted sera at for 90 minutes at 37° C., plates were rinsed three times with PBS-T.

Plates were further incubated with alkaline phosphatase conjugated goat anti-mouse Ig, IgG1, or IgG2a (Southern Biotechnology Associates Inc., AL) diluted in PBS-T for 1 hour at 37° C. After extensive washing with PBS-T, 100 µl of a chromogen-substrate solution, paranitrophenylphosphate 1 mg/ml in diethanolamine, were added to each well. Then, the plate was read after 20 min at 405 nm using SpectraMax® (Molecular Devices, CA). For calculation of titers, a cut-off value was defined as the optical density (OD) value of average of PBS controls plus 3× their standard deviation. Antibody titers were then calculated as dilutions of which the samples generate OD of the cut-off value. As shown in FIG. 6, the SIN replicon particles were highly potent at both doses tested and of greater immunogenicity than the commercial protein based vaccine.

Similar results were observed in another experiment performed in three different mouse strains. More importantly, in addition to enhanced ELISA (binding) antibody titers, the SIN replicon particles produced enhanced levels of neutralizing antibodies as determined by hemagglutination inhibition assay (FIG. 7). Sera from immunized mice were treated with neuraminidase by adding 4 volumes of Test Neuraminidase (Dade Behring, Liederbach, Germany) diluted 1:50 or 1:100 in PBS (pH7.0) and incubated at 37° C. over night. To inactivate neuraminidase, 3 serum volumes of 2.5% sodium citrate solution is added and incubated at 56° C. for 30 minutes in a water bath. Two serum volumes of PBS were further added to adjust dilution to 1:10 before the assay. Twenty-five μl of serially two-fold diluted sera were dispensed into a v-bottom 96-well plate. The same volume of virus solution (RESVIR-17) that contains 4 haemagglutination units was added to diluted sera.

After 60 minutes of incubation at room temperature, 50 μl of chicken erythrocyte suspension (0.5%) were added and further incubated for 60 min at room temperature. The highest dilution of the serum that inhibits haemagglutination was determined visually. The assay was performed in duplicates and the average dilution was taken as the HI titer.

The SIN-derived replicon particles expressing HA were compared with VEE/SIN chimera replicon particles expressing HA to determine relative immunogenicity (FIG. 8). Mice were immunized twice with dosages of $10^6$, $10^5$ or $10^4$ replicon particles. Serum samples obtained post first and second immunization were analyzed by ELISA as described above. While the SIN replicon particles were more immunogenic than commercial subunit vaccine antigen, the VEE/SIN replicon particles provided an even greater level of immunogenicity. The VEE/SIN particles expressing FLU HA also were evaluated for immunogenicity in rhesus macaques and shown to induce significant levels of FLU neutralizing antibody based on HI titer (FIG. 10).

Example 14

Protection from Influenza Virus Challenge in Animals Immunized with Alphavirus Replicon Particles Expressing Influenza Virus Antigen Female Balb/c mice at age of 6 weeks were purchased from Charles River Laboratories. Influenza virus WS/33 used for challenge was titrated in vivo to determine doses lethal to naïve mice. For immunization, each group of mice (10 mice/group) received a dosage of $10^6$ of either FLU HA or NA expressing replicon particles or a FLU subunit vaccine preparation (monovalent, reassortant of A/New Caledonia/20/99 (H1N1)) containing 3 μg of haemagglutinin, in a volume of 50 μl of PBS, administered in the tibia anterior muscle. Mice were immunized twice with an interval of 3 weeks. Two weeks after the second immunization, mice were challenged with live WS/33 influenza virus. Twenty μl (10 μl for each nostril) of the allantoic fluid described above diluted by 1000 fold in PBS (approximately 100 $LD_{50}$) were administered intranasally without anesthesia to infect the virus in the upper respiratory tract.

Animals were monitored for mortality for 2 weeks from the day of challenge. As shown in FIG. 9, either of the alphavirus replicon particle-based vaccines expressing FLU NA or HA provided complete protection against intranasal FLU virus challenge. Also, HA or NA expressing compositions showed a high degree of protection from intranasal FLU challenge, even at very low immunization dosages, such as for example $10^4$ replicon particles or less (FIG. 21).

In addition to the replicon particle based FLU vaccines expressing a single FLU antigen, replicon particle preparations expressing more than one FLU antigen (HA+NA, see above) also showed a high degree of protection in the intranasal challenge model (FIG. 22).

It should be noted that the present invention contemplates that immunogenic responses to any of the above alphavirus replicon particle based FLU vaccines may be further enhanced by "boosting" alphavirus replicon immunized warm-blooded mammals with a protein-based vaccine formulation (e.g., commercial subunit or split vaccine). This may be a particularly attractive approach for FLU pandemics arising from human infection with avian FLU viruses (e.g., H5, H7, H9 containing), where previous exposures to typical interpandemic FLU infection or vaccination (e.g., H3, H1 containing) and existing antibody levels arising from these may be of little benefit.

Example 15

Stimulation of a Parainfluenza Virus Specific Immune Response Using an Alphavirus Replicon Particle Vaccine Expressing the HN Antigen As described previously in this document, alphavirus replicon particles may be used to stimulate an immune response to a variety of respiratory pathogens (e.g., viruses, bacteria, fungi) following administration to a warm-blooded mammal.

SIN or VEE/SIN chimera replicon particles expressing the PIV HN antigen, as described in Example 4, were evaluated in BALB/c mice. Mice were immunized two times by the IM route, IN route or IN followed by IM route, and serum antibody was measured by ELISA assay after the second immunization (FIG. 12). Additional groups in this immunogenicity study also were immunized with the inactivated PIV vaccine by various routes. For ELISA, parainfluenza virus type three, grade 2 antigen (American Research Product, Inc. Catalogue #123065) was coated on Immulon Ib ELISA plates overnight (4° C.) at a concentration of 25 ng/well. Nonspecific binding was eliminated by blocking with 0.5% casein, 5% goat serum in PBS for 1 hour at 37° C.

Test sera were serially diluted in 0.5% casein and incubated for 1 hour at 37° C. after which the plates were washed with PBS and then incubated with either HRP-conjugated Goat anti-mouse IgG1 or IgG2a (CalTag) for 1 hour at 37° C. Immunocomplexes were detected by TMB and read of 450 nm.

Results demonstrate immunogenicity of the replicon particle by either route or a combination of routes (IN (intranasal) followed by IM (intramuscular)), and also immunogenicity of the inactivated PIV vaccine following IM or IN/IM administration. Dosages of VEE/SIN replicon particles expressing PIV HN were subsequently tested across the range of $10^7$, $10^6$ and $10^5$ particles (FIG. 13). Each dose was shown to be highly immunogenic.

The inactivated PIV vaccine was further characterized in the presence or absence of adjuvant (as described in Example 12), by a variety of routes. As shown in FIG. 14, the addition of adjuvant (MF59) enhanced immunogenicity of the inactivated PIV vaccine delivered IM. Inactivated PIV administered IN with LTK63 adjuvant followed by LM with MF59 adjuvant also induced strong antibody responses.

Example 16

PIV Vaccine Efficacy: Protection of Animals from Intranasal Challenge

In addition to mouse immunogenicity studies, the PIV vaccines of the present invention were evaluated for vaccine efficacy. Protection may be determined following virus challenge as documented in the literature (see for example, Ottolini et al., 2002, J. Infect. Dis. 186:1713-1717; Tao et al., 1999, Vaccine 17:1100-1108; Brideau et al., 1993, J. Gen. Virol. 74:471-477; Durbin et al., 2000, Vaccine 18:2462-2469; Pennathur et al., 2003, J. Gen. Virol. 84:3253-3261). For the hamster challenge model, human PIV3 virus undergoes a productive infection following intranasal challenge and replicates in the lungs and nasal turbinates of the hamsters. An effective vaccine will provide protection from intranasal challenge as evidenced by a significant reduction in the ability of the PIV challenge virus to replicate in these tissues in vaccinated animals.

Groups of 8 hamsters were immunized two times IM with BPL-inactivated PIV at a 5 ug dose in MF59, or with $10^7$ VEE/SIN replicon particles expressing PIV HN two times IM or one time IN followed by one time IM. The control group received only diluent, with no vaccine antigen. The vaccinations were performed three weeks apart and serum was tested for the induction of PIV specific antibody two weeks after each immunization. As shown in FIGS. 15 and 16 both the replicon particle and adjuvanted inactivated PIV vaccines induced high levels of PIV antibody. Three weeks following the second immunization, all animals were challenged intranasally with PIV virus. The animals were sacrificed four days after challenge and PIV challenge virus titers were determined in the lungs and nasal turbinates.

As shown in FIG. 17, the replicon particle and inactivated PIV vaccines provided complete protection of both the upper and lower respiratory tract from virus challenge. Protection of both the upper and lower respiratory tissues from PIV3 infection (not simply of one tissue, such as lungs only) is an important determinant and indicator of efficacy in these models.

To extend these hamster efficacy studies, the alphavirus replicon particle based PIV vaccines, parenteral IM routes and mucosal IN routes were compared. Groups of 6 hamsters were immunized twice at a 3-week interval with VEE/SIN-HN replicon particles ($10^7$ IU), by IM injection or by IN drop-wise administration. As shown in FIG. 23, both IN and IM routes generated PIV3 specific antibody responses two weeks post-immunization revealed, Subsequent challenge of the IM- or IN-immunized groups demonstrated complete protection from virus replication in both the upper (nasal) and lower (lung) respiratory tract tissues following intranasal PIV3 challenge, as was observed previously for IM immunization with replicon particles (FIG. 23).

Thus, alphavirus replicon particle can be used to generate immune responses against respiratory pathogens (e.g., viruses) by either parenteral or mucosal administration.

Example 17

Stimulation of a Parainfluenza Virus Specific Immune Response Using an Alphavirus Replicon Particle Vaccine Co-expressing HN and F Antigens As described previously in this document, replicon particles co-expressing multiple antigens may be used to stimulate an immune response to a parainfluenza virus following administration to a warm-blooded mammal.

Replicon particles co-expressing both the PIV HN and F antigens, as described in Examples 5 and 6, are evaluated for immunogenicity and efficacy in multiple animal models such as those described above prior to clinical evaluation in humans.

The formulations are administered by any of a variety of routes, such as for example IM, IN, SC, ID, IN followed by IM, and the like. Replicon particles are delivered at a dose of at least $10^4$, $10^5$, $10^6$, $10^7$ or $10^8$ infectious units (IU) one or more times. Immunogenicity is determined by standard measurements of binding antibody (ELISA) and/or neutralizing antibody (HI assay), and protection may be determined following virus challenge as documented in the literature (see for example, Ottolini et al., 2002, J. Infect. Dis. 186: 1713-1717; Tao et al., 1999, Vaccine 17:1100-1108; Brideau et al., 1993, J. Gen. Virol. 74:471-477; Durbin et al., 2000, Vaccine 18:2462-2469; Pennathur et al., 2003, J. Gen. Virol. 84:3253-3261).

Example 18

Stimulation of a Respiratory Syncytial Virus Specific Immune Response Using an Alphavirus Replicon Particle Vaccine Co-expressing G and F Antigens Replicon particles are used to stimulate an immune response to a respiratory syncytial virus (RSV) following administration to a warm-blooded mammal. For example, replicon particles co-expressing both the RSV G and F antigens, as described in Examples 8 and 9, are evaluated in multiple animal models (e.g., mice, cotton rats, monkeys) prior to clinical evaluation in humans. The formulations are administered by any of a variety of routes, such as for example IM, IN, SC, ED, IN followed by IM, and the like. Replicon particles are delivered at a dose of at least $10^4$, $10^5$, $10^6$, $10^7$ or $10^8$ infectious units (IU), one or more times. Immunogenicity is determined by standard measurements of binding antibody (ELISA) and/or neutralizing antibody, and protection may be determined following virus challenge as documented in the literature (see for example, Prince et al., 2001, J. Gen. Virol. 82:2881-2888; Li et al., 2000, Virology 269:54-65).

Example 19

Stimulation of a Human Metapneumovirus Specific Immune Response Using an Alphavirus Replicon Particle Vaccine Expressing G Antigen Replicon particles are used to stimulate an immune response to a human metapneumovirus (HMPV) following administration to a warm-blooded mammal. For example, replicon particles expressing both the HMPV G antigen, as described in Examples 10, are evaluated in multiple animal models (e.g., mice, cotton rats, ferrets, monkeys) prior to clinical evaluation in humans.

The formulations are administered by any of a variety of routes, such as for example TIM, IN, SC, ID, IN followed by IM, and the like. Replicon particles are delivered at a dose of at least $10^4$, $10^5$, $10^6$, $10^7$ or $10^8$ infectious units (IU), one or more times. Immunogenicity is determined by standard measurements of binding antibody (ELISA) and/or neutralizing antibody, and protection may be determined following standard virus challenge.

Example 20

Stimulation of an Immune Response Against Multiple Respiratory Virus Pathogens Using an Alphavirus Replicon Particle Vaccine Co-expressing Two Antigens The alphavirus-derived constructs and teachings above, multiple additional bicistronic constructs are constructed (FIG. 5). These constructs may include genes encoding proteins from more than one respiratory pathogen, such as the viral, bacterial and/or fungal pathogens described above. Such constructs preferably are based on the use of duplicated subgenomic promoters or IRES elements (described previously) as a means to achieve co-expression of heterologous sequences (antigen-encoding sequences).

The present invention contemplates the use of such constructs encoding antigens from different pathogens as combination in and vaccines. Non-limiting examples of such constructs include for example, alphavirus replicon constructs expressing: a RSV protein-encoding gene+a PIV protein-encoding gene (e.g., PIV HN+RSV F), a RSV protein-encoding gene+a human metapneumovirus protein-encoding gene (e.g., RSV G+HMPV G), a FLU protein-encoding gene+a SARS virus protein-encoding gene (e.g., FLU HA+SARS Spike), a SARS virus protein-encoding gene+a HMPV protein-encoding gene (e.g., SARS Spike+HMPV F), and the like. The construction, production and testing of such materials is readily accomplished by one of skill in the art based on the disclosure provided above.

A PIV/RSV combination vaccine was generated, wherein an alphavirus replicon vector is constructed to express both a PIV antigen (e.g., HN glycoprotein) and a RSV antigen (e.g., F glycoprotein). More specifically, the replicon vector construct VCR-Chim2.1-HN$_{PIV3}$ that was previously described above was further modified to co-express RSV F glycoprotein. The F glycoprotein, together with an alphavirus subgenomic promoter, was amplified by PCR under standard conditions using the template VCR-Chim2.1-F$_{RSV}$ (also described above) and the following oligonucleotide primers:

```
SGP-forward:
                                (SEQ ID NO: 33)
5'-ATATATATATGCGGCCGCTGGAGGGTTTATTTTGTGTGAC RSV F-reverse:
                                (SEQ ID NO: 34)
5'-ATATATATATCCGCGGCCGCTTAGTTACTAAATGCAATATTATTTA
TAC
```

The PCR fragment containing the alphavirus subgenomic junction region promoter operably linked to the RSV F gene was digested with NotI and ligated into VCR-Chim2.1-HN$_{PIV3}$ that also was digested with NotI and treated with alkaline phosphatase, to create the bicistronic construct VCR-Chim2.1-HN$_{PIV3}$-sgp-F$_{RSV}$.

The bicistronic alphavirus replicon vector was used to produce a replicon particle based PIV/RSV combination vaccine preparation (designated VEE/SIN-HN$_{PIV3}$-sgp-F$_{RSV}$) and expression of both the RSV F and PIV HN antigens was confirmed by immunostaining using appropriate antigen-specific antibodies.

Figure 24B:
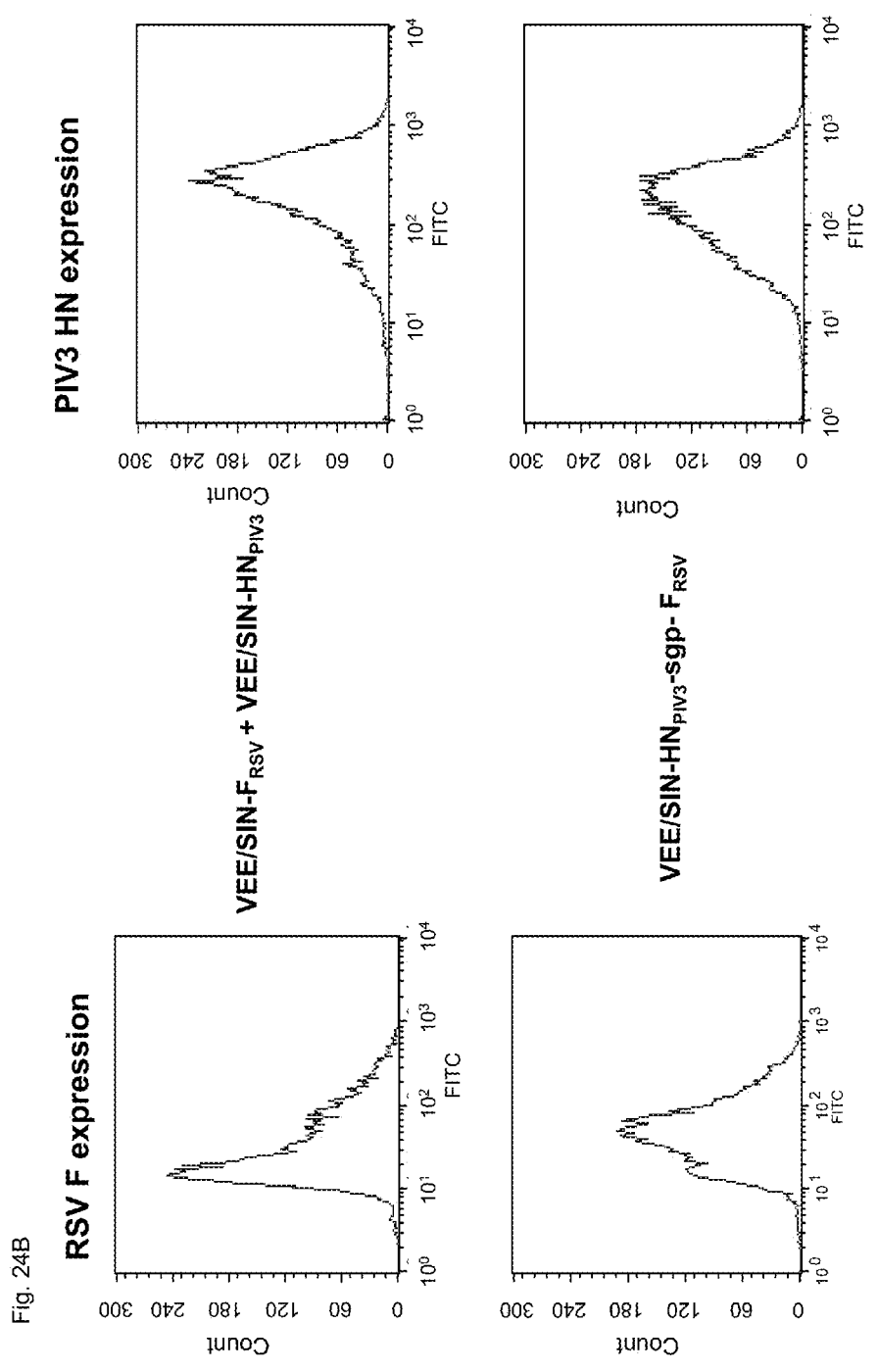

Referring now to FIG. 24, there are shown the results of Fluorescent Activated Cell sorting studies demonstrating expression of the two heterologous antigens in cells by the replicon vector. Cells were harvested, fixed and permeabilized with Cytofix/Cytoperm (PharMigen #554722) and duplicate samples were incubated with either an RSV-specific antibody (goat anti-RSV-FITC conjugated, from Chemicon Int.) or PIV-specific antibody (hamster anti-PIV3 primary antibody, followed by goat anti-hamster-Alexa 488 conjugated, from Molecular Probes, Inc). FIG. 24 demonstrates the expression of both PIV3 HN and RSV F from the bicistronic alphavirus replicon vector.

These replicon particle vaccine preparations may be evaluated in appropriate animal models for immunogenicity and efficacy as detailed above.

Other combinations of antigens from respiratory pathogens may be similarly expressed in a bicistronic configuration for use as an immunogenic or vaccine composition, based on the teachings provided herein.

Example 21

Stimulation of an Immune Response Against Multiple Respiratory Pathogens Using a Vaccine Comprising at Least Two Populations of Alphavirus Replicon Particles Expressing Different Antigens Replicon vector particles that encode one or more polypeptide antigens from a first respiratory pathogen as described above, may be combined with replicon particles that encode one or more polypeptide antigens from a second respiratory pathogen as describe above, as an immunogenic composition useful in the prophylaxis of more than one disease. Such combination vaccines may include a wide variety of different combinations, including at least two such populations of replicon particles, three or more such populations of replicon particles and four or more such combinations of replicon particles.

Further, the present invention contemplates that the immunogenic compositions of the present invention comprising at least two replicon particles encoding antigen(s) from separate respiratory virus pathogens, may include replicon particles that express single antigens or multiple antigens (e.g., bicistronic, see FIGS. 2-5). Non-limiting examples include for example, a RSV protein-encoding gene+a PIV protein-encoding gene (e.g., PIV HN+RSV F), a RSV protein-encoding gene=a human metapneumovirus protein-encoding gene (e.g., RSV G+HMPV G), a FLU protein-encoding gene+a SARS virus protein-encoding gene (e.g., FLU HA+SARS Spike), a SARS virus protein-encoding gene+a HMPV protein-encoding gene (e.g., SARS Spike+HMPV F), and the like.

Other examples, and not by way of limitation, include an immunogenic composition comprising alphavirus replicon particles expressing PIV HN replicon particles expressing RSV G, replicon particles expressing PIV HN+replicon particles expressing HMPV G, replicon particles expressing FLU HA+replicon particles expressing SARS S, replicon particles expressing FLU HA+replicon particles expressing HMPV G, replicon particles expressing SARS S+replicon particles expressing HMPV G, replicon particles co-expressing PIV HN and F+replicon particles co-expressing RSV G and F, and the like. Such immunogenic compositions may be evaluated in appropriate animal models for immunogenicity and efficacy as detailed above.

Specifically, to demonstrate that immunogenic compositions comprising a mixture of at least two populations of replicon particles expressing antigens from different respiratory pathogens induce potent immune responses against each of the multiple encoded antigens without interference, we evaluated proteins from two of the virus pathogens above. VEE/SIN replicon particles expressing FLU HA were combined with VEE/SIN replicon particles expressing PIV HN, in order to produce a combination PIV/FLU vaccine preparation (FIGS. 18, 19 and 25).

Antibody induction with this combination vaccine was compared in head-to-head animal experiments with replicon particles expressing only FLU HA or only PIV-HN. As demonstrated in FIGS. 18 and 25, the replicon particle based PIV/FLU combination vaccine elicited PIV-specific antibody at levels comparable to replicon particles expressing PIV HN alone. The same PIV/FLU combination vaccine also induced FLU HA antibody at levels comparable to replicon particles expressing FLU HA alone (FIG. 19).

An immunogenic vaccine composition comprising a combination of alphavirus replicon particles encoding a RSV F glycoprotein (VEE/SIN-$F_{RSV}$) and alphavirus replicon particles encoding a PIV3 HN glycoprotein (VEE/SIN-$HN_{PIV3}$) was produced using the individual PIV and RSV vaccine components described above. Expression of both the RSV F and PIV HN antigens was confirmed by immunostaining using appropriate antigen-specific antibodies.

FIG. 24 shows the results of Fluorescent Activated Cell sorting studies and demonstrates expression of the two antigens in cells by combined replicon vectors. Cells were harvested, fixed and permeabilized with Cytofix/Cytoperm (PharMigen #554722) and duplicate samples were incubated with either an RSV-specific antibody (goat anti-RSV-FITC conjugated, from Chemicon Int.) or PIV-specific antibody (hamster anti-PIV3 primary antibody, followed by goat anti-hamster-Alexa 488 conjugated, from Molecular Probes, Inc). As shown in FIG. 24, both PIV3 HN and RSV F were expressed from the alphavirus replicon-based PIV/RSV combination vectors.

The replicon particle vaccine preparation are evaluated in appropriate animal models for immunogenicity and efficacy as detailed above.

These results demonstrate the utility of alphavirus replicon particles as a platform for combination vaccines against respiratory pathogens, such as viruses. Other antigens from respiratory pathogens may be similarly expressed in such combinations of replicon particles for use as an immunogenic or vaccine composition, based on the teachings provided herein.

Further, as demonstrated in FIG. 20, such combination vaccines need not necessarily be co-delivered as a mixture of replicon particles. Rather replicon particles expressing a first antigen (in this example, SARS Spike) can be administered, and then followed by immunization with replicon particles expressing a second antigen (in this example, FLU HA), without any inhibition of the response to the second encoded antigens as compared to vaccinating naïve mice with the FLU HA encoding replicon particles.

Recitation of ranges of values herein are merely intended to serve as a shorthand method of referring individually to each separate value falling within the range, unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise described.

Groupings of alternative elements or embodiments of the invention disclosed herein are not to be construed as limitations. Each group member may be referred to and described individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used herein.

Preferred embodiments of this invention are described herein, including the best mode known to the inventors for carrying out the invention. Of course, variations on those preferred embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context.

---

What is claimed is:

1. An immunogenic composition comprising:
   (a) an alphavirus replicon vector comprising:
      (i) a first heterologous nucleic acid sequence encoding a first protein antigen from a first influenza virus, and
      (ii) a second heterologous nucleic acid sequence encoding a second protein antigen from a second influenza virus, wherein said second heterologous nucleic acid sequence is different from said first heterologous nucleic acid sequence; and (b) a pharmaceutically acceptable carrier, diluent, or excipient.

2. The immunogenic composition of claim 1, wherein said first and second protein antigens each is independently selected from the group consisting of: a hemagglutinin (HA), a neuraminidase (NA), a nucleocapsid (NP), a matrix protein (M1), an ion channel protein (M2), NS 1, NS2, PB1, PB2, PA, an immunogenic fragment thereof, and a combination thereof.

3. The immunogenic composition of claim 1, wherein said first protein antigen is an influenza hemagglutinin (HA) or immunogenic fragment thereof.

4. The immunogenic composition of claim 3, wherein said first influenza virus is a subtype selected from the group consisting of H1, H2, H3, H4, H5, H6, H7, H8, H9, H10, H11, H12, H13, H14, and H15 subtypes.

5. The immunogenic composition of claim 1, wherein second protein antigen is an influenza neuraminidase (NA) or immunogenic fragment thereof.

6. The immunogenic composition of claim 1, wherein said second influenza virus is a subtype selected from the group consisting of N1, N2, N3, N4, N5, N6, N7, N8, and N9 subtypes.

7. The immunogenic composition of claim 1, wherein said first protein antigen is an influenza hemagglutinin or immunogenic fragment thereof, and said second protein antigen is an influenza neuraminidase or immunogenic fragment thereof.

8. The immunogenic composition of claim 1, wherein said first and second influenza viruses each is independently a pandemic, potentially pandemic, or interpandemic influenza virus strain.

9. The immunogenic composition of claim 1, wherein said first protein antigen is an influenza hemagglutinin (HA) or immunogenic fragment thereof from a pandemic, potentially pandemic, or interpandemic influenza virus strain.

10. The immunogenic composition of claim 1, wherein said first protein antigen is an influenza hemagglutinin (HA) or immunogenic fragment thereof from a combination of (1) a pandemic or potentially pandemic influenza virus strain, and (2) an interpandemic influenza virus strain.

11. The immunogenic composition of claim 1, wherein the first heterologous nucleic acid sequence is operably linked to a first alphavirus subgenomic promoter.

12. The immunogenic composition of claim 1, wherein the second heterologous nucleic acid sequence is operably linked to a second alphavirus subgenomic promoter.

13. The immunogenic composition of claim 1, wherein the first, second, or both heterologous nucleic acid sequences further comprise an internal ribosome entry site (IRES).

14. The immunogenic composition of claim 1, wherein the alphavirus replicon vector is vector derived from an alphavirus selected from the group consisting of: a Sindbis virus, a Semliki Forest virus, a Venezuelan equine encephalitis virus, and a Ross River virus.

15. A method of stimulating an immune response in a mammal, comprising administering an immunogenic composition of claim 1 to said mammal.

16. The method of claim 15, further comprising administering a second immunogenic composition to said mammal, wherein the second immunogenic composition comprises:

(a) a protein antigen or immunogenic fragment thereof, from the same first influenza strain; and a pharmaceutically acceptable carrier, diluent, or excipient.

* * * * *